United States Patent [19]

Diehr et al.

[11] Patent Number: 4,840,661
[45] Date of Patent: Jun. 20, 1989

[54] SULPHONYLISO(THIO)UREA DERIVATIVES AND HERBICIDAL USE THEREOF

[75] Inventors: Hans-Joachim Diehr; Christa Fest, both of Wuppertal; Rolf Kristen, Monheim; Joachim Kluth, Langenfeld; Klaus-Helmut Müller, Duesseldorf; Theodor Pfister, Monheim; Uwe Priesnitz, Solingen; Hans-Jochem Riebel, Wuppertal; Wolfgang Roy, Langenfeld; Hans-Joachim Santel, Cologne; Robert R. Schmidt, Bergisch Gladbach; Ludwig Eue, Leverkusen, all of Fed. Rep. of Germany

[73] Assignee: Bayer Aktiengesellschaft, Leverkusen, Fed. Rep. of Germany

[21] Appl. No.: 769,272

[22] Filed: Aug. 23, 1985

[30] Foreign Application Priority Data

Aug. 30, 1984 [DE] Fed. Rep. of Germany ....... 3431921
May 17, 1985 [DE] Fed. Rep. of Germany ....... 3517844

[51] Int. Cl.$^4$ .................... A01N 43/02; A01N 43/48; C07D 401/00; C07D 403/00
[52] U.S. Cl. .......................... 71/90; 558/5; 558/8; 544/331; 544/296; 544/310; 544/311; 544/317; 544/319; 544/320; 544/321; 544/323; 544/324; 544/327; 544/332; 544/253; 71/92
[58] Field of Search .................. 558/5, 8; 71/92, 90; 544/331, 296, 310, 311, 317, 319, 320, 321, 323, 324, 327, 332, 253

[56] References Cited

U.S. PATENT DOCUMENTS 4,310,346 1/1982 Levitt et al. ................ 71/92

FOREIGN PATENT DOCUMENTS 0117014 8/1984 European Pat. Off. .......... 544/331

Primary Examiner—Mary C. Lee
Assistant Examiner—Robert C. Whittenbaugh
Attorney, Agent, or Firm—Sprung Horn Kramer & Woods

[57] ABSTRACT

The invention relates relates to new sulphonyliso(thio)-urea derivatives of the general formula (I)

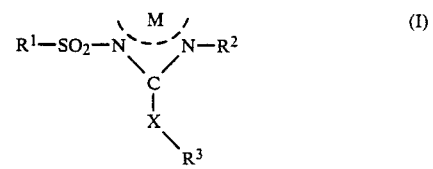

in which
 $R^1$ represent an optionally substituted radical from the series comprising alkyl, aralkyl, aryl and heteroaryl
 $R^2$ represents an optionally substituted and/or optionally fused 6-membered aromatic heterocyclic radial containing at least one nitrogen atom,
 $R^3$ represents an optically substituted aromatic or heteroaromatic radical,
 X represents oxygen or sulphur and
 M represents hydrogen or an equivalent of a metal, and adducts of compounds of the formula (I) with strong acids, processes for their prepartion, and their use as herbicides.

8 Claims, No Drawings

SULPHONYLISO(THIO)UREA DERIVATIVES AND HERBICIDAL USE THEREOF

The invention relates to new sulphonlyiso(thio)urea derivatives, an inventive process for their preparation and their use as herbicides.

Various isoureas and isothioureas have been disclosed as potential herbicides, but have hitherto not found major importance as agents for combating weeds and/or regulating plant growth (compare DE-AS (German Published Specification) No. 1,138,039 and British Patent Specification No. 1,202,736).

New sulphonyliso(thio)urea derivatives of the general formula (I)

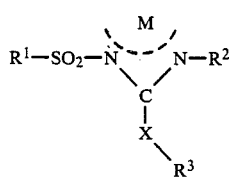

in which
R$^1$ represents an optionally substituted radical from the series comprising alkyl, aralkyl, aryl and heteroaryl,
R$^2$ represents an optionally substituted and/or optionally fused six-membered aromatic heterocyclic radical containing at least one nitrogen atom,
R$^3$ represents an optionally substituted aromatic or heteroaromatic radical,
X represents oxygen or sulphur and
M represents hydrogen or one equivalent of a metal, and adducts of compounds of the formula (I) with strong acids, have now been found.

If M represents hydrogen, the general formula (I) represents the individual tautomers of the formula (Ia) and (Ib)

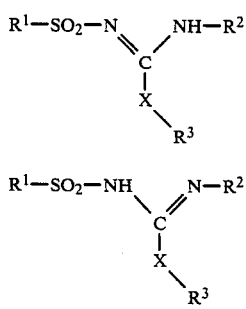

in which
R$^1$, R$^2$, R$^3$ and X have the abovementioned meanings, and mixtures of the tautomers (Ia) and (Ib).

The ratio in the mixture depends on factors which determine the state of aggregation, such as, for example, the temperature, solvent and concentration.

The new sulphonyliso(thio)urea derivatives of the formula (I) are obtained by an inventive process in which sulphonylguanidine derivatives of the formula (II)

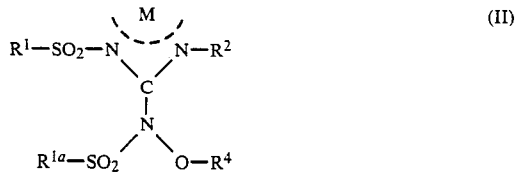

in which
R$^1$, R$^2$ and M have the abovementioned meanings and R$^{1a}$ has the same meaning as R$^1$, but does not have to be identical to R$^1$ in each individual case and
R$^4$ represents an optionally substituted hydrocarbon radical,
are reacted with compounds of the formula (III)

in which
X and R$^3$ have the abovementioned meanings and
M$^1$ represents hydrogen or one equivalent of a metal, if appropriate in the presence of bases and in the presence of diluents, and, if appropriate, the products of the formula (I) thereby obtained are treated with acids.

The new sulphonyliso(thio)urea derivatives of the formula (I) and their adducts with strong acids are distinguished by a powerful herbicidal activity.

Surprisingly, the new compounds of the formula (I) exhibit a considerably better herbicidal action than the already known isourea and isothiourea derivatives of the same type of action.

It is also to be regarded as surprising that the compounds according to the invention, of the formula (I), can be prepared by selective cleavage of sulphonylguanidine derivatives of the formula (II), since in addition to this novel reaction other cleavage reactions, for example as a result of attack at the sulphonyl groupings, would also have been expected.

The invention preferably relates to compounds of the formula (I) in which
R$^1$ represents the radical

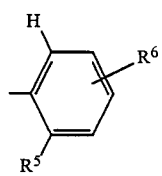

wherein
R$^5$ and R$^6$ are identical or different and represent hydrogen, halogen [such as, in particular, fluorine, chlorine, bromine and/or iodine], cyano, nitro, C$_1$–C$_6$-alkyl [which is optionally substituted by fluorine, chlorine, bromine, cyano, carboxyl, C$_1$–C$_4$-alkoxycarbonyl, C$_1$–C$_4$-alkylaminocarbonyl, di-(C$_1$–C$_4$-alkyl)-amino-carbonyl, hydroxyl, C$_1$–C$_4$-alkoxy, formyloxy, C$_1$–C$_4$-alkylcarbonyloxy, C$_1$–C$_4$-alkoxy-carbonyloxy, C$_1$–C$_4$-alkylamino-carbonyloxy, C$_1$–C$_4$-alkylthio, C$_1$–C$_4$-alkylsulphinyl, C$_1$–C$_4$-alkylsulphonyl, di(C$_1$–C$_4$-alkyl)-aminosulphonyl, C$_3$–C$_6$-cycloalkyl or phenyl], or represent C$_2$–C$_6$-alkenyl [which is optionally substituted by fluorine, chlorine, bromine, cyano, C₁–C₄-alkoxy-carbonyl, carboxyl or phenyl], or represent C₂–C₆-alkinyl [which is optionally substituted by fluorine, chlorine bromine, cyano, C₁–C₄-alkoxy-carbonyl, carboxyl or phenyl], or represent C₁–C₄-alkoxy [which is optionally substituted by fluorine, chlorine, bromine, cyano, carboxyl, C₁–C₄-alkoxy-carbonyl, C₁–C₄-alkoxy, C₁–C₄-alkylthio, C₁–C₄-alkylsulphinyl or C₁–C₄-alkylsulphonyl], or represent C₁–C₄-alkylthio [which is optionally substituted by fluorine, chlorine, bromine, cyano, carboxyl, C₁–C₄-alkoxy-carbonyl, C₁–C₄-alkylthio, C₁–C₄-alkylsulphinyl or C₁–C₄-alkylsulphonyl], or represent C₃–C₆-alkenyloxy [which is optionally substituted by fluorine, chlorine, bromine, cyano or C₁–C₄-alkoxy-carbonyl], or represent C₂–C₆-alkenylthio [which is optionally substituted by fluorine, chlorine, bromine, cyano, nitro, C₁–C₃-alkylthio or C₁–C₄-alkoxy-carbonyl], C₃–C₆-alkinyloxy, C₃–C₆-alkinylthio, or represent the radical —S(O)ₚ—R⁷ wherein
p represents the numbers 1 or 2 and
R⁷ represents C₁–C₄-alkyl [which is optionally substituted by fluorine, chlorine, bromine, cyano or C₁–C₄-alkoxy-carbonyl], C₃–C₆-alkenyl, C₃–C₆-alkinyl, C₁–C₄-alkoxy, C₁–C₄-alkoxyamino, C₁–C₄-alkoxy-C₁–C₄-alkyl-amino, C₁–C₄-alkylamino or di-(C₁–C₄-alkyl)-amino, or
R⁵ and R⁶ furthermore represent phenyl or phenoxy, or represent C₁–C₄-alkylcarbonylamino. C₁–C₄-alkoxy-carbonylamino, C₁–C₄-alkylamino-carbonylamino or di-(C₁–C₄-alkyl)-amino-carbonylamino, or represent the radical —CO—R⁸, wherein
R⁸ represents C₁–C₆-alkyl, C₁–C₆-alkoxy, C₃–C₆-cycloalkoxy, C₃–C₆-alkenyloxy, C₁–C₄-alkylthio, C₁–C₄-alkylamino, C₁–C₄-alkoxyamino, C₁–C₄-alkoxy-C₁–C₄-alkyl-amino or di-(C₁–C₄-alkyl)-amino [which are optionally substituted by fluorine and/or chlorine], or R⁵ and R⁶ furthermore represent C₁–C₄-alkylsulphonyloxy, di-(C₁–C₄-alkyl)-aminosulphonylamino or the radical —CH=N—R⁹, wherein
R⁹ represents C₁–C₆-alkyl which is optionally substituted by fluorine, chlorine, cyano, carboxyl, C₁–C₄-alkoxy, carbonyl, C₁–C₄-alkyl-thio, C₁–C₄-alkylsulphinyl or C₁–C₄-alkyl-sulphonyl, or represents benzyl which is optionally substituted by fluorine or chlorine, or represents C₃–C₆-alkenyl or C₃–C₆-alkinyl, optionally substituted by fluorine or chlorine, or represents phenyl which is optionally substituted by fluorine, chlorine, bromine, C₁–C₄-alkyl, C₁–C₄-alkoxy, trifluoromethyl, trifluoromethoxy or trifluoromethylthio, or represents C₁–C₆-alkoxy, C₃–C₆-alkenoxy, C₃–C₆-alkinoxy or benzyloxy, optionally substituted by fluorine and/or chlorine, or represents amino, C₁–C₄-alkylamino, di-(C₁–C₄-alkyl)amino, phenylamino, C₁–C₄-alkyl-carbonyl-amino, C₁–C₄-alkoxy-carbonylamino or C₁–C₄-alkylsulphonylamino, or represents phenylsulphonylamino which is optionally substituted by fluorine, chlorine, bromine or methyl;

or wherein, furthermore,
R¹ represents the radical

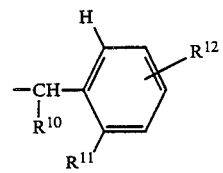

wherein
R¹⁰ represents hydrogen or C₁–C₄-alkyl and
R¹¹ and R¹² are identical or different and represent hydrogen, fluorine, chlorine, bromine, nitro, cyano, C₁–C₄-alkyl [which is optionally substituted by fluorine and/or chlorine], C₁–C₄-alkoxy [which is optionally substituted by fluorine and/or chlorine], carboxyl, C₁–C₄-alkoxy-carbonyl, C₁–C₄-alkylsulphonyl or di(C₁–C₄-alkyl)-aminosulphonyl;

or wherein, furthermore,
R¹ represents the radical

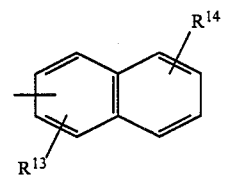

wherein
R¹³ and R¹⁴ are identical or different and represent hydrogen, fluorine, chlorine, bromine, nitro, cyano, C₁–C₄-alkyl [which is optionally substituted by fluorine and/or chlorine] or C₁–C₄-alkoxy [which is optionally substituted by fluorine and/or chlorine];

or wherein, furthermore,
R¹ represents the radical

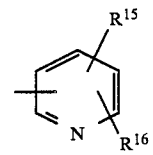

wherein
R¹⁵ and R¹⁶ are identical or different and represent hydrogen, fluorine, chlorine, bromine, nitro, cyano, C₁–C₄-alkyl [which is optionally substituted by fluorine and/or chlorine] or C₁–C₄-alkoxy [which is optionally substituted by fluorine and/or chlorine], or represent C₁–C₄-alkylthio, C₁–C₄-alkylsulphinyl or C₁–C₄-alkylsulphonyl [which are optionally substituted by fluorine and/or chlorine], or represent di-(C₁–C₄-alkyl)-aminosulphonyl or C₁–C₄-alkoxycarbonyl;

or wherein, furthermore,
R¹ represents the radical

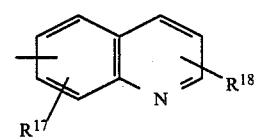

wherein
R$^{17}$ and R$^{18}$ are identical or different and represent hydrogen, fluorine, chlorine, bromine, C$_1$-C$_4$-alkyl [which is optionally substituted by fluorine and/or bromine] or C$_1$-C$_4$-alkoxy [which is optionally substituted by fluorine and/or chlorine], or represent C$_1$-C$_4$-alkylthio, C$_1$-C$_4$-alkylsulphinyl or C$_1$-C$_4$-alkylsulphonyl [which are optionally substituted by fluorine and/or chlorine], or represent di-(C$_1$-C$_4$-alkyl)-aminosulphonyl;

or wherein, furthermore,
R$^1$ represents the radical

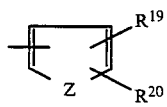

wherein
R$^{19}$ and R$^{20}$ are identical or different and represent hydrogen, fluorine, chlorine, bromine, cyano, nitro, C$_1$-C$_4$-alkyl [which is optionally substituted by fluorine and/or chlorine], C$_1$-C$_4$-alkoxy [which is optionally substituted by fluorine and/or chlorine], C$_1$-C$_4$-alkylthio, C$_1$-C$_4$-alkylsulphinyl or C$_1$-C$_4$-alkylsulphonyl [which is optionally substituted by fluorine and/or chlorine], di-(C$_1$-C$_4$-alkyl)-aminosulphonyl or C$_1$-C$_4$-alkoxy-carbonyl and Z represents oxygen, sulphur or the grouping N—Z$^1$, wherein
Z$^1$ represents hydrogen, C$_1$-C$_4$-alkyl [which is optionally substituted by fluorine, chlorine, bromine or cyano], C$_3$-C$_6$-cycloalkyl, benzyl, phenyl [which is optionally substituted by fluorine, chlorine, bromine or nitro], C$_1$-C$_4$-alkyl-carbonyl, C$_1$-C$_4$-alkoxy-carbonyl or di-(C$_1$-C$_4$-alkyl)-aminocarbonyl;

or wherein, furthermore,
R$^1$ represents the radical

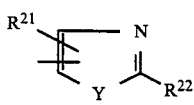

wherein
R$^{21}$ represents hydrogen, C$_1$-C$_5$-alkyl or halogen,
R$^{22}$ represents hydrogen or C$_1$-C$_5$-alkyl and
Y represents sulphur or the grouping N-R$^{23}$
wherein
R$^{23}$ represents hydrogen or C$_1$-C$_5$-alkyl;
and wherein, furthermore,
R$^2$ represents the radical

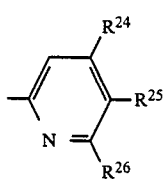

wherein
R$^{24}$ and R$^{26}$ are identical or different and represent hydrogen, fluorine, chlorine, bromine, C$_1$-C$_4$-alkyl [which is optionally substituted by fluorine and/or chlorine] or C$_1$-C$_4$-alkoxy [which is optionally substituted by fluorine and/or chlorine], with the proviso that at least one of the radicals R$^{24}$ and R$^{26}$ are other than hydrogen, and
R$^{25}$ represents hydrogen, fluorine, chlorine, bromine, cyano or C$_1$-C$_4$-alkyl [which is optionally substituted by fluorine and/or chlorine];

or wherein, furthermore,
R$^2$ represents the radical

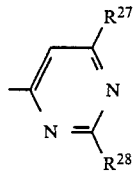

wherein
R$^{27}$ and R$^{28}$ are identical or different and represent hydrogen, fluorine, chlorine, bromine, C$_1$-C$_4$-alkyl [which is optionally substituted by fluorine and/or chlorine], C$_1$-C$_4$-alkoxy [which is optionally substituted by fluorine and/or chlorine], C$_1$-C$_4$-alkylamino or di-(C$_1$-C$_4$-alkyl)-amino, with the proviso that at least one of the radicals R$^{27}$ and R$^{28}$ is other than hydrogen;

or wherein, furthermore,
R$^2$ represents the radical

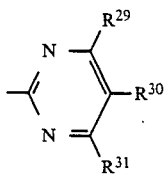

wherein
R$^{29}$ represents hydrogen, fluorine, chlorine, bromine, hydroxyl, C$_1$-C$_4$-alkyl [which is optionally substituted by fluorine and/or chlorine] or C$_1$-C$_4$-alkoxy [which is optionally substituted by fluorine and/or chlorine],
R$^{30}$ represents hydrogen, fluorine, chlorine, bromine, C$_1$-C$_4$-alkyl [which is optionally substituted by fluorine and/or chlorine], cyano, formyl, C$_1$-C$_4$-alkyl-carbonyl or C$_1$-C$_4$-alkoxy-carbonyl and
R$^{31}$ represents hydrogen, fluorine, chlorine, bromine, hydroxyl, C$_1$-C$_4$-alkyl [which is optionally substituted by fluorine and/or chlorine], C$_1$-C$_4$-alkoxy [which is optionally substituted by fluorine and/or chlorine], amino, C$_1$-C$_4$-alkyl-amino or di-(C$_1$-C$_4$-alkyl)-amino, or
R$^{30}$ and R$^{31}$ together represent C$_3$-C$_4$-alkanediyl;

or wherein, furthermore,
R$^2$ represents the radical

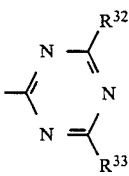

wherein $R^{32}$ and $R^{33}$ are identical or different and represent fluorine, chlorine, bromine, hydroxyl, $C_1$–$C_4$-alkyl [which is optionally substituted by fluorine and/or chlorine], $C_3$–$C_5$-cycloalkyl, $C_1$–$C_4$-alkoxy [which is optionally substituted by fluorine and/or chlorine] or $C_1$–$C_4$-alkylthio, or represnt $C_1$–$C_4$-alkylamino or di-($C_1$–$C_4$-alkyl)-amino;

or wherein, furthermore, $R^2$ represents the radical

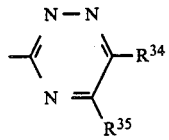

wherein $R^{34}$ and $R^{35}$ are identical or different and represent hydrogen, methyl or methoxy;

and wherein, furthermore, $R^3$ represents a phenyl radical, which is optionally substituted by one or more of the radicals from the series comprising halogen [such as, in particular, fluorine, chlorine, bromine and iodine], cyano, nitro, hydroxyl, carboxyl, $C_1$–$C_6$-alkyl [which is optionally substituted by fluorine, chlorine, bromine, nitro, cyano, hydroxyl, carboxyl, $C_1$–$C_4$-alkoxy-carbonyl, $C_1$–$C_4$-alkoxy, $C_1$–$C_4$-alkylthio or phenyl], $C_3$–$C_6$-cycloalkyl, $C_1$–$C_4$-alkoxy [which is optionally substituted by fluorine, chlorine, bromine, cyano, carboxyl, $C_1$–$C_4$-alkoxy, $C_1$–$C_4$-alkylthio or $C_1$–$C_4$-alkoxy-carbonyl], $C_1$–$C_4$-alkylthio [which is optionally substituted by fluorine, chlorine, bromine, cyano, carboxyl or $C_1$–$C_4$-alkoxy-carbonyl], amino, $C_1$–$C_4$-alkylamino and di-($C_1$–$C_4$-alkyl)-amino [which are optionally substituted by fluorine, chlorine, bromine, cyano, carboxyl, $C_1$–$C_4$-alkoxy or $C_1$–$C_4$-alkoxycarbonyl], $C_1$–$C_4$-alkyl-carbonyl-amino, $C_1$–$C_4$-alkoxy-carbonyl-amino, (di)-$C_1$–$C_4$-alkylaminocarbonyl-amino, formyl, $C_1$–$C_4$-alkyl-carbonyl, benzoyl, $C_1$–$C_4$-alkoxy-carbonyl, phenoxy-carbonyl, benzyloxycarbonyl, phenyl [which is optionally substituted by fluorine, chlorine, bromine, cyano, nitro, hydroxyl or methyl], phenoxy, phenylthio, phenylsulphonyl, phenylamino and phenylazo [which are optionally substituted by fluorine, chlorine, bromine, cyano, nitro, methyl and/or trifluoromethyl], pyridoxy and pyrimidoxy [which are optionally substituted by fluorine, chlorine, bromine, cyano, nitro, methyl and/or trifluoromethyl], $C_1$–$C_4$-alkyl-carbonyloxy, $C_1$–$C_4$-alkoxy-carbonyloxy $C_1$–$C_4$-alkyl-amino-carbonyloxy and di-($C_1$–$C_4$-alkyl)-amino-carbonyloxy, or which is optionally fused with an alkylene chain [which is optionally branched and/or interrupted by one or more oxygen atoms] or a benzo radical [which is optionally substituted by fluorine, chlorine, bromine, cyano, nitro, methyl and/or trifluoromethyl];

or wherein, furthermore, $R^3$ represents a five-membered or six-membered heteroaromatic ring which contains 1 to 3 nitrogen atoms and/or one oxygen or sulphur atom and which is optionally benzo-fused and/or substituted by fluorine, chlorine, bromine, cyano, nitro, $C_1$–$C_3$-alkyl or $C_1$–$C_3$-alkoxy [the latter optionally being substituted by fluorine and/or chlorine];

and wherein, furthermore,

X represents oxygen or sulphur and

M represents hydrogen or one equivalent of sodium, potassium, magnesium, calcium, aluminium, manganese, iron, cobalt or nickel.

The invention furthermore preferably relates to adducts of compounds of the formula (I)—as defined above—with hydrogen halide acids, such as hydrogen fluoride, hydrogen chloride, hydrogen bromide or hydrogen iodide, with sulphuric acid, with alkanesulphonic acids which have 1 to 4 carbon atoms and are optionally substituted by fluorine and/or chlorine, or benzene- or naphthalene-sulphonic acids, which are opitonally substituted by fluorine, chlorine, bromine or methyl.

The invention particularly relates to compounds of the formula (I) in which (A)

$R^1$ represents the radical

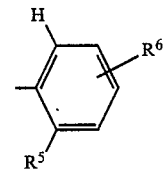

wherein $R^5$ represents fluorine, chlorine, bromine, methyl, trifluoromethyl, methoxy, difluoromethoxy, trifluoromethoxy, $C_1$–$C_3$-alkylthio, difluoromethylthio, trifluoromethylthio, $C_1$–$C_3$-alkylsulphinyl, $C_1$–$C_3$-alkylsulphonyl, dimethylaminosulphonyl, diethylaminosulphonyl, N-methoxy-N-methylaminosulphonyl, phenyl, phenoxy, $C_1$–$C_3$-alkoxy-carbonyl or $C_1$–$C_3$-alkyl-amino-carbonyl and $R^6$ represents hydrogen;

and wherein, furthermore, $R^2$ represents the radical

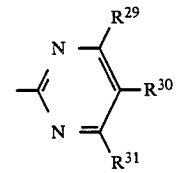

wherein $R^{29}$ represents hydrogen, fluorine, chlorine bromine, hydroxyl, $C_1$–$C_3$-alkyl, $C_1$–$C_3$-alkoxy or difluoromethoxy, $R^{30}$ represents hydrogen, chlorine, bromine or methyl and $R^{31}$ represents $C_1$–$C_3$-alkyl, hydroxyl, fluorine, chlorine, bromine or $C_1$–$C_3$-alkoxy;

and wherein, furthermore, $R^3$ represents a phenyl radical which is optionally substituted by one or two radicals from the series comprising fluorine, chlorine, bromine, iodine, cyano, nitro, hydroxyl, carboxyl, $C_1$–$C_3$-alkoxycarbonyl, $C_1$–$C_4$-alkyl, trifluoromethyl, hydroxymethyl, methoxycarbonylmethyl, phenyl-$C_1$–$C_3$- alkyl, cyclohexyl, $C_1$–$C_3$-alkoxy, trifluoromethoxy, $C_1$–$C_3$-alkylthio, trifluoromethylthio, dimethylamino, amino, acetylamino, methylaminocarbonyl, formyl, acetyl, benzoyl, phenyl, hydroxyphenyl, phenoxy [which is optionally substituted by chlorine and/or trifluoromethyl], phenylamino, phenylazo and pyridoxy [which is optionally substituted by chlorine and/or trifluoromethyl], or which is optionally benzofused;

and wherein, furthermore,

X represents oxygen or sulphur and

M represents hydrogen or one equivalent of sodium, potassium or calcium;

or wherein, furthermore, (B)

$R^1$, $R^3$, X and M have the meaning given above under (A) and $R^2$ represents the radical

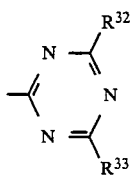

wherein $R^{32}$ represents fluorine, chlorine, cyclopropyl, $C_1$–$C_2$-alkyl, $C_1$–$C_2$-alkoxy or $C_1$–$C_2$-alkylthio and $R^{33}$ represents fluorine, chlorine, cyclopropyl, $C_1$–$C_2$-alkyl, $C_1$–$C_2$-alkoxy, $C_1$–$C_2$-alkylamino or di-($C_1$–$C_2$-alkyl)-amino.

The invention furthermore relates in particular to adducts of compounds of the formula (I)—as defined above—with hydrogen halide acids, such as hydrogen chloride, hydrogen bromide and hydrogen iodide, with sulphuric acid, with alkanesulphonic acids which have 1 to 4 carbon atoms, and are optionally substituted by fluorine and/or chlorine, or with benzene- or naphthalenesulphonic acids which are optionally substituted by fluorine, chlorine, bromine or methyl.

If, for example, N'-(4,6-dimethyl-pyrimidin-2-yl)-N''-methoxy-N'',N'''-bis-(2-methoxycarbonylbenzenesulphonyl)-guanidine and sodium phenolate are used as starting substances in the preparation process according to the invention, the course of the reaction can be outlined by the following equation:

stances in the preparation process according to the invention. In this formula, the radicals $R^1$, $R^2$ and M preferably have the same meanings as are given above as preferred in the context of the definition of the corresponding radicals in formula (I), $R^{1a}$ preferably has the same meaning as is given above as preferred for $R^1$ in the context of the definition of the substituents in formula (I), but does not have to be identical to $R^1$ in each individual case and, $R^4$ preferably represents $C_1$–$C_4$-alkyl or benzyl.

Particularly preferred starting substances of the formula (II) are those in which the radicals $R^1$, $R^2$ and M have the same meanings as are given above as particularly preferred in the context of the definition of the corresponding radicals in formula (I), $R^{1a}$ has the same meaning as is given above as particularly preferred for $R^1$ in the context of the definition of the substituents in formula (I) and $R^4$ represents methyl.

Examples which may be mentioned of the starting substances of the formula (II) are: N'-(4,6-dimethyl-pyrimidin-2-yl)-N''-methoxy
-N'',N'''-bis-(2-chloro-benzenesulphonyl)-,
-N'',N'''-bis-(2-bromo-benzenesulphonyl)-,
-N'',N'''-bis-(2-fluoro-benzenesulphonyl)-,
-N'',N'''-bis-(2-methyl-benzenesulphonyl)-,
-N'',N'''-bis-(2-trifluoromethyl-benzenesulphonyl)-,
-N'',N'''-bis-(2-methoxy-benzenesulphonyl)-,
-N'',N'''-bis-(2-phenyl-benzenesulphonyl)- and
-N'',N'''-bis-(2-methoxycarbonyl-benzenesulphonyl)-guanidine,
N'-(4-methyl-pyrimidin-2-yl)-N''-methoxy-
-N'',N'''-bis-(2-chloro-benzenesulphonyl)-,
-N'', N'''-bis-(2-methoxycarbonyl-benzenesulphonyl)-,
-N'',N'''-bis-(2-difluoromethoxy-benzenesulphonyl)-,
-N'',N'''-bis-(2-diethylaminosulphonyl-benzenesulphonyl)-,
-N'',N'''-bis-(2-bromo-benzenesulphonyl)-,
-N'',N'''-bis-(2-trifluoromethylthio-benzenesulphonyl)-,
-N'',N'''-bis-(2-phenoxy-benzenesulphonyl)- and
-N'', N'''-bis-(2-methylsulphonyl-benzenesulphonyl)-guanidine,
N'-(4,6-dimethoxy-pyrimidin-2-yl)-N''-methoxy-
-N'',N'''-bis-(2-chloro-benzenesulphonyl)-,
-N'',N'''-bis-(2-methoxycarbonyl-benzenesulphonyl)-,
-N'',N'''-bis-(2-difluoromethoxy-benzenesulphonyl)-,
-N'',N'''-bis-(2-trifluoromethoxy-benzenesulphonyl)-,

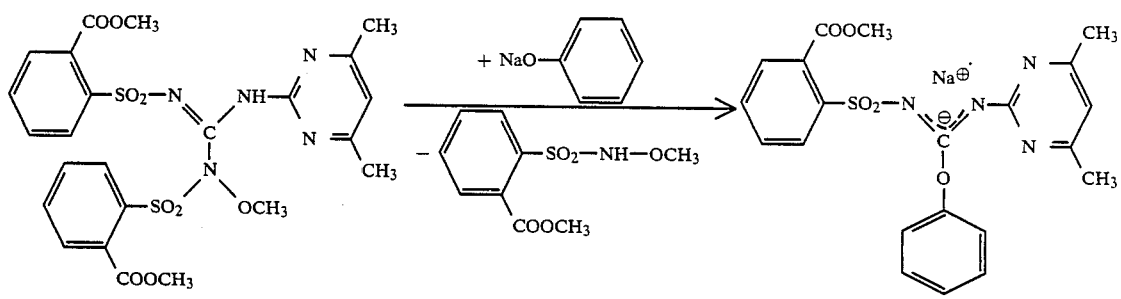

Formula (II) provides a general definition of the sulphonylguanidine derivatives to be used as starting sub- -N'',N'''-bis-(2-dimethylaminosulphonyl-benzenesulphonyl)-,
-N'',N'''-bis-(2-methylthio-benzenesulphonyl)-, -N'',N''''-bis-(2-ethoxycarbonyl-benzenesulphonyl)-,
-N'',N''''-bis-(2-phenyl-benzenesulphonyl)-,
-N'',N''''-bis-(2-cyclopropyloxycarbonyl-benzenesulphonyl)-,
-N'',N''''-bis-(2-trifluoromethylsulphonyl-benzenesulphonyl)-,
-N'',N''''-bis-(2-nitro-benzenesulphonyl)- and
-N'',N''''-bis-(2-cyano-benzenesulphonyl-guanidine,
N'-(4-methoxy-6-methyl-pyrimidin-2-yl)-N''-methoxy-
-N'',N''''-bis-(2-chloro-benzenesulphonyl)-,
-N'',N''''-bis-(2-methoxycarbonyl-benzenesulphonyl)-,
-N'',N''''-bis-(2-methylsulphonyl-benzenesulphonyl)-,
-N'',N''''-bis-(2-methylthio-benzenesulphonyl)-,
-N'',N''''-bis-(2-trifluoromethoxy-benzenesulphonyl)-,
-N'',N''''-bis-(2-ethoxycarbonyl-benzenesulphonyl)-,
-N'',N''''-bis-(2-trifluoromethyl-benzenesulphonyl)-,
-N'',N''''-bis-(2-isopropylthio-benzenesulphonyl)-,
-N'',N''''-bis-(2-N-methoxy-N-methylaminosulphonyl-benzenesulphonyl)-,
-N'',N''''-bis-(2-trifluoromethylthio-benzenesulphonyl)-,
-N'',N''''-bis-(2,5-dichloro-benzenesulphonyl)-,
-N'',N''''-bis-(2-phenoxy-benzenesulphonyl)- and
-N'',N''''-bis-(2-phenyl-benzenesulphonyl)-guanidine,
N'-(4-difluoromethoxy-6-methyl-pyrimidin-2-yl)-N'-methoxy-
-N'',N''''-bis-(2-ethoxycarbonyl-benzenesulphonyl)-,
-N'',N''''-bis-(2-bromo-benzenesulphonyl)-,
-N'',N''''-bis-(2-methylsulphonylmethyl-benzenesulphonyl)-,
-N'',N''''-bis-(2-trifluoromethylthio-benzenesulphonyl)-,
-N'',N''''-bis-(2-methoxy-benzenesulphonyl)-,
-N'',N''''-bis-(2-methoxycarbonyl-benzenesulphonyl)- and
-N'',N''''-bis-(2-chloro-benzenesulphonyl)-guanidine,
N'-(4,6-dimethyl-s-triazin-2-yl)-N''-methoxy-
-N'',N''''-bis-(2-methyl-benzenesulphonyl)-,
-N'',N''''-bis-(2-methoxycarbonyl-benzenesulphonyl)-,
-N'',N''''-bis-(2-methylthio-benzenesulphonyl)-,
-N'',N''''-bis-(2-phenyl-benzenesulphonyl)-,
-N'',N''''-bis-(2-trifluoromethoxy-benzenesulphonyl)-,
-N'',N''''-bis-(2-dimethylaminosulphonyl-benzenesulphonyl)-,
-N'',N''''-bis-(2-chloro-benzenesulphonyl)-,
-N'',N''''-bis-(2-propoxycarbonyl-benzenesulphonyl)- and
-N'',N''''-bis-(2-difluoromethylthio-benzenesulphonyl)-guanidine,
N'-(4-methoxy-6-methyl-s-triazin-2-yl)-N''-methoxy-
-N'',N''''-bis-(2-chloro-benzenesulphonyl)-,
-N'',N''''-bis-(2-phenyl-benzenesulphonyl)-,
-N'',N''''-bis-(2-cyano-benzenesulphonyl)-,
-N'',N''''-bis-(2-methoxycarbonyl-benzenesulphonyl)-,
-N'',N''''-bis-(2-isopropylthio-benzenesulphonyl)-,
-N'',N''''-bis-(2-phenoxy-benzenesulphonyl)- and
-N'',N''''-bis-(2-trifluoromethoxy-benzenesulfonyl)-guanidine,
N'-(4,6-dimethoxy-s-triazin-2-yl)-N''-methoxy-
-N'',N''''-bis-(2-phenyl-benzenesulphonyl)-,
-N'',N''''-bis-(2-phenoxy-benzenesulphonyl)-,
-N'',N''''-bis-(2-chloro-benzenesulphonyl)-,
-N'',N''''-bis-(2-methoxycarbonyl-benzenesulphonyl)-,
-N'',N''''-bis-(2-trifluoromethylthio-benzenesulphonyl)-,
-N'',N''''-bis-(2-benzyl-benzenesulphonyl)-,
-N'',N''''-bis-(2-cyano-benzenesulphonyl)- and
-N'',N''''-bis-(2-isopropoxy-benzenesulphonyl)-guanidine,
N'-(4-ethyl-6-methoxy-s-triazin-2-yl)-N''-methoxy-
-N'',N''''-bis-(2-chloro-benzenesulphonyl)-,
-N'',N''''-bis-(2-phenyl-benzenesulphonyl)-,
-N'',N''''-bis-(2-methoxycarbonyl-benzenesulphonyl)-,
-N'',N''''-bis-(2-trifluoromethyl-benzenesulphonyl)-,
-N'',N''''-bis-(2-difluoromethylthio-benzenesulphonyl)-,
-N'',N''''-bis-(2-dimethylaminosulphonyl-benzenesulphonyl)- and -N'',N''''-bis-(2-cyano-benzenesulphonyl)-guanidine,
N'-(4-dimethylamino-6-methyl-s-triazin-2-yl)-N''-methoxy-
-N'',N''''-bis-(2-chloro-benzenesulphonyl)-,
-N'',N''''-bis-(2-ethoxycarbonyl-benzenesulphonyl)-,
-N'',N''''-bis-(2-chloromethyl-benzenesulphonyl)-,
-N'',N''''-bis-(2-fluoromethyl-benzenesulphonyl)-,
-N'',N''''-bis-(2-iodo-benzenesulphonyl)-,
-N'',N''''-bis-(2-methylthiomethyl-benzenesulphonyl)-,
-N'',N''''-bis-(2-phenyl-benzenesulphonyl)- and
-N'',N''''-bis-(2-trifluoromethoxy-benzenesulphonyl)-guanidine,
N'-(5,6-dimethyl-1,2,4-triazin-3-yl)-N''-methoxy-
-N'',N''''-bis-(2-chloro-benzenesulphonyl)-,
-N'',N''''-bis-(2-difluoromethoxy-benzenesulphonyl)-,
-N'',N''''-bis-(2-methylsulphonylmethyl-benzenesulphonyl)-,
-N'',N''''-bis-(2-methoxycarbonyl-benzenesulphonyl)-,
-N'',N''''-bis-(2-nitro-benzenesulphonyl)- and
-N'',N''''-bis-2-cyano-benzenesulphonyl)-guanidine,
N'-(5-methyl-1,2,4-triazin-3-yl)-N''-methoxy-
-N'',N''''-bis-(2-chloro-benzenesulphonyl)-,
-N'',N''''-bis-(2-phenoxy-benzenesulphonyl)-,
-N'',N''''-bis-(2-propoxycarbonyl-benzenesulphonyl)-,
-N'',N''''-bis-(2-dimethylaminocarbonyl-benzenesulphonyl)-,
-N'',N''''-bis-(2-dimethylaminosulphonyl-benzenesulphonyl)-,
-N'',N''''-bis-(2-bromo-benzenesulphonyl)- and
-N'',N''''-bis-(2-trifluoromethylthio-benzenesulphonyl)-guanidine,
N'-(2,6-dimethyl-pyrimidin-4-yl)-N''-methoxy-
-N'',N''''-bis-(2-fluoro-benzenesulphonyl)-,
-N'',N''''-bis-(2-ethoxycarbonyl-benzenesulphonyl)-,
-N'',N''''-bis-(2-difluoromethoxy-benzenesulphonyl)-,
-N'',N''''-bis-(2-fluoromethyl-benzenesulphonyl)-,
-N'',N''''-bis-(2-cyclopropyloxycarbonyl-benzenesulphonyl)-,
-N'',N''''-bis-(2-phenoxy-benzenesulphonyl)- and
-N'',N''''-bis-(2-phenyl-benzenesulphonyl)-guanidine,
N'-(2,6-dimethoxy-pyrimidin-4-yl)-N''-methoxy-
-N'',N''''-bis-(2-fluoro-benzenesulphonyl)-,
-N'',N''''-bis-(2-methoxycarbonyl-benzenesulphonyl)-,
-N'',N''''-bis-(2-trifluoromethoxy-benzenesulphonyl)-,
-N'',N''''-bis-(2-phenoxy-benzenesulphonyl)-,
-N'',N''''-bis-(2-methylthio-benzenesulphonyl)-,
-N'',N''''-bis-(2-dimethylaminocarbonyl-benzenesulphonyl)-,
-N'',N''''-bis-(2-cyano-benzenesulphonyl)- and
-N'',N''''-bis-(2-methoxymethyl-benzenesulphonyl)-guanidine.

The sulphonyl-guanidine derivatives of the formula (II) to be used as starting substances are the subject of a previous patent application (compare DE-OS (German Published Specification) No. 3,334,455 and EP-A-121,082).

The compounds of the formula (II) are obtained—in the case where $R^1$ and $R^{1a}$ are identical—by a process in which guanidine derivatives of the formula (IV)

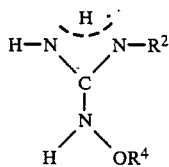 (IV)

in which

R² and R⁴ have the abovementioned meanings, are reacted with at least two molar equivalents of sulphonic acid chlorides of the formula (V)

$$R^1-SO_2-Cl \quad (V)$$

in which

R¹ has the abovementioned meaning, in the presence of acid acceptors, such as, for example, pyridine or diazabicyclooctane (DABCO), and if appropriate in the presence of diluents, such as, for example, methylene chloride or chloroform, at temperatures between −20° C. and +50° C., preferably at 0° C. to 30° C. Working up can be carried out in the customary manner, for example by addition of water, if appropriate acidification, for example with hydrochloric acid, extraction with a solvent which is virtually water-immiscible, such as, for example, methylene chloride or chloroform, washing of the organic phase with water, drying, filtration and concentration. The products of the formula (II) which thereby remain in the residue can in general be made to crystallise with organic solvents and, if appropriate, can be purified by recrystallisation. The compounds of the formula (II) thus obtained in which M represents hydrogen can be converted into corresponding salts of the formula (II)—M: metal equivalent—in the customary manner by reaction with metal compounds in suitable diluents, for example with sodium methylate in methanol.

The guanidine derivatives of the formula (IV) required as intermediates are also the subject of the abovementiond previous patent application (compare DE-OS (German Published Specification) No. 3,334,455).

These guanidine derivatives are obtained by a process in which cyanoamino compounds of the formula (VI)

$$NC-NH-R^2 \quad (VI)$$

in which

R² has the abovementioned meaning, are reacted with hydroxylamine derivatives of the formula (VII)

$$H_2N-OR^4 \quad (VII)$$

in which

R⁴ has the abovementioned meaning, or hydrochlorides thereof, if appropriate in the presence of diluents, such as, for example, ethanol or butanol, at temperatures between 20° C. and 150° C., preferably between 50° C. and 120° C., and, if appropriate, the products are then treated with acid acceptors, such as, for example, (aqueous) ammonia, sodium hydroxide or potassium carbonate. The guanidine derivatives (IV) are in general obtained here as crystals.

The cyanoamino compounds of the formula (VI) are known in some cases (compare J. Chem. Soc. 1953, 1725–1730). These compounds are essentially obtained by the following synthesis routes:

(1) in general by reaction of alkali metal or alkaline earth metal salts of cyanamide—such as, for example, sodium cyanamide or calcium cyanamide—with halogen compounds of the formula (VIII)

$$Hal^1-R^2 \quad (VIII)$$

in which

R² has the abovementioned meaning and
Hal¹ represents fluorine, chlorine, bromine or iodine, in particular chlorine, if appropriate in the presence of inert diluents, such as, for example, acetone, acetonitrile or dimethylformamide, at temperatures between 0° C. and 150° C., preferably between 10° C. and 100° C.; after the volatile component has been distilled off and the residue has been dissolved in water, the cyanoamino compounds of the formula (VI) can be precipitated by acidification, for example with hydrochloric acid, and isolated by filtration with suction; or (2) in the case where R² represents a substituted pyrimidinyl radical, by reaction of a cyanoguanidine ("dicyanamide") with β-dicarbonyl compounds or if appropriate acetals or enol ethers thereof, such as, for example, acetylacetone (compare J. Chem. Soc. 1953, 1725–1730), acetoacetic acid esters (compare J. Prakt. Chem. 77, (1908), 542 and J. Chem. Soc. 1948, 586) or malonic acid esters (compare German Patent Specification No. 158,591). The 2-cyano-amino-4-hydroxy-6-methyl- or -4,6-dihydroxy-pyrimidines obtained from acetoacetic acid esters or malonic acid esters can be converted into the corresponding 2-cyanoamino-4-alkoxy-6-methyl- or -4,6-dialkoxy-pyrmidines in a known manner by reaction with alkylating agents, such as, for example, dimethyl sulphate or diethyl sulphate, if appropriate in the presence of diluents, such as, for example, water, methanol, ethanol, n- and iso-propanol, acetone, dioxane or dimethylformamide, and in the presence of acid-binding agents, such as, for example, sodium hydroxide, potassium hydroxide, sodium carbonate or potassium carbonate. To avoid N-alkylation, if appropriate, acylation is carried out with an acylating agent, such as, for example, acetic anhydride or acetyl chloride, and, after the alkylation, the product is deacylated again with aqueous acids or bases.

In another alternative process, the cyanoamino compounds of the formula (VI) are obtained by a process in which (3) amino compounds of the formula (IX)

$$H_2N-R^2 \quad (IX)$$

in which

R² has the abovementioned meaning,
are reacted with carbonyl isothiocyanates of the formula (X)

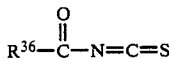

(X)

in which

R³⁶ represents ethoxy or phenyl,
if appropriate in the presence of an inert diluent, such as, for example, acetone, acetonitrile or toluene, at temperatures between 0° C. and 100° C., the resulting carbonylthioureas of the formula (XI)

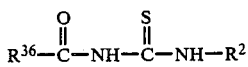

(XI)

in which

R³⁶ and R² have the abovementioned meanings,
are isolated by filtration with suction, if appropriate after the mixture has been concentrated, and are reacted with aqueous alkali metal or alkaline earth metal hydroxide solutions, such as, for example, sodium hydroxide solution, if appropriate in the presence of an organic solvent, such as, for example, tetrahydrofuran or dioxane, at temperatures between 0° C. and 120° C., and the thioureas of the formula (XII)

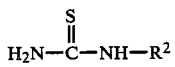

(XII)

in which

R² has the abovementioned meaning,
which are obtained in crystalline form after acidification, for example with hydrochloric acid, are isolated by filtration with suction, and reacted with metal compounds which are capable of binding hydrogen sulphide, such as, for example, with lead(II) acetate, copper(II) acetate, mercury(II) acetate or iron(II) acetate, in the presence of aqueous alkali metal or alkaline earth metal hydroxide solutions, such as, for example, sodium hydroxide solution, at temperatures between 20° C. and 100° C., the mixture is filtered when the reaction is complete, and the filtrate is acidified with an acid, such as, for example, acetic acid. The products of the formula (VI) which are obtained in crystalline form in this procedure can be isolated by filtration with suction.

The starting substances for the preparation process, described above under (1), (2) and (3), for the cyanamino compounds of the formula (VI) are known and/or can be prepared by processes known per se.

These include the halogen compounds of the formula (VIII) (compare G 35, 28-30), the amino compounds of the formula (IX) (compare G 35, 31-2) and the carbonyl isothiocyanates of the formula (X) (compare J. Heterocycl. Chem. 5, (1968, 837 and U.S. Pat. No. 4,160,037).

The hydroxylamine derivatives of the formula (VII) are known or they can be prepared by processes which are known per se (compare Chem. Pharm. Bull. 15 (1967), 345-349; Bull. Soc. Chim. France 1958, 664; and Synthesis 1976, 682).

The sulphonic acid chlorides of the formula (V) are known in some cases (compare Chemistry Lett. 1978, 951; European Published Applications Nos. 23,422, 35,893, 42,731, 44,808, 44,809, 51,466, 64,804 and 70,041; U.S. Pat. Nos. 2,929,820, 4,282,242 and 4,372,778; J. Org. Chem. 33 (1968), 2104 and J. General Chem. 39 (1969), 2011).

These compounds are essentially obtained by the following two synthesis routes:

(1) by reaction of the corresponding sulphonic acids R¹SO₃H or alkali metal or alkaline earth metal salts thereof with halogenating agents, such as, for example, phosphorus-V chloride (phosphorus pentachloride), phosphoryl chloride (phosphorus oxychloride), thionyl chloride, phosgene or benzotrichloride, if appropriate in the presence of catalysts, such as, for example, pyridine or dimethylformamide, and if appropriate using inert diluents, such as, for example, methylene chloride, chloroform, acetonitrile, chlorobenzene and/or sulpholane, at temperatures between $-20°$ C. and $+150°$ C., preferably between 0° C. and $+100°$ C.; after dilution with water, the sulphonic acid chlorides—if these are obtained as crystals—can be isolated by filtration with suction or can be purified by extraction with a water-immiscible solvent, such as, for example, methylene chloride, diethyl ether or hexane, washing and drying of the extracts, concentration and recrystallisation or distillation; or (2) in a manner which is known per se (compare J. Org. Chem. 25 (1960), 1824; DE-OS (German published specification) No. 2,308,262 and European published application No. 59,241) by reaction of corresponding amino compounds R¹—NH₂ with sodium nitrite and hydrochloric acid, if appropriate in the presence of acetic acid, at temperatures between $-10°$ C. and $+20°$ C., preferably between $-5°$ C. and $+10°$ C., and subsequently (in situ) with sulphur dioxide or a salt of sulphurous acid, such as, for example, sodium sulphite or sodium bisulphite, in the presence of a copper compound, such as, for example, copper chloride or copper sulphate, as the catalyst, at temperatures between 0° C. and 80° C., preferably between 10° C. and 60° C.

Working up can be effected in the customary manner: on dilution with water, the sulphonic acid chlorides are in general obtained as crystals and can be isolated by filtration with suction. However, they can also be extracted from the aqueous dispersion with a solvent which is virtually water-immiscible, such as, for example, methylene chloride or diethyl ether, dried, and purified by vacuum distillation.

The starting materials of the formula (II) are also obtained by a process in which monosulphonylguanidines of the formula (XIII)

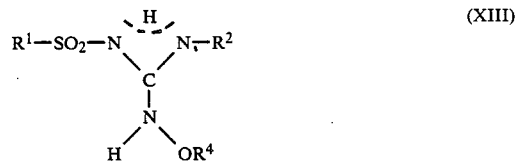

(XIII)

in which

R¹, R² and R⁴ have the abovementioned meanings,
are reacted with sulphonic acid chlorides of the formula (XIV)

$$R^{1a}-SO_2-Cl \qquad (XIV)$$

in which $R^{1a}$ has the abovementioned meaning,
in the presence of acid acceptors, such as, for example, pyridine or diazabicylcooctane (DABCO), and if appropriate in the presence of diluents, such as, for example, methylene chloride, or chloroform, at temperatures between −20° C. and +50° C., preferably at 0° C. to +30° C. Workingup and, where relevant, conversion to metal compounds can be carried out as described above.

The monosulphonylguanidines of the formula (XIII) which may be used as starting substances can be prepared by the following processes:

(a) by reaction of guanidine derivatives of the formula (IV)—above—with approximately stoichiometric amounts of sulphonic acid chlorides of the formula (V)—above—in the presence of acid acceptors, such as, for example, pyridine or diazabicyclooctane (DABCO), and if appropriate in the presence of diluents, such as, for example, methylene chloride, chloroform or tetrahydrofuran, at temperatures between −20° C. and +50° C., preferably at 0° C. to 30° C. Working up can be carried out as described above for the compounds of the formula (II).

(b) By reaction of sulphonylguanidine derivatives of the formula (II)—above—with hydroxylamine derivatives of the formula (VIII)—above—or with their hydrochlorides, if appropriate in the presence of acid acceptors, such as, for example, triethylamine, and if appropriate in the presence of diluents, such as, for example, ethanol, at temperatures between 0° C. and 150° C., preferably between 10° C. and 100° C. The compounds of the formula (XIII) are obtained in general in crystalline form in this procedure.

(c) By reaction of sulphonylisothiourea derivatives of the formula (XV)

$$R^1-SO_2-N\overset{H}{\underset{\underset{R^{37}}{S}}{\overset{}{\diagdown}}}C-N-R^2 \qquad (XV)$$

in which $R^1$ and $R^2$ have the abovementioned meanings and
$R^{37}$ represents $C_1$-$C_4$-alkyl or benzyl,
with hydroxylamine derivatives of the formula (VII)—above—or with their hydrochlorides, if appropriate in the presence of acid acceptors, such as, for example, triethylamine, and if appropriate in the presence of diluents, such as, for example, dioxane, at temperatures between 0° C. and 150° C., preferably 20° C. and 120° C. The compounds of the formula (XIII) are obtained in general in crystalline form in this procedure.

(d) in the case in which $R^1$ represents the radical

[structure: benzene ring with CO—$R^8$]

wherein $R^8$ represents alkoxy, cycloalkoxy, alkenyloxy, alkylthio, alkylamino, alkoxyamino, alkoxy-alkylamino or dialkylamino,
by reaction of benzolactam sultams of the formula (XVI)

[structure (XVI): benzene ring fused with ring containing CO—N(OR$^4$)—C(=NH—R$^2$)—N—SO$_2$]

in which $R^2$ and $R^4$ have the abovementioned meanings,
with compounds of the formula (XVII)

$$M^1-R^8 \qquad (XVII)$$

in which $R^8$ has the abovementioned meaning and
$M^1$ represents hydrogen, sodium or potassium,
if appropriate in the presence of diluents, such as, for example, methanol or ethanol, at temperatures between 0° C. and 150° C., preferably between 20° C. and 100° C. The compounds of the formula (XIII) are obtained in general in crystalline form in this procedure.

(e) In the case in which $R^1$ represents the radical

[structure: benzene ring with $SO_2$—NHOR$^{38}$]

wherein $R^{38}$ represents alkyl,
by reaction of benzodisultams of the formula (XVIII)

[structure (XVIII): benzene ring fused with ring containing $SO_2$—N(OR$^{38}$)—C(=NH—R$^2$)—N—SO$_2$]

in which $R^2$ and $R^{38}$ have the abovementioned meanings,
with compounds of the formula (VII)

$$H_2N-OR^4 \qquad (VII)$$

in which $R^4$ has the abovementioned meaning,
or their hydrochlorides, if appropriate in the presence of diluents, such as, for example, methanol or ethanol, at temperatures between 0° C. and 150° C., preferably between 20° C. and 100° C. The compounds of the formula (XIII) are obtained in general in crystalline form in this procedure.

The sulphonylisothiourea derivatives of the formula (XV) which are stated above as starting substances are known and/or can be prepared by processes which are known per se (compare EP-A No. 5,986).

The benzolactams of the formula (XVI) furthermore stated as starting substances are not known from the literature to date. Various benzolactam sultams form the subject of patent applications of the Applicant which do not form part of the published prior art (compare DE-OS (German published specifications) Nos. 3,431,915, 3,431,920 and 3,431,927). The benzolactam sultams of the formula (XVI) are obtained by reaction of guanidine derivatives of the formula (IV)—above—with 2-chlorosulphonylbenzoyl chloride in the presence of acid acceptors, such as, for example, pyridine, and if appropriate in the presence of diluents, such as, for example, methylene chloride, at temperatures between −30° C. and +50° C., preferably between −10° C. and +30° C. Working up can be carried out as described above for the compounds of the formula (II).

2-Chlorosulphonyl-benzoyl chloride (compare DE-OS (German published specification) No. 2,036,171) and the compounds of the formula (XVII) are known.

The benzodisultams of the formula (XVIII) furthermore stated above as starting substances are not known from the literature to date. Various benzodisultams form the subject of patent applications of the Applicant which do not form part of the published prior art (compare DE-OS (German published specifications) Nos. 3,431,918, 3,431,922 and 3,431,929). The benzodisultams of the formula (XVIII) are obtained by reaction of guanidine derivatives of the formula (IV) with benzene-1,2-disulphonyl dichloride of the formula (XIX)

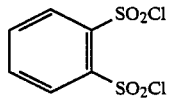

(XIX)

in the presence of acid acceptors, such as, for example, pyridine, and if appropriate in the presence of diluents, such as, for example, methylene chloride, at temperatures between −80° C. and +100° C., preferably between −40° C. and +50° C. Working up can be carried out as described above for the compounds of the formula (II).

Benzene-1,2-disulphonyl chloride of the formula (XIX) is known (compare J. Org. Chem. 31 (1966), page 3289 et seq.).

Formula (III) provides a general definition of the compounds also to be used as starting substances in the preparation process according to the invention. In this formula, X and $R^3$ preferably have the same meanings as are mentioned as preferred in the context of the definition of X and $R^3$ in formula (I) and $M^1$ preferably represents hydrogen, sodium or potassium.

Particularly preferred starting substances of the formula (III) are those in which X and $R^3$ have the same meanings as are given above as particularly preferred in the context of the definition of X and $R^3$ in formula (I) and $M^1$ represents hydrogen, sodium or potassium.

Examples which may be mentioned of the starting substances of the formula (III) are: phenol, 2-, 3- or 4-fluoro-phenol, 2-, 3- or 4-chloro-phenol, 2-, 3- or 4-bromo-phenol, 4-iodo-phenol, 2,3-dichloro-phenol, 2,4-dichloro-phenol, 2,5-dichloro-phenol, 4-cyano-phenol, 2-, 3- or 4-nitro-phenol, 4-chloro-3-nitro-phenol, 3-chloro-4-nitro-phenol, pyrocatechol (1,2-dihydroxy-benzene), resorcinol (1,3-dihydroxy-benzene), hydroquinone (1,4-dihydroxy-benzene), 2-, 3- or 4-hydroxy-benzoic acid, 2-, 3- or 4-methyl-phenol, 3,4-dimethyl-phenol, 3,5-dimethyl-phenol, 4-isopropyl-phenol, 4-tert.-butyl-phenol, 4-chloro-3,5-dimethyl-phenol, 4-hydroxy-benzyl alcohol, 3-methyl-4-nitro-phenol, 4-chloro-3-methyl-phenol, 3- or 4-trifluoromethyl-phenol, methyl 4-hydroxy-phenylacetate, 4-(1-methyl-1-phenyl-ethyl)-phenol, 4-cyclohexyl-phenol, methyl or ethyl 3- or 4-hydroxy-benzoate, 2-, 3- or 4-methoxy-phenol, 4-trifluoromethoxy-phenol, 4-methylthio-phenol, 3-methyl-4-methylthio-phenol, 4-trifluoromethylthio-phenol, 3-dimethylamino-phenol, 3-methyl-4-dimethylamino-phenol, 4-methyl-3-dimethylamino-phenol, 4-acetylamino-phenol, 3-hydroxy- or 4-hydroxy-benzaldehyde, 4-hydroxy-acetophenone, 4-hydroxy-benzophenone, 4-hydroxy-biphenyl, 4,4'-bis-hydroxy-biphenyl, 1-naphthol, 2-naphthol, 3-hydroxy-biphenyl, 4-hydroxy-azobenzene, 4-hydroxy-diphenylamine, 3-hydroxy-diphenylamine, 3-phenoxy-phenol, 4-phenoxy-phenol, 4-(2,4-dichloro-phenoxy)-phenol, 4-(4-trifluoromethyl-phenoxy)-phenol, 4-(3,5-dichloro-2-pyridoxy)-phenol, 4-(3-chloro-5-trifluoromethyl-2-pyridoxy)-phenol, 3-hydroxy-pyridine, 3-hydroxy-6-methyl-pyridine, 8-hydroxy-quinoline, thiophenol, 4-chloro-thiophenol, 4-methyl-thiophenol, 2-amino-thiophenol, 3-amino-thiophenol, 4-amino-thiophenol, 2-methoxy-thiophenol, 3-methoxy-thiophenol, 4-methoxy-thiophenol, 2-mercapto-benzoic acid and 4-hydroxy-thiophenol, and the sodium and potassium salts of these compounds.

The starting substances of the formula (III) are known products which are largely commercially available.

The preparation process according to the invention is preferably carried out using diluents. Possible diluents are virtually all the inert organic solvents, and if appropriate also water, mixed with these solvents. Particularly suitable alcohols, such as, for example, methanol, ethanol, n- or i-propanol and n-, i-, sec.- or tert.-butanol, ketones, such as, for example, acetone, methyl ethyl ketone or methyl isobutyl ketone, and furthermore acetonitrile, dimethylformamide and dimethylsulphoxide.

If appropriate, the process according to the invention is carried out using bases. Possible bases are virtually all the acid-binding agents which are usually employed. These include, in particular, metal hydroxides, carbonates, hydrides and alcoholates, such as, for example, the hydroxides of sodium, potassium and calcium, potassium carbonate, sodium hydride, calcium hydride, sodium methylate, ethylate or propylate, potassium methylate, ethylate or tert.-butylate and aluminium isopropylate.

The reaction temperatures can be varied within a substantial range in the process according to the invention. In general, the reaction is carried out at temperatures between 0° C. and 150° C., preferably between 10° C. and 100° C. The process according to the invention is in general carried out under normal pressure.

For carrying out the process according to the invention, in general between 1 and 3 moles, preferably between 1.1 and 2.0 moles, of hydroxy or mercapto compound, or salts thereof, of the formula (III) are employed per mole of sulphonylguanidine derivative of the formula (II). The reaction components are usually brought together at room temperature or with external cooling and the reaction mixture is stirred, if appropriate at elevated temperature, until the reaction has ended.

The new compounds are worked up and isolated by customary methods:

if the products of the formula (I) are obtained as metal salts, they in general crystallise out of the reaction solution and can be isolated directly by filtration with suction; otherwise, after concentration of the mixture, they can be made to crystallise by digestion with suitable organic solvents, such as, for example, ethanol or acetone. The corresponding salt-free compounds can in general be obtained from the salt-like products of the formula (I) by dispersion in water and acidification, for example with acetic acid. Alternatively, the salt-free products of the formula (I) can be obtained after concentration of the reaction mixture, if appropriate acidification of the residue, for example with hydrochloric acid, shaking with water and an organic solvent which is virtually water-immiscible, such as, for example, methylene chloride or chloroform, separating off the organic phase, drying, filtration and concentration, and can be made to crystallise with suitable organic solvents, such as, for example, toluene or ethanol.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used. The active compounds according to the invention can be used, for example, with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Concolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be used for selectively combating monocotyledon and dicotyledon weeds in monocotyledon and dicotyledon crops, such as, for example, soya bean, cotton, rice, cereals and maize.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysation products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, a finished formulation or tank mix being possible.

The active compounds according to the invention can be applied by themselves and in combination with other active compounds. Possible mixing partners are: ureas (for example methabenzthiazuron, isoproturon, chlorotoluron and fluometuron), triazines (for example atrazine), triazinones (for example metribuzin, metamitron and 4-amino-6-tert.-butyl-3-ethylthio-1,2,4-triazin-5(4H)-one), triazinediones (for example ametridione), chloroacetamides (for example alachlor and metolachlor), cyclohexanediones (for example sethoxydim), heteroaryloxy- or aryloxy-phenoxypropionic acids (for example 2-(benzyloxy)-ethyl (2R)-2-[4-(3,5-dichloro-pyridyl-2-oxy)-phenoxy]propionate and (trimethyl-silyl)-methyl (2R)-2-[4-(3,5-dichloro-pyridyl-2-oxy)-phenoxy]-propionate, halogenoalkanecarboxylic acids (for example 2,4-D, 2,4-DP, MCPA and MCPP), diphenyl ethers (for example fomesafen and aclonifen), and furthermore bentazon and pyridazines (for example pyridate).

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.001 and 15 kg of active compound per hectare of soil surface, preferably between 0.01 and 10 kg per ha.

The active compounds (I) according to the invention also exhibit fungicidal activity, for example activity against *Pyricularia oryzae* in rice and against scab fungi, for example apple scab.

The preparation and use of the active compounds according to the invention can be seen from the following examples.

PREPARATION EXAMPLES

Example 1

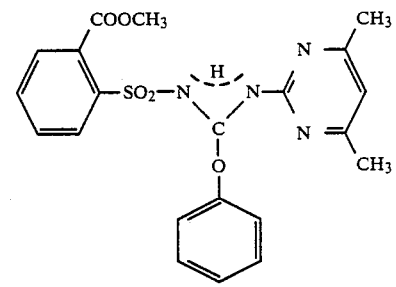

A mixture of 5.9 g (0.01 mole) of N'-(4,6-dimethyl-pyrimidin-2-yl)-N''-methoxy-N'',N'''-bis-(2-methoxycarbonyl-benzenesulphonyl)-guanidine, 2.4 g (0.02 mole) of sodium phenolate, 30 ml of ethanol and 5 ml of water is stirred at 50° C. for 10 hours. The mixture is then concentrated to dryness under a water-pump vacuum and the residue is digested with ethanol and filtered off with suction. The crystalline product is recrystallised from aqueous acetic acid.

1.5 g (34% of theory) of N'-(4,6-dimethylpyrimidin-2-yl)-N''-(2-methoxycarbonyl-benzenesulphonyl)-O-phenyl-isourea of melting point 120° C. are obtained.

Example 2

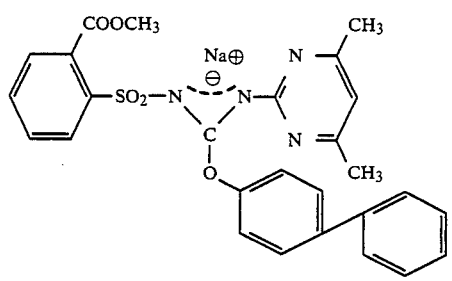

A mixture of 3.5 g (0.02 mole) of 4-hydroxy-biphenyl, 1.1 g (0.02 mole) of sodium methylate and 30 ml of ethanol is stirred at 20° C. to 30° C. for 2 hours. 5.9 g (0.01 mole) of N'-(4,6-dimethyl-pyrimidin-2-yl)-N''-methoxy-N'',N'''-bis-(2-methoxycarbonyl-benzenesulphonyl)-guanidine are then added and the reaction mixture is stirred at 60° C. for 2 days. After cooling, the product is filtered off with suction.

4.8 g (89% of theory) of the sodium salt of N'-(4,6-dimethyl-pyrimidin-2-yl)-N''-(2-methoxycarbonylbenzenesulphonyl)-O-(biphenyl-4-yl)-isourea of melting point 235° C. (decomposition) are obtained.

Example 3

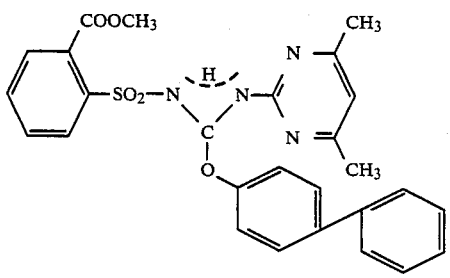

Acetic acid is added dropwise, with stirring, to a mixture of 2.0 g (0.0037 mole) of the sodium salt of N'-(4,6-dimethyl-pyrimidin-2-yl)-N''-(2-methoxycarbonylbenzenesulphonyl)-O-(biphenyl-4-yl)-isourea (compare Example 2) and 10 ml of water until a pH value of about 4.5 is reached. After the mixture has been stirred for about 20 hours, the product is filtered off with suction.

1.8 g (94% of theory) of N'-(4,6-dimethyl-pyrimidin-2-yl)-N''-(2-methoxycarbonyl-benzenesulphonyl)-O-(biphenyl-4-yl)-isourea of melting point 71° C. are obtained.

Example 4

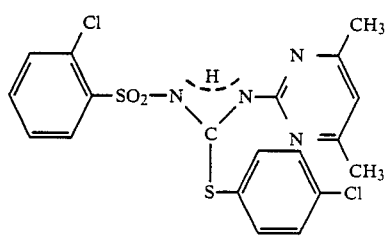

A solution of 1.5 g (0.027 mole) of sodium methylate in 5 ml of methanol is added to a mixture of 13.8 g (0.025 mole) of N'-(4,6-dimethyl-pyrimidin-2-yl)-N''-methoxy-N'',N'''-bis-(2-chloro-benzenesulphonyl)guanidine, 3.7 g (0.025 mole) of 4-chlorothiophenol and 50 ml of ethanol, with stirring, and the reaction mixture is heated at the boiling point under reflux for 2 hours. After cooling, water and methylene chloride are added, the mixture is shaken in a separating funnel and the organic phase is separated off, dried, filtered and concentrated to dryness. The residue is made to crystallise with diethyl ether.

3.0 g (26% of theory) of N'-(4,6-dimethyl-pyrimidin-2-yl)-N''-(2-chloro-benzenesulphonyl)-S-(4-chlorophenyl)-isothiourea of melting point 140° C. are obtained.

The compounds of the formula (Ic) listed in Table 1 below can be prepared analogously to Example 1 to 4:

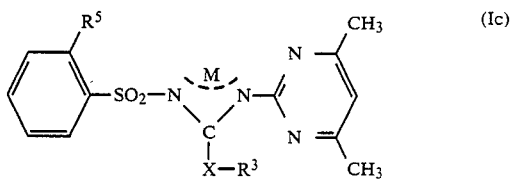

TABLE 1

| Example No. | M | X | $R^5$ | $R^3$ | Melting point [°C.] |
|---|---|---|---|---|---|
| 5 | H | O | Cl | phenyl | 115 |
| 6 | Na | O | COOCH$_3$ | phenyl | 190 |
| 7 | ½ Ca | O | COOCH$_3$ | phenyl | 167 |

TABLE 1-continued
| Example No. | M | X | R⁵ | R³ | Melting point [°C.] |
|---|---|---|---|---|---|
| 8 | K | O | COOCH₃ | 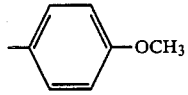 —⟨C₆H₄⟩—OCH₃ | 147 |
| 9 | Na | O | COOCH₃ | 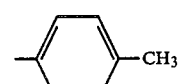 —⟨C₆H₄⟩—CH₃ | 151 |
| 10 | Na | O | COOCH₃ | 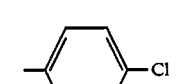 —⟨C₆H₄⟩—Cl | 181 |
| 11 | Na | O | COOCH₃ | 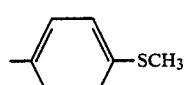 —⟨C₆H₄⟩—SCH₃ | 146 |
| 12 | Na | O | COOCH₃ | 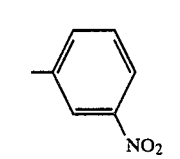 —⟨C₆H₄⟩—NO₂ (meta) | 155 |
| 13 | Na | O | COOCH₃ | 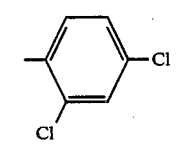 —⟨C₆H₃⟩(2,4-Cl₂) | 90 |
| 14 | Na | O | COOCH₃ | 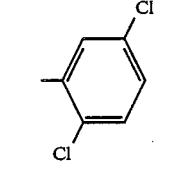 —⟨C₆H₃⟩(2,5-Cl₂) | 57 |
| 15 | H | O | COOCH₃ | 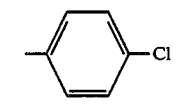 —⟨C₆H₄⟩—Cl | 64 |
| 16 | Na | O | COOCH₃ | 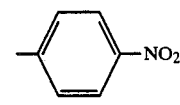 —⟨C₆H₄⟩—NO₂ | 55 |
| 17 | H | O | COOCH₃ | 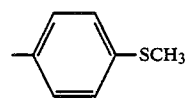 —⟨C₆H₄⟩—SCH₃ | 42 |
| 18 | H | O | COOCH₃ | 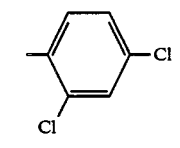 —⟨C₆H₃⟩(2,4-Cl₂) | (ol) |
| 19 | H | O | COOCH₃ | 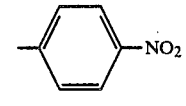 —⟨C₆H₄⟩—NO₂ | (ol) |

TABLE 1-continued
| Example No. | M | X | R⁵ | R³ | Melting point [°C.] |
|---|---|---|---|---|---|
| 20 | H | O | COOCH₃ | 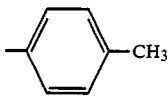 4-CH₃-C₆H₄- | 95 |
| 21 | H | O | Cl | 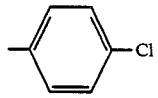 4-Cl-C₆H₄- | 55 |
| 22 | Na | O | Cl | 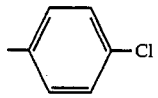 4-Cl-C₆H₄- | 174 |
| 23 | Na | O | Cl | 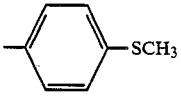 4-SCH₃-C₆H₄- | 135 |
| 24 | Na | O | Cl | 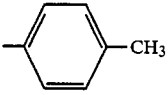 4-CH₃-C₆H₄- | 150 |
| 25 | Na | O | COOCH₃ | 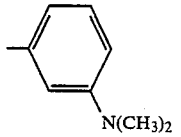 3-N(CH₃)₂-C₆H₄- | 175 |
| 26 | H | O | COOCH₃ | 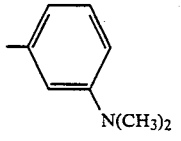 3-N(CH₃)₂-C₆H₄- | 35 |
| 27 | Na | O | Cl | 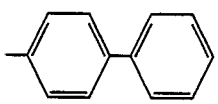 4-biphenyl | 187 |
| 28 | H | O | Cl | 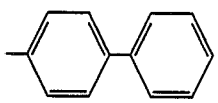 4-biphenyl | 143 |
| 29 | Na | O | COOCH₃ | 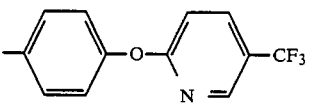 | 174 |
| 30 | Na | O | COOCH₃ | 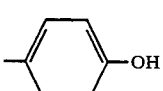 4-OH-C₆H₄- | 188 |
| 31 | Na | O | Cl | 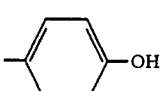 4-OH-C₆H₄- | 165 |

TABLE 1-continued

| Example No. | M | X | R⁵ | R³ | Melting point [°C.] |
|---|---|---|---|---|---|
| 32 | Na | O | Cl | 4-(3-chloro-5-chloro-pyridin-2-yloxy)phenyl | 175 |
| 33 | Na | O | Cl | 4-(5-trifluoromethyl-pyridin-2-yloxy)phenyl | 165 |
| 34 | Na | O | Br | 3-(N,N-dimethylamino)phenyl | 165 |
| 35 | Na | O | Br | 4-biphenyl | 170 |
| 36 | Na | O | COOCH₃ | 3-formylphenyl (CHO) | 162 |
| 37 | Na | O | COOCH₃ | 4-(3-chloro-5-chloro-pyridin-2-yloxy)phenyl | 172 |
| 38 | H | S | Cl | phenyl | 125 |
| 39 | H | S | Cl | 4-hydroxyphenyl | 196 |
| 40 | H | S | Cl | 4-(O—CO—NHCH₃)phenyl | 160 |
| 41 | H | S | Cl | 2-aminophenyl | 231 |
| 42 | H | S | Cl | 4-methylphenyl | 163 |
| 43 | H | S | COOCH₃ | 4-methylphenyl | (oil) |

TABLE 1-continued

| Example No. | M | X | $R^5$ | $R^3$ | Melting point [°C.] |
|---|---|---|---|---|---|
| 44 | H | S | COOCH$_3$ | phenyl | 138 |
| 45 | H | S | COOCH$_3$ | 4-hydroxyphenyl | 160 |
| 46 | H | O | OCF$_3$ | phenyl | 101 |
| 47 | H | O | OCF$_3$ | phenyl | 133 |
| 48 | Na | O | COOCH$_3$ | 4-(2-phenylpropan-2-yl)phenyl | 182 |
| 49 | Na | O | COOCH$_3$ | 4-chloro-3,5-dimethylphenyl | 171 |
| 50 | Na | O | COOCH$_3$ | 4-(methylthio)-3-methylphenyl | 173 |
| 51 | Na | O | COOCH$_3$ | 4-chloro-3-methylphenyl | 183 |
| 52 | Na | O | COOCH$_3$ | 4'-hydroxybiphenyl-4-yl | 175 |
| 53 | Na | O | COOCH$_3$ | 4-(ethoxycarbonyl)phenyl | 138 |
| 54 | Na | O | COOCH$_3$ | 3-hydroxyphenyl | 168 |
| 55 | Na | O | COOCH$_3$ | 4-tert-butylphenyl | 175 |

TABLE 1-continued
| Example No. | M | X | R⁵ | R³ | Melting point [°C.] |
|---|---|---|---|---|---|
| 56 | Na | O | COOCH₃ | 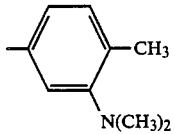 | 106 |
| 57 | Na | O | COOCH₃ | 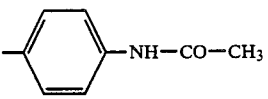 | 118 |
| 58 | Na | O | COOCH₃ | 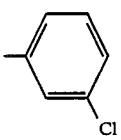 | 125 |
| 59 | Na | O | COOCH₃ | 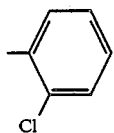 | 169 |
| 60 | Na | O | COOCH₃ | 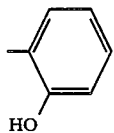 | 74 |
| 61 | Na | O | COOCH₃ | 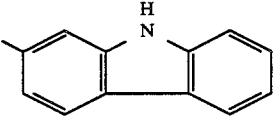 | 204 |
| 62 | Na | O | COOCH₃ | 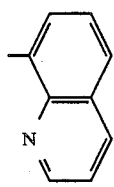 | 160 |
| 63 | H | O | COOCH₃ | 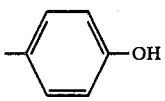 | 135 |
| 64 | H | O | COOCH₃ | 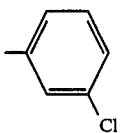 | 122 |
| 65 | H | O | COOCH₃ | 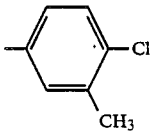 | 172 |

TABLE 1-continued

| Example No. | M | X | R⁵ | R³ | Melting point [°C.] |
|---|---|---|---|---|---|
| 66 | H | O | COOCH₃ | 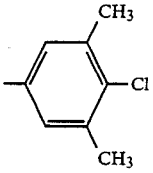 | 116 |

Example 67

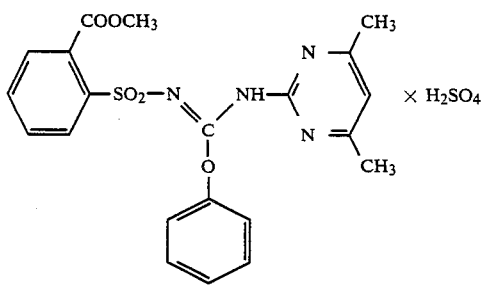

× H₂SO₄

Melting point: 71° C.–73° C.

Example 68

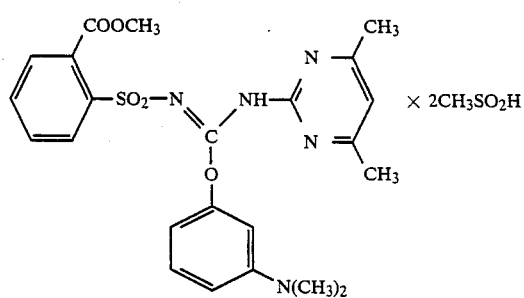

× 2CH₃SO₂H

Melting point: 112° C.

Example 69

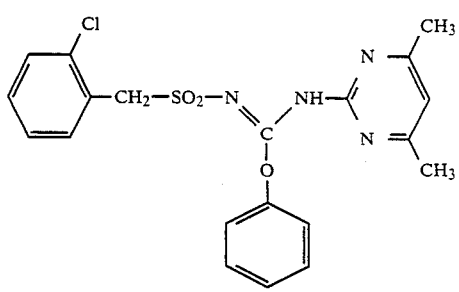

Melting point: 153° C.

Example 45a

The mono-sodium salt of the compound of Example 45 (amorphous)

The compounds of the formula (Id) listed in Table 2 below can furthermore be prepared analogously to Example 1 to 4:

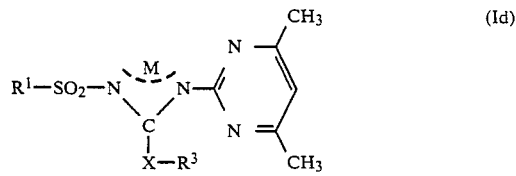 (Id)

TABLE 2

| Example No. | M | X | R¹ | R³ | Melting point [°C.] |
|---|---|---|---|---|---|
| 70 | H | O | 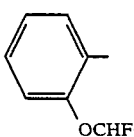(OCHF₂) | 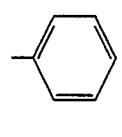 | 113 |
| 71 | H | S | 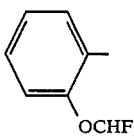(OCHF₂) | 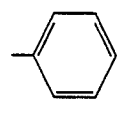 | 107 |
| 72 | H | O | 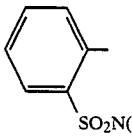(SO₂N(CH₃)₂) | 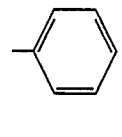 | 168 |

TABLE 2-continued

| Example No. | M | X | R¹ | R³ | Melting point [°C.] |
|---|---|---|---|---|---|
| 73 | H | S | 2-(SO₂N(CH₃)₂)-phenyl | phenyl | |
| 74 | H | O | 2-CH₃-phenyl | phenyl | |
| 75 | H | S | 2-CH₃-phenyl | 4-OH-phenyl | |
| 76 | H | O | 2-COOC₂H₅-phenyl | 4-C(CH₃)₃-phenyl | |
| 77 | H | S | 2-Br-phenyl | 4-OH-phenyl | |
| 78 | H | O | 2-(CH₂—SO₂CH₃)-phenyl | phenyl | |
| 79 | H | S | 2-(CH₂—SO₂CH₃)-phenyl | phenyl | |
| 80 | H | O | 2-Br-phenyl | phenyl | 131 |
| 81 | H | S | 2-Br-phenyl | phenyl | |
| 82 | H | O | 2-F-phenyl | 4-C(CH₃)₃-phenyl | 154 |

TABLE 2-continued
| Example No. | M | X | R¹ | R³ | Melting point [°C.] |
|---|---|---|---|---|---|
| 83 | H | S | 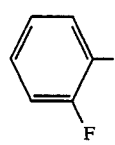 2-F-phenyl | 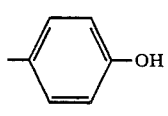 4-OH-phenyl | |
| 84 | H | O | 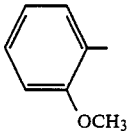 2-OCH₃-phenyl | 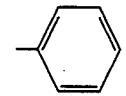 phenyl | |
| 85 | H | S | 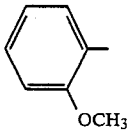 2-OCH₃-phenyl | 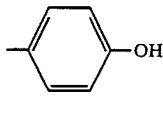 4-OH-phenyl | |
| 86 | H | O | 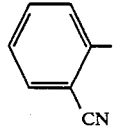 2-CN-phenyl | 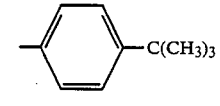 4-C(CH₃)₃-phenyl | |
| 87 | H | S | 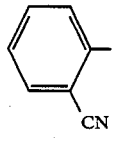 2-CN-phenyl | 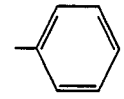 phenyl | |
| 88 | H | O | 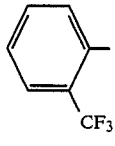 2-CF₃-phenyl | 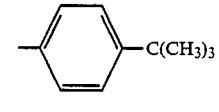 4-C(CH₃)₃-phenyl | 158 |
| 89 | H | S | 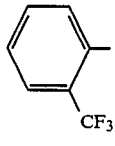 2-CF₃-phenyl | 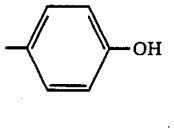 4-OH-phenyl | |
| 90 | H | O | 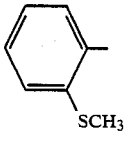 2-SCH₃-phenyl | 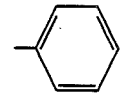 phenyl | |
| 91 | H | S | 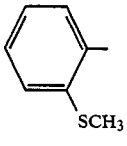 2-SCH₃-phenyl | 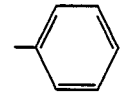 phenyl | |
| 92 | H | O | 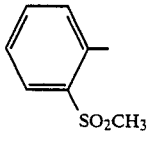 2-SO₂CH₃-phenyl | 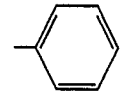 phenyl | |

TABLE 2-continued
| Example No. | M | X | R¹ | R³ | Melting point [°C.] |
|---|---|---|---|---|---|
| 93 | H | S | 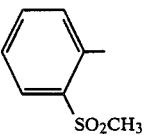 | 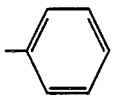 | |
| 94 | H | O | 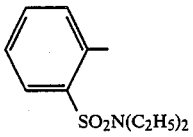 | 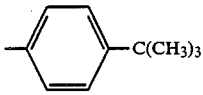 | 147 |
| 95 | H | S | 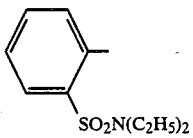 | 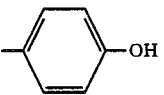 | 211 |
| 96 | H | O | 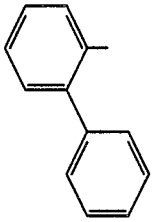 | 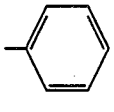 | 139 |
| 97 | H | S | 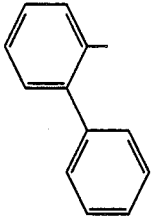 | 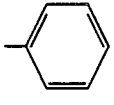 | |
| 98 | H | O | 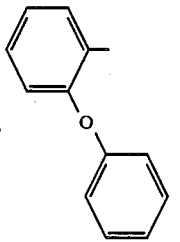 | 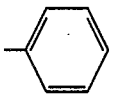 | |
| 99 | H | S | 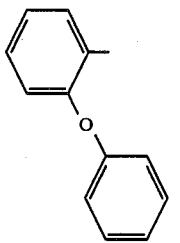 | 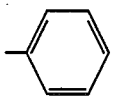 | |

TABLE 2-continued
| Example No. | M | X | R¹ | R³ | Melting point [°C.] |
|---|---|---|---|---|---|
| 100 | H | O | 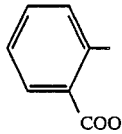 2-COOC₂H₅-phenyl | 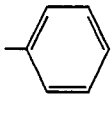 phenyl | 104 |
| 101 | H | S | 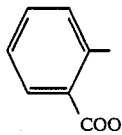 2-COOC₂H₅-phenyl | 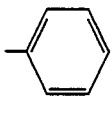 phenyl | |
| 102 | H | O | 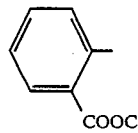 2-COOC₃H₇(—n)-phenyl | 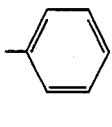 phenyl | 106 |
| 103 | H | S | 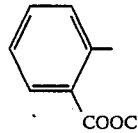 2-COOC₃H₇(—n)-phenyl | 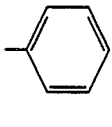 phenyl | |
| 104 | H | O | 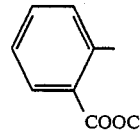 2-COOC₃H₇(—i)-phenyl | 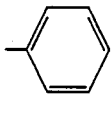 phenyl | |
| 105 | H | S | 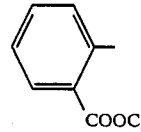 2-COOC₃H₇(—i)-phenyl | 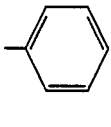 phenyl | |
| 106 | H | O | 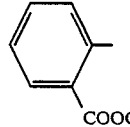 2-COOC₄H₉(—n)-phenyl | 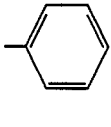 phenyl | 97 |
| 107 | H | S | 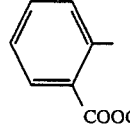 2-COOC₄H₉(—n)-phenyl | 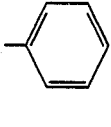 phenyl | |
| 108 | H | O | 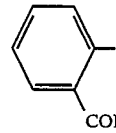 2-CONHCH₃-phenyl | 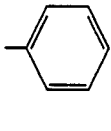 phenyl | |
| 109 | H | S | 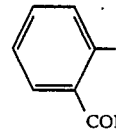 2-CONHCH₃-phenyl | 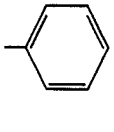 phenyl | |

TABLE 2-continued
| Example No. | M | X | R¹ | R³ | Melting point [°C.] |
|---|---|---|---|---|---|
| 110 | H | O | 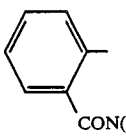CON(CH$_3$)$_2$ |  | |
| 111 | H | S | 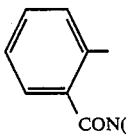CON(CH$_3$)$_2$ |  | |
| 112 | H | O | 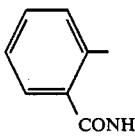CONHOCH$_3$ |  | |
| 113 | H | S | 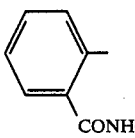CONHOCH$_3$ |  | |
| 114 | H | O | 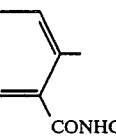CONHC$_4$H$_9$(—n) |  | |
| 115 | H | S | 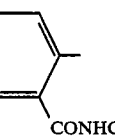CONHC$_4$H$_9$(—n) |  | |
| 116 | H | O | 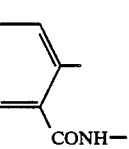CONH—N(CH$_3$)$_2$ |  | |
| 117 | H | S | 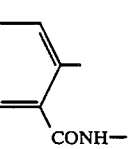CONH—N(CH$_3$)$_2$ |  | |
| 118 | H | O | 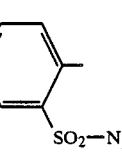SO$_2$—N(CH$_3$)(OCH$_3$) |  | |

TABLE 2-continued

| Example No. | M | X | R¹ | R³ | Melting point [°C.] |
|---|---|---|---|---|---|
| 119 | H | S | 2-(N-methyl-N-methoxysulfamoyl)phenyl | phenyl | |
| 120 | H | O | 2-chlorophenyl | 4-tert-butylphenyl | |
| 121 | H | S | 3-chloro-4-(trifluoromethoxy)phenyl | 4-hydroxyphenyl | |
| 122 | H | O | 2-(ethoxycarbonyl)phenyl | 4-methylphenyl | |
| 123 | H | S | 2-(ethoxycarbonyl)phenyl | 4-hydroxyphenyl | |
| 124 | H | O | 2-(trifluoromethoxy)phenyl | 4-bromophenyl | |
| 125 | H | S | 5-chloro-2-(trifluoromethoxy)phenyl | 4-hydroxyphenyl | |
| 126 | H | O | 2,4,5-trichlorophenyl | phenyl | |
| 127 | H | S | 2,4,5-trichlorophenyl | phenyl | |

TABLE 2-continued

| Example No. | M | X | R¹ | R³ | Melting point [°C.] |
|---|---|---|---|---|---|
| 128 | H | O | 2,4-dichlorophenyl | phenyl | |
| 129 | H | S | 2,4-dichlorophenyl | phenyl | |
| 130 | H | O | 3-(ClF₂C)phenyl | phenyl | |
| 131 | H | S | 3-(ClF₂C)phenyl | phenyl | |
| 132 | H | O | 2,4-dichloro-3-(CF₃)phenyl | phenyl | |
| 133 | H | S | 2,4-dichloro-3-(CF₃)phenyl | phenyl | |
| 134 | H | O | 2,5-dichlorophenyl | phenyl | |
| 135 | H | S | 2,5-dichlorophenyl | phenyl | |
| 136 | H | S | (2-chlorophenyl)CH₂– | phenyl | |
| 137 | H | O | (2-COOCH₃-phenyl)CH₂– | phenyl | |

TABLE 2-continued

| Example No. | M | X | R¹ | R³ | Melting point [°C.] |
|---|---|---|---|---|---|
| 138 | H | S | 2-(COOCH₃)-benzyl-CH₂– | phenyl | |
| 139 | H | O | 2-CN-benzyl-CH₂– | phenyl | |
| 140 | H | S | 2-CN-benzyl-CH₂– | phenyl | |
| 141 | H | O | quinolin-8-yl | phenyl | |
| 142 | H | S | quinolin-8-yl | phenyl | |
| 143 | H | O | 2-OCHF₂-phenyl | 4-CH₃-phenyl | 113 |
| 144 | H | S | 2-OCHF₂-phenyl | 4-CH₃-phenyl | |
| 145 | H | O | 2-SCHF₂-phenyl | phenyl | |
| 146 | H | O | 2-SCF₃-phenyl | phenyl | |

TABLE 2-continued

| Example No. | M | X | R¹ | R³ | Melting point [°C.] |
|---|---|---|---|---|---|
| 147 | H | O | 2-(OCF₃)phenyl | 4-CH₃-phenyl | 131 |
| 148 | H | S | 2-(OCF₃)phenyl | 4-OH-phenyl | 169 |
| 149 | H | S | 2-(OCHF₂)phenyl | 4-OH-phenyl | |
| 150 | H | O | 2-(SO₂N(CH₃)₂)phenyl | 4-CH₃-phenyl | 173 |
| 151 | H | O | 2-Br-phenyl | 4-biphenyl | 128 |
| 152 | H | O | 2-(COOCH₃)phenyl | 2-naphthyl | 119 |
| 153 | H | O | 2-(COOCH₃)phenyl | 4-Br-phenyl | 132 |
| 154 | H | O | 2-(COOCH₃)phenyl | 4-I-phenyl | 129 |
| 155 | H | S | 2-Br-phenyl | 4-Cl-phenyl | 157 |
| 156 | H | O | 2-(SO₂N(C₂H₅)₂)phenyl | phenyl | 152 |

TABLE 2-continued
| Example No. | M | X | R¹ | R³ | Melting point [°C.] |
|---|---|---|---|---|---|
| 157 | H | O | 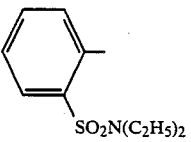 | 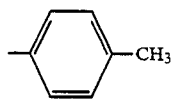 | 142 |
| 158 | H | O | 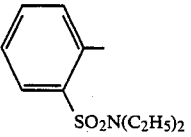 | 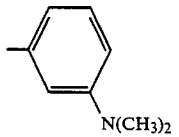 | 188 |
| 159 | H | O | 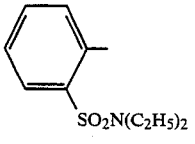 |  | 124 |
| 160 | H | O | 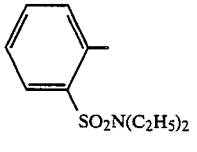 | 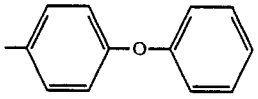 | 140 |
| 161 | H | O | CH₃ | 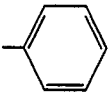 | 138 |
| 162 | H | O | 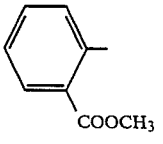 | 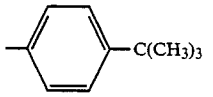 | 170 |
| 163 | H | O |  | 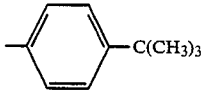 | 161 |
| 164 | H | O | 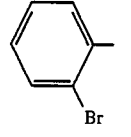 | 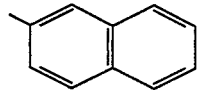 | |
| 165 | H | O | 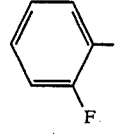 | 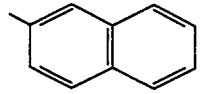 | 67 |
| 166 | H | S | 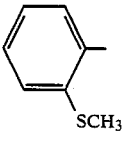 | 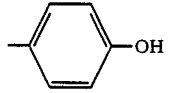 | |

TABLE 2-continued

| Example No. | M | X | R¹ | R³ | Melting point [°C.] |
|---|---|---|---|---|---|
| 167 | H | S | 2-SO₂CH₃-phenyl | 4-OH-phenyl | |
| 168 | H | O | 2-OCHF₂-phenyl | 3-pyridyl | 48 |
| 169 | H | S | 2-COOCH₃-phenyl | benzoxazol-2-yl | 156 |
| 170 | Na | O | 2-SO₂N(CH₃)₂-phenyl | 2-naphthyl | 217 |
| 171 | H | O | 2-SO₂N(CH₃)₂-phenyl | 4-biphenylyl | 172 |
| 172 | H | O | 2-SO₂N(CH₃)₂-phenyl | 4-C₄H₉(—t)-phenyl | 154 |
| 173 | H | O | 2-SO₂N(CH₃)₂-phenyl | 3-N(CH₃)₂-phenyl | 183 |

The compounds of the formula (Ie) listed in Table 3 below can furthermore be prepared analogously to Example 1 to 4:

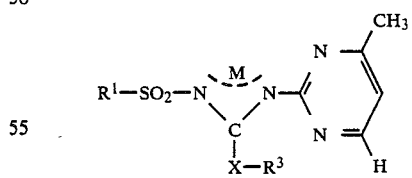

TABLE 3

| Example No. | M | X | R¹ | R³ | Melting point [°C.] |
|---|---|---|---|---|---|
| (Ie-1) | H | O | 2-COOCH₃-phenyl | phenyl | 93–94 |

TABLE 3-continued

| Example No. | M | X | R¹ | R³ | Melting point [°C.] |
|---|---|---|---|---|---|
| (Ie-2) | H | O | 2-COOCH₃-C₆H₄- | 4-CH₃-C₆H₄- | (oil) |
| (Ie-3) | H | O | 2-COOCH₃-C₆H₄- | 3-N(CH₃)₂-C₆H₄- | |
| (Ie-4) | H | O | 2-COOCH₃-C₆H₄- | 4-C₆H₅-C₆H₄- | 208 |
| (Ie-5) | H | S | 2-COOCH₃-C₆H₄- | C₆H₅- | 73 |
| (Ie-6) | H | S | 2-SO₂CH₃-C₆H₄- | 4-OH-C₆H₄- | |
| (Ie-7) | H | O | 2-OCF₃-C₆H₄- | 4-C(CH₃)₃-C₆H₄- | |
| (Ie-8) | H | S | 2-OCHF₂-C₆H₄- | C₆H₅- | |
| (Ie-9) | K | O | 2-SO₂N(CH₃)₂-C₆H₄- | 4-C(CH₃)₃-C₆H₄- | |
| (Ie-10) | H | S | 2-COOCH₃-C₆H₄- | 4-OH-C₆H₄- | 134 |
| (Ie-11) | H | O | 2-COOCH₃-C₆H₄- | 4-C(CH₃)₃-C₆H₄- | 93 |

TABLE 3-continued
| Example No. | M | X | R¹ | R³ | Melting point [°C.] |
|---|---|---|---|---|---|
| (Ie-12) | H | S | 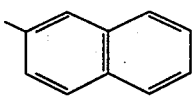 | 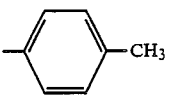 | |
| (Ie-13) | H | O | 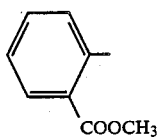 | 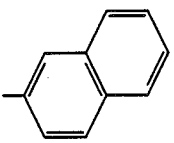 | 196 |
| (Ie-14) | H | O | 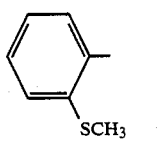 | 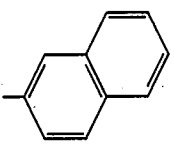 | |
| (Ie-15) | H | O | 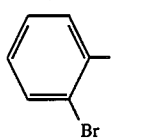 | 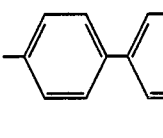 | |
| (Ie-16) | H | O | 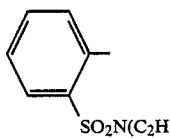 | 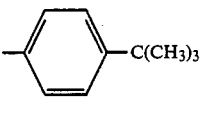 | |
| (Ie-17) | H | S | 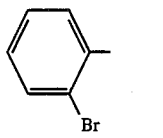 | 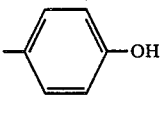 | |
| (Ie-18) | H | S | 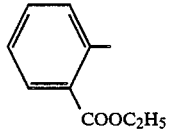 | 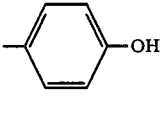 | |
| (Ie-19) | H | S | 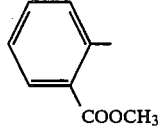 | 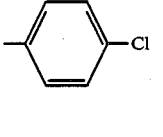 | 112 |
| (Ie-20) | H | S | 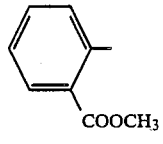 | 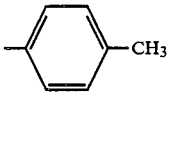 | 126 |
| (Ie-21) | H | O | 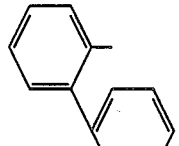 | 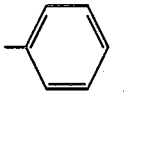 | |

TABLE 3-continued

| Example No. | M | X | R¹ | R³ | Melting point [°C.] |
|---|---|---|---|---|---|
| (Ie-22) | H | S | 2-Cl-phenyl | phenyl | |
| (Ie-23) | H | O | 2-Cl-phenyl | 4-CH₃-phenyl | |
| (Ie-24) | H | S | 2-SCH₃-phenyl | 4-CH₃-phenyl | |
| (Ie-25) | H | O | 2-OCHF₂-phenyl | phenyl | |
| (Ie-26) | H | O | 2-COOCH₃-phenyl | 2-CH₃-phenyl | 118 |
| (Ie-27) | H | O | 2-COOCH₃-phenyl | 4-C₃H₇(-n)-phenyl | 80 |

The compounds of the formula (If) listed in Table 4 below can furthermore be prepared analogously to Example 1 to 4:

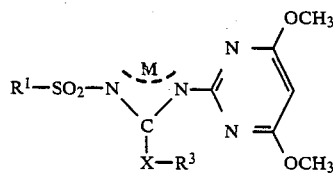
(If)

TABLE 4

| Example No. | M | X | R¹ | R³ | Melting point [°C.] |
|---|---|---|---|---|---|
| (If-1) | H | O | 2-SO₂N(CH₃)₂-phenyl | phenyl | 196 |
| (If-2) | H | S | 2-SO₂N(CH₃)₂-phenyl | 4-C(CH₃)₃-phenyl | 184 |
| (If-3) | H | O | 2-COOCH₃-phenyl | phenyl | 133 |
| (If-4) | H | S | 2-COOCH₃-phenyl | phenyl | 210 |
| (If-5) | H | O | 2-COOCH₃-phenyl | 4-CH₃-phenyl | |

TABLE 4-continued

| Example No. | M | X | R¹ | R³ | Melting point [°C.] |
|---|---|---|---|---|---|
| (If-6) | H | S | 2-COOCH₃-phenyl | 4-CH₃-phenyl | |
| (If-7) | H | O | 2-Cl-phenyl | phenyl | 125 |
| (If-8) | H | S | 2-Cl-phenyl | phenyl | 153 |
| (If-9) | H | O | 2-OCF₃-phenyl | phenyl | 112 |
| (If-10) | H | O | 2-OCF₃-phenyl | 4-CH₃-phenyl | 105 |
| (If-11) | H | O | 2-OCF₃-phenyl | 4-SCH₃-phenyl | 109 |
| (If-12) | H | S | 2-OCF₃-phenyl | phenyl | 147 |
| (If-13) | H | O | 2-OCHF₂-phenyl | phenyl | 142 |
| (If-14) | H | S | 2-OCHF₂-phenyl | phenyl | 168 |
| (If-15) | H | O | 2-OCHF₂-phenyl | 4-CH₃-phenyl | 129 |
| (If-16) | H | S | 2-OCHF₂-phenyl | 4-OH-phenyl | |
| (If-17) | H | O | 2-SCHF₂-phenyl | phenyl | |
| (If-18) | H | S | 2-SCF₃-phenyl | 4-OH-phenyl | |
| (If-19) | H | S | 2-SCF₃-phenyl | phenyl | |
| (If-20) | H | S | 2-SCF₃-phenyl | 4-N(CH₃)₂-phenyl | |
| (If-21) | H | S | 2-SCHF₂-phenyl | 4-OH-phenyl | |
| (If-22) | H | O | 2-SCHF₂-phenyl | 4-CH₃-phenyl | |
| (If-23) | H | O | 2-Br-phenyl | phenyl | |
| (If-24) | H | O | 2-SO₂N(CH₃)(OCH₃)-phenyl | 4-CH₃-phenyl | |
| (If-25) | H | O | 2-(CH₂-COOCH₃)-phenyl | phenyl | |
| (If-26) | H | S | 2-(CH₂-CN)-phenyl | 4-OH-phenyl | |
| (If-27) | H | O | 2-SCH₃-phenyl | 4-CH₃-phenyl | |
| (If-28) | H | O | 2-SCF₃-phenyl | 3-N(CH₃)₂-phenyl | |
| (If-29) | K | O | 2-CH₃-phenyl | 4-phenyl-phenyl | |
| (If-30) | H | O | 2-(CH₂-SO₂CH₃)-phenyl | phenyl | |
| (If-31) | H | S | 2-COOCH₃-phenyl | 4-OH-phenyl | |

TABLE 4-continued

| Example No. | M | X | R¹ | R³ | Melting point [°C.] |
|---|---|---|---|---|---|
| (If-32) | H | O | 2-F-phenyl | 4-CH₃-phenyl | |
| (If-33) | H | S | 2-Cl-phenyl | 4-OH-phenyl | |
| (If-34) | H | O | 2-SO₂N(CH₃)₂-phenyl | naphthyl | 214 |
| (If-35) | H | O | 2-CF₃-phenyl | phenyl | |
| (If-36) | H | O | 2-phenyl-phenyl | phenyl | |

Example (If-34a)

Mono-sodium salt of the compound of Example (If-34) having a melting point of 214° C.

The compounds of the formula (Ig) listed in the Table 5 below can furthermore be prepared analogously to Example 1 to 4:

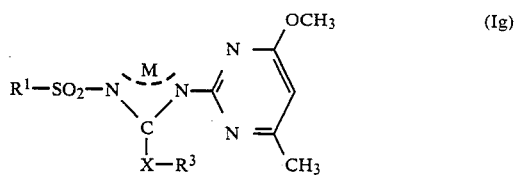

(Ig)

TABLE 5

| Example No. | M | X | R¹ | R³ | Melting point [°C.] |
|---|---|---|---|---|---|
| (Ig-1) | H | O | 2-COOCH₃-phenyl | phenyl | |
| (Ig-2) | H | O | 2-COOC₃H₇-phenyl | 4-CH₃-phenyl | |
| (Ig-3) | H | S | 2-COOC₂H₅-phenyl | 4-OH-phenyl | |
| (Ig-4) | H | O | 2-COOCH₃-phenyl | 4-phenyl-phenyl | |
| (Ig-5) | H | O | 2-OCF₃-phenyl | phenyl | |
| (Ig-6) | H | O | 2-F-phenyl | 4-CH₃-phenyl | |

TABLE 5-continued

| Example No. | M | X | R¹ | R³ | Melting point [°C.] |
|---|---|---|---|---|---|
| (Ig-7) | H | O | 2-(SO₂N(CH₃)₂)-phenyl | 4-Br-phenyl | |
| (Ig-8) | H | O | 2-(SO₂N(CH₃)₂)-phenyl | phenyl | |
| (Ig-9) | H | S | 2-(COOC₂H₅)-phenyl | 4-CH₃-phenyl | |
| (Ig-10) | H | O | 2-(OCHF₂)-phenyl | 4-OCH₃-phenyl | |
| (Ig-11) | H | S | 2-(SCH₃)-phenyl | 4-OH-phenyl | |
| (Ig-12) | H | O | 2-(SO₂CH₃)-phenyl | 2,3,4-tri-CH₃-phenyl | |
| (Ig-13) | H | O | 2-(SO₂−N(CH₃)(OCH₃))-phenyl | phenyl | |
| (Ig-14) | H | S | 2-(CON(CH₃)(OCH₃))-phenyl | 4-CH₃-phenyl | |
| (Ig-15) | H | O | 2-(CON(CH₃)₂)-phenyl | 4-Cl-phenyl | |
| (Ig-16) | H | O | 2-Cl-phenyl | phenyl | |

TABLE 5-continued

| Example No. | M | X | R¹ | R³ | Melting point [°C.] |
|---|---|---|---|---|---|
| (Ig-17) | H | S | 2-Br-phenyl | 4-CH₃-phenyl | |
| (Ig-18) | H | O | 2-Br-phenyl | 2-naphthyl | 160 |
| (Ig-19) | H | O | 2-Br-phenyl | 4-C(CH₃)₃-phenyl | 163 |
| (Ig-20) | H | O | 2-F-phenyl | 2-naphthyl | 185 |
| (Ig-21) | H | O | 2-Br-phenyl | phenyl | 108 |
| (Ig-22) | H | O | 2-Br-phenyl | 4-biphenylyl | amorphous |
| (Ig-23) | H | O | 2-Br-phenyl | 3-N(CH₃)₂-phenyl | 162 |
| (Ig-24) | H | O | 2-COOCH₃-phenyl | 2-naphthyl | 147 |

The compounds of the formula (Ih) listed in the Table 6 below can furthermore be prepared analogously to Example 1 to 4:

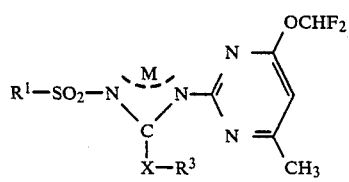
(Ih)

TABLE 6

| Example No. | M | X | R¹ | R³ | Melting point [°C.] |
|---|---|---|---|---|---|
| (Ih-1) | H | O | 2-COOCH₃-phenyl | phenyl | |

TABLE 6-continued

| Example No. | M | X | R¹ | R³ | Melting point [°C.] |
|---|---|---|---|---|---|
| (Ih-2) | H | O | 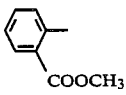 2-COOCH₃-phenyl | 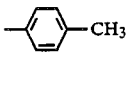 4-CH₃-phenyl | |
| (Ih-3) | H | S | 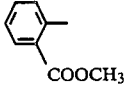 2-COOCH₃-phenyl | 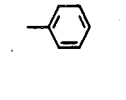 phenyl | |
| (Ih-4) | H | S | 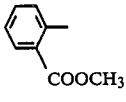 2-COOCH₃-phenyl | 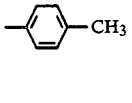 4-CH₃-phenyl | |
| (Ih-5) | H | S | 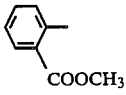 2-COOCH₃-phenyl | 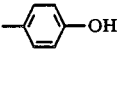 4-OH-phenyl | |
| (Ih-6) | H | O | 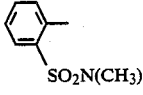 2-SO₂N(CH₃)₂-phenyl | 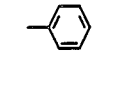 phenyl | |
| (Ih-7) | H | O | 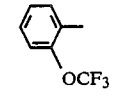 2-OCF₃-phenyl | 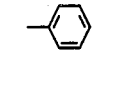 phenyl | |
| (Ih-8) | H | O | 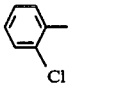 2-Cl-phenyl |  phenyl | |
| (Ih-9) | H | O | 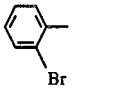 2-Br-phenyl |  phenyl | |
| (Ih-10) | H | O | 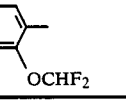 2-OCHF₂-phenyl |  4-CH₃-phenyl | |

The compounds of the formula (Ii) listed in the Table 7 below can furthermore be prepared analogously to Example 1 to 4:

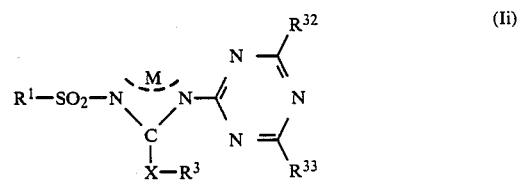

TABLE 7

| Example No. | M | X | R¹ | R³ | R³² | R³³ | Melting point [°C.] |
|---|---|---|---|---|---|---|---|
| (Ii-1) | H | S | 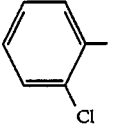 2-Cl-phenyl | 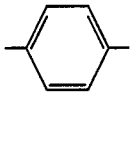 4-OH-phenyl | CH₃ | OCH₃ | 190 |
| (Ii-2) | H | S | 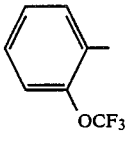 2-OCF₃-phenyl | 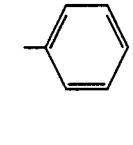 phenyl | CH₃ | OCH₃ | |
| (Ii-3) | H | S | 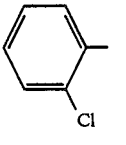 2-Cl-phenyl | 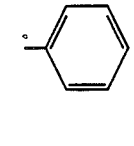 phenyl | CH₃ | OCH₃ | |
| (Ii-4) | H | S | 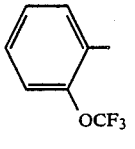 2-OCF₃-phenyl | 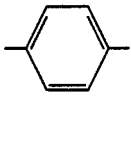 4-OH-phenyl | CH₃ | OCH₃ | |
| (Ii-5) | H | S | 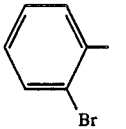 2-Br-phenyl | 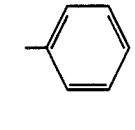 phenyl | CH₃ | OCH₃ | |

TABLE 7-continued

| Example No. | M | X | R¹ | R³ | $R^{32}$ | $R^{33}$ | Melting point [°C.] |
|---|---|---|---|---|---|---|---|
| (Ii-6) | H | S | 2-Br-phenyl | 4-OH-phenyl | $CH_3$ | $OCH_3$ | |
| (Ii-7) | H | O | 2-Cl-phenyl | phenyl | $CH_3$ | $CH_3$ | |
| (Ii-8) | H | S | 2-Cl-phenyl | 4-OH-phenyl | $CH_3$ | $CH_3$ | |
| (Ii-9) | H | S | 2-Br-phenyl | 4-OH-phenyl | $CH_3$ | $CH_3$ | |
| (Ii-10) | H | S | 2-$OCF_3$-phenyl | phenyl | $CH_3$ | $CH_3$ | |
| (Ii-11) | H | S | 2-Cl-phenyl | phenyl | $C_2H_5$ | $OCH_3$ | |
| (Ii-12) | H | S | 2-Cl-phenyl | phenyl | $OCH_3$ | $OCH_3$ | |
| (Ii-13) | H | S | 2-Br-phenyl | 4-OH-phenyl | $OCH_3$ | $OCH_3$ | |
| (Ii-14) | H | S | 2-Cl-phenyl | 4-OH-phenyl | $CH_3$ | $N(CH_3)_2$ | |
| (Ii-15) | H | S | 2-$COOCH_3$-phenyl | 4-OH-phenyl | $OCH_3$ | $N(CH_3)_2$ | |

TABLE 7-continued

| Example No. | M | X | R¹ | R³ | R³² | R³³ | Melting point [°C.] |
|---|---|---|---|---|---|---|---|
| (Ii-16) | H | S | 2-methylphenyl-6-COOCH₃ (ortho-COOCH₃ phenyl) | 4-hydroxyphenyl | SCH₃ | NHC₂H₅ | |

PREPARATION OF STARTING SUBSTANCES OF THE FORMULA (II)

Example (II-1)

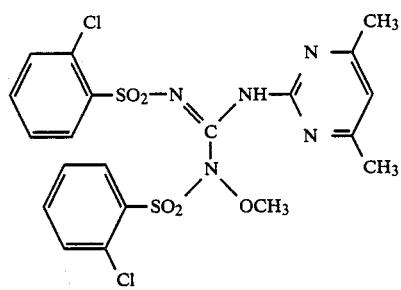

A mixture of 29.4 g (0.15 mole) of N'-(4,6-dimethyl-pyrimidin-2-yl)-N'''-methoxy-guanidine, 63.3 g (0.3 mole) of 2-chloro-benzenesulphonyl chloride and 150 ml of pyridine is stirred at 20° C. for 2 days. After substantial removal of the pyridine by distillation under a waterpump vacuum, 200 ml of water are added to the residue and the mixture is extracted with 200 ml of methylene chloride. The organic phase is separated off, dried and concentrated. The residue is made to crystallise by digestion with ethanol.

41.2 g (51% of theory) of N'-(4,6-dimethylpyrimidin-2-yl)-N''-methoxy-N'',N'''-bis-(2-chloro-benzenesulphonyl)-guanidine of melting point 164° C. to 166° C. are obtained.

Example (II-2)

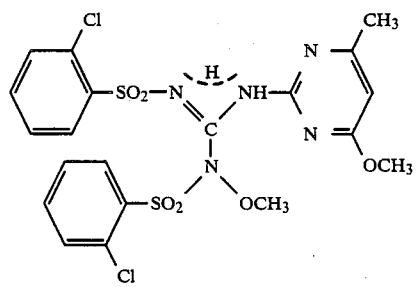

54 g (0.256 mole) of 2-chloro-benzenesulphonyl chloride are added dropwise, while stirring, to a mixture of 97 g (0.25 mole) of N'-(4-methoxy-6-methyl-s-triazin-2-yl)-N''-methoxy-N'''-(2-chloro-benzenesulphonyl)-guanidine and 300 ml of pyridine which has been cooled to −20° C. The reaction mixture is stirred for 15 hours at 20° C. and concentrated. The residue is taken up in 300 ml of methylene chloride, and this solution is washed with twice 150 ml of dilute hydrochloric acid, filtered and concentrated. The product obtained in crystalline form when the residue is triturated with ethanol is isolated by filtration with suction.

80 g (70% of theory) of N'-(4-methoxy-6-methyl-s-triazin-2-yl)-N''-methoxy-N'',N'''-bis-(2-chloro-benzenesulphonyl)-guanidine of melting point 164° C. are obtained.

Example II-3)

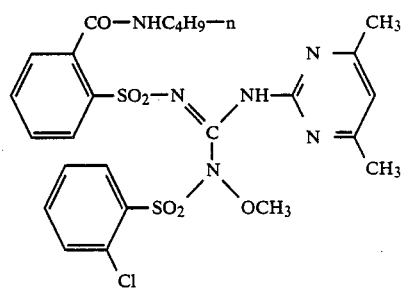

2.5 g (0.012 mole) of 2-chloro-benzenesulphonyl chloride are added to a mixture of 5.0 g (0.011 mole) of N'-(4,6-dimethyl-pyrimidin-2-yl)-N''-methoxy-N'''-(2-butylaminocarbonyl-benzenesulphonyl)-guanidine, 2.0 g (0.016 mole) of 4-dimethylamino-pyridine and 30 ml of acetonitrile. The reaction mixture is heated at the boil under reflux for 3 hours and then concentrated. The residue is taken up in 100 ml of methylene chloride. This solution is washed with 100 ml of 5% strength hydrochloric acid and with 100 ml of water, dried, filtered and concentrated.

1.8 g (30% of theory) of N'-(4,6-dimethyl-pyrimidin-2-yl)-N''-methoxy-N''-(2-chloro-benzenesulphonyl)-N'''-(2-butylaminocarbonyl-benzenesulphonyl)-guanidine are obtained as a crystalline residue of melting point 157° C.

The compounds of the formula (II) listed in Tables 8 and 9 below can be prepared analogously:

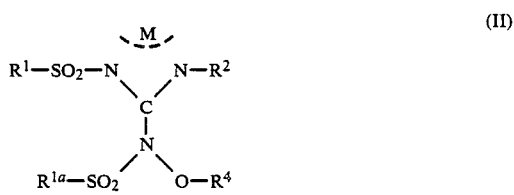

(II)

TABLE 8

| Example No. | R¹ = R¹ᵃ | R² | R⁴ | M | Melting point [°C.] |
|---|---|---|---|---|---|
| (II-4) | 2-COOCH₃-phenyl | 4,6-dimethylpyrimidin-2-yl | CH₃ | H | 165 |
| (II-5) | 2-CH₃-phenyl | 4,6-dimethylpyrimidin-2-yl | CH₃ | H | 129 |
| (II-6) | 2-biphenyl | 4,6-dimethylpyrimidin-2-yl | CH₃ | H | 171 |
| (II-7) | 2-CF₃-phenyl | 4,6-dimethylpyrimidin-2-yl | CH₃ | H | 121 |
| (II-8) | 2-Br-phenyl | 4,6-dimethylpyrimidin-2-yl | CH₃ | H | 147 |
| (II-9) | 2-F-phenyl | 4,6-dimethylpyrimidin-2-yl | CH₃ | H | 166 |
| (II-10) | 2-OCH₃-phenyl | 4,6-dimethylpyrimidin-2-yl | CH₃ | H | 196 |
| (II-11) | 2-OCF₃-phenyl | 4,6-dimethylpyrimidin-2-yl | CH₃ | H | 158 |
| (II-12) | 2-OCHF₂-phenyl | 4,6-dimethylpyrimidin-2-yl | CH₃ | H | 163 |

TABLE 8-continued

| Example No. | R¹ = R¹ᵃ | R² | R⁴ | M | Melting point [°C.] |
|---|---|---|---|---|---|
| (II-13) | 2-SCH₃-phenyl | 4,6-dimethylpyrimidin-2-yl | CH₃ | H | 158 |
| (II-14) | 2-SO₂N(CH₃)₂-phenyl | 4,6-dimethylpyrimidin-2-yl | CH₃ | H | 138 |
| (II-15) | 2-COOC₂H₅-phenyl | 4,6-dimethylpyrimidin-2-yl | CH₃ | H | 106 |
| (II-16) | 2-COOC₄H₉-phenyl | 4,6-dimethylpyrimidin-2-yl | CH₃ | H | 104 |
| (II-17) | 2-COOC₃H₇-phenyl | 4,6-dimethylpyrimidin-2-yl | CH₃ | H | 134 |
| (II-18) | 2-SO₂CH₃-phenyl | 4,6-dimethylpyrimidin-2-yl | CH₃ | H | 155 |
| (II-19) | 2-SO₂CH₃-phenyl | 4,6-dimethylpyrimidin-2-yl | C₈H₁₇ | H | 164 |
| (II-20) | 2-COOCH₃-phenyl | 4,6-dimethylpyrimidin-2-yl | CH₃ | H | 154 |
| (II-21) | 2-Cl-phenyl | 4,6-dimethylpyrimidin-2-yl | CH₃ | H | 140–141 |
| (II-22) | 2-OCF₃-phenyl | 4,6-dimethylpyrimidin-2-yl | CH₃ | H | 170 |

TABLE 8-continued
| Example No. | R¹ = R¹ᵃ | R² | R⁴ | M | Melting point [°C.] |
|---|---|---|---|---|---|
| (II-23) | 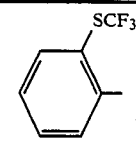 | 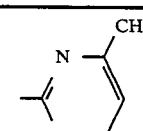 | CH₃ | H | 118 |
| (II-24) | 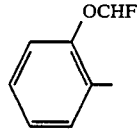 | 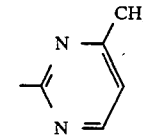 | CH₃ | H | 166–167 |
| (II-25) | 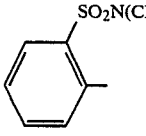 | 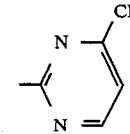 | CH₃ | H | |
| (II-26) | 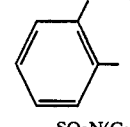 | 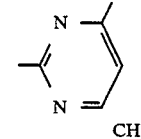 | CH₃ | H | 158–159 |
| (II-27) | 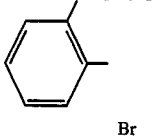 | 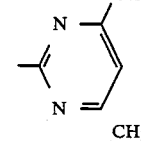 | CH₃ | H | 137–138 |
| (II-28) | 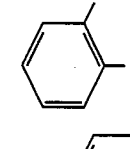 | 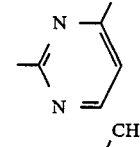 | CH₃ | H | 162–163 |
| (II-29) | 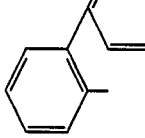 | 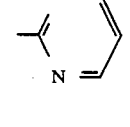 | CH₃ | H | |
| (II-30) | 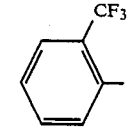 | 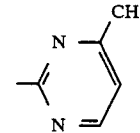 | CH₃ | H | |
| (II-31) | 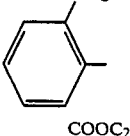 | 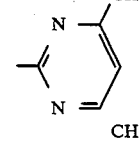 | CH₃ | H | |
| (II-32) | 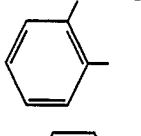 | 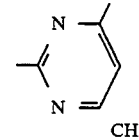 | CH₃ | H | |
| (II-33) | 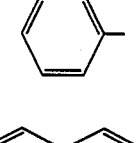 | 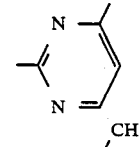 | CH₃ | H | 160 |
| (II-34) | 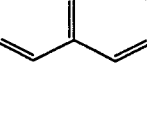 | 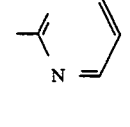 | CH₃ | H | 107 |

TABLE 8-continued

| Example No. | R¹ = R¹ᵃ | R² | R⁴ | M | Melting point [°C.] |
|---|---|---|---|---|---|
| (II-35) | 2-(COOCH₃)benzyl | 4-CH₃, 6-CH=, pyrimidin-2-yl | CH₃ | H | |
| (II-36) | 2-(COOCH₃)phenyl | 4,6-di-OCH₃-pyrimidin-2-yl | CH₃ | H | 149 |
| (II-37) | 2-Cl-phenyl | 4,6-di-OCH₃-pyrimidin-2-yl | CH₃ | H | 164–165 |
| (II-38) | 2-(COOC₂H₅)phenyl | 4,6-di-OCH₃-pyrimidin-2-yl | CH₃ | H | |
| (II-39) | 2-(COOC₃H₇)phenyl | 4,6-di-OCH₃-pyrimidin-2-yl | CH₃ | H | |
| (II-40) | 2-biphenyl | 4,6-di-OCH₃-pyrimidin-2-yl | CH₃ | H | |
| (II-41) | 2-(SO₂N(CH₃)₂)phenyl | 4,6-di-OCH₃-pyrimidin-2-yl | CH₃ | H | 177 |
| (II-42) | 2-(SO₂N(C₂H₅)₂)phenyl | 4,6-di-OCH₃-pyrimidin-2-yl | CH₃ | H | |
| (II-43) | 2-(SO₂N(CH₃)(OCH₃))phenyl | 4,6-di-OCH₃-pyrimidin-2-yl | CH₃ | H | |
| (II-44) | 2-(OCHF₂)phenyl | 4,6-di-OCH₃-pyrimidin-2-yl | CH₃ | H | 136 |

TABLE 8-continued

| Example No. | R¹ = R¹ᵃ | R² | R⁴ | M | Melting point [°C.] |
|---|---|---|---|---|---|
| (II-45) | 2-SCHF₂-phenyl | 4,6-bis(OCH₃)-2-pyrimidinyl | CH₃ | H | |
| (II-46) | 2-OCF₃-phenyl | 4,6-bis(OCH₃)-2-pyrimidinyl | CH₃ | H | 134 |
| (II-47) | 2-SCF₃-phenyl | 4,6-bis(OCH₃)-2-pyrimidinyl | CH₃ | H | |
| (II-48) | 2-Br-phenyl | 4,6-bis(OCH₃)-2-pyrimidinyl | CH₃ | H | |
| (II-49) | 2-SCH₃-phenyl | 4,6-bis(OCH₃)-2-pyrimidinyl | CH₃ | H | |
| (II-50) | 2-SCH₃-phenyl | 4,6-bis(OCH₃)-2-pyrimidinyl | CH₃ | H | 178 (decomp.) |
| (II-51) | 2-Cl-phenyl | 4,6-bis(OCH₃)-2-(CH₃)-pyrimidinyl | CH₃ | H | 172 |
| (II-52) | 2-Br-phenyl | 4,6-bis(OCH₃)-2-(CH₃)-pyrimidinyl | CH₃ | H | 174 |
| (II-53) | 2-OCHF₂-phenyl | 4,6-bis(OCH₃)-2-(CH₃)-pyrimidinyl | CH₃ | H | |
| (II-54) | 2-OCF₃-phenyl | 4,6-bis(OCH₃)-2-(CH₃)-pyrimidinyl | CH₃ | H | 194 |

TABLE 8-continued

| Example No. | $R^1 = R^{1a}$ | $R^2$ | $R^4$ | M | Melting point [°C.] |
|---|---|---|---|---|---|
| (II-55) | 2-(SCHF$_2$)-C$_6$H$_4$ | 4-OCH$_3$-6-CH$_3$-pyrimidin-2-yl | CH$_3$ | H | |
| (II-56) | 2-(SO$_2$N(CH$_3$)$_2$)-C$_6$H$_4$ | 4-OCH$_3$-6-CH$_3$-pyrimidin-2-yl | CH$_3$ | H | 141 |
| (II-57) | 2-(COOCH$_3$)-C$_6$H$_4$ | 4-OCH$_3$-6-CH$_3$-pyrimidin-2-yl | CH$_3$ | H | 152 |
| (II-58) | 2-(COOC$_2$H$_5$)-C$_6$H$_4$ | 4-OCH$_3$-6-CH$_3$-pyrimidin-2-yl | CH$_3$ | H | |
| (II-59) | 2-(COOC$_3$H$_7$(—n))-C$_6$H$_4$ | 4-OCH$_3$-6-CH$_3$-pyrimidin-2-yl | CH$_3$ | H | |
| (II-60) | 2-(COOC$_3$H$_7$(—i))-C$_6$H$_4$ | 4-OCH$_3$-6-CH$_3$-pyrimidin-2-yl | CH$_3$ | H | $n_D^{20} = 1.5391$ |
| (II-61) | 2-(COOC$_4$H$_9$(—n))-C$_6$H$_4$ | 4-OCH$_3$-6-CH$_3$-pyrimidin-2-yl | CH$_3$ | H | |
| (II-62) | 2-biphenylyl | 4-OCH$_3$-6-CH$_3$-pyrimidin-2-yl | CH$_3$ | H | |
| (II-63) | 2-(CF$_3$)-C$_6$H$_4$ | 4-OCH$_3$-6-CH$_3$-pyrimidin-2-yl | CH$_3$ | H | 165 |

TABLE 8-continued

| Example No. | R¹ = R¹ᵃ | R² | R⁴ | M | Melting point [°C.] |
|---|---|---|---|---|---|
| (II-64) | 2-CH₃-phenyl | 4-OCH₃-6-CH₃-pyrimidin-2-yl | CH₃ | H | |
| (II-65) | 2-F-phenyl | 4-OCH₃-6-CH₃-pyrimidin-2-yl | CH₃ | H | 174 |
| (II-66) | 2-SO₂CH₃-phenyl | 4-OCH₃-6-CH₃-pyrimidin-2-yl | CH₃ | H | |
| (II-67) | 2-SO₂N(CH₃)(OCH₃)-phenyl | 4-OCH₃-6-CH₃-pyrimidin-2-yl | CH₃ | H | |
| (II-68) | 2-CON(CH₃)(OCH₃)-phenyl | 4-OCH₃-6-CH₃-pyrimidin-2-yl | CH₃ | H | |
| (II-69) | 2-CON(CH₃)₂-phenyl | 4-OCH₃-6-CH₃-pyrimidin-2-yl | CH₃ | H | |
| (II-70) | 2-COOCH₃-phenyl | 4-OCHF₂-6-CH₃-pyrimidin-2-yl | CH₃ | H | |
| (II-71) | 2-SO₂N(CH₃)₂-phenyl | 4-OCHF₂-6-CH₃-pyrimidin-2-yl | CH₃ | H | |
| (II-72) | 2-OCF₃-phenyl | 4-OCHF₂-6-CH₃-pyrimidin-2-yl | CH₃ | H | |
| (II-73) | 2-OCHF₂-phenyl | 4-OCHF₂-6-CH₃-pyrimidin-2-yl | CH₃ | H | |

TABLE 8-continued

| Example No. | $R^1 = R^{1a}$ | $R^2$ | $R^4$ | M | Melting point [°C.] |
|---|---|---|---|---|---|
| (II-74) | 2-Cl-phenyl | 4-OCHF₂-6-CH₃-pyrimidin-2-yl | CH₃ | H | |
| (II-75) | 2-Br-phenyl | 4-OCHF₂-6-CH₃-pyrimidin-2-yl | CH₃ | H | |
| (II-76) | 2-Cl-phenyl | 4,6-di-CH₃-1,3,5-triazin-2-yl | CH₃ | H | |
| (II-77) | 2-Br-phenyl | 4,6-di-CH₃-1,3,5-triazin-2-yl | CH₃ | H | |
| (II-78) | 2-OCF₃-phenyl | 4,6-di-CH₃-1,3,5-triazin-2-yl | CH₃ | H | |
| (II-79) | 2-OCHF₂-phenyl | 4,6-di-CH₃-1,3,5-triazin-2-yl | CH₃ | H | |
| (II-80) | 2-SCHF₂-phenyl | 4,6-di-CH₃-1,3,5-triazin-2-yl | CH₃ | H | |
| (II-81) | 2-SCF₃-phenyl | 4,6-di-CH₃-1,3,5-triazin-2-yl | CH₃ | H | |
| (II-82) | 2-SCH₃-phenyl | 4,6-di-CH₃-1,3,5-triazin-2-yl | CH₃ | H | |
| (II-83) | 2-SO₂CH₃-phenyl | 4,6-di-CH₃-1,3,5-triazin-2-yl | CH₃ | H | |

TABLE 8-continued

| Example No. | R¹ = R¹ᵃ | R² | R⁴ | M | Melting point [°C.] |
|---|---|---|---|---|---|
| (II-84) | 2-CF₃-phenyl | 4,6-bis(CH₃)-1,3,5-triazin-2-yl | CH₃ | H | |
| (II-85) | 2-F-phenyl | 4-OCH₃-6-CH₃-1,3,5-triazin-2-yl | CH₃ | H | |
| (II-86) | 2-CF₃-phenyl | 4-OCH₃-6-CH₃-1,3,5-triazin-2-yl | CH₃ | H | |
| (II-87) | 2-OCH₃-phenyl | 4-OCH₃-6-CH₃-1,3,5-triazin-2-yl | CH₃ | H | |
| (II-88) | 2,5-diCl-phenyl | 4-OCH₃-6-CH₃-1,3,5-triazin-2-yl | CH₃ | H | |
| (II-89) | 2-CH₃-phenyl | 4-OCH₃-6-CH₃-1,3,5-triazin-2-yl | CH₃ | H | |
| (II-90) | 2-CON(CH₃)₂-phenyl | 4-OCH₃-6-CH₃-1,3,5-triazin-2-yl | CH₃ | H | |
| (II-91) | 2-SO₂N(CH₃)₂-phenyl | 4-OCH₃-6-CH₃-1,3,5-triazin-2-yl | CH₃ | H | |
| (II-92) | 2-OCF₃-phenyl | 4-OCH₃-6-CH₃-1,3,5-triazin-2-yl | CH₃ | H | |
| (II-93) | 2-SCF₃-phenyl | 4-OCH₃-6-CH₃-1,3,5-triazin-2-yl | CH₃ | H . | |

TABLE 8-continued

| Example No. | R¹ = R¹ᵃ | R² | R⁴ | M | Melting point [°C.] |
|---|---|---|---|---|---|
| (II-94) | 2-OCHF₂-phenyl | triazinyl with OCH₃, CH₃ | CH₃ | H | |
| (II-95) | 2-SCHF₂-phenyl | triazinyl with OCH₃, CH₃ | CH₃ | H | |
| (II-96) | 2-SO₂CH₃-phenyl | triazinyl with OCH₃, CH₃ | CH₃ | H | |
| (II-97) | 2-Br-phenyl | triazinyl with OCH₃, CH₃ | CH₃ | H | |
| (II-98) | 2-CN-phenyl | pyrimidinyl with OCH₃, CH₃ | CH₃ | H | |
| (II-99) | 2-SCH₃-phenyl | triazinyl with OCH₃, CH₃ | CH₃ | H | |
| (II-100) | 2-SO₂N(C₂H₅)-phenyl | triazinyl with OCH₃, CH₃ | CH₃ | H | |
| (II-101) | 2-Cl-phenyl | triazinyl with OCH₃, OCH₃ | CH₃ | H | |
| (II-102) | 2-Br-phenyl | triazinyl with OCH₃, OCH₃ | CH₃ | H | |
| (II-103) | 2-CH₃-phenyl | triazinyl with OCH₃, OCH₃ | CH₃ | H | |

TABLE 8-continued

| Example No. | R¹ = R¹ᵃ | R² | R⁴ | M | Melting point [°C.] |
|---|---|---|---|---|---|
| (II-104) | 2-F-C₆H₄- | -C(CH₃)=N-C(OCH₃)=N-C(OCH₃)=N- (triazine with two OCH₃) | CH₃ | H | |
| (II-105) | 2-OCF₃-C₆H₄- | (same triazine) | CH₃ | H | |
| (II-106) | 2-SCF₃-C₆H₄- | (same triazine) | CH₃ | H | |
| (II-107) | 2-OCHF₂-C₆H₄- | (same triazine) | CH₃ | H | |
| (II-108) | 2-SCHF₂-C₆H₄- | (same triazine) | CH₃ | H | |
| (II-109) | 2-SO₂CH₃-C₆H₄- | (same triazine) | CH₃ | H | |
| (II-110) | 2-SCH₃-C₆H₄- | (same triazine) | CH₃ | H | |
| (II-111) | 2-SO₂N(CH₃)₂-C₆H₄- | (same triazine) | CH₃ | H | |
| (II-112) | 2-SO₂N(CH₃)(OCH₃)-C₆H₄- | (same triazine) | CH₃ | H | |

TABLE 8-continued

| Example No. | $R^1 = R^{1a}$ | $R^2$ | $R^4$ | M | Melting point [°C.] |
|---|---|---|---|---|---|
| (II-113) | biphenyl-2-yl | $\underset{N}{\overset{OCH_3}{\underset{\|}{C}}}\!-\!N\!=\!\underset{OCH_3}{\overset{\|}{C}}$ (methyl, N(OCH$_3$), N=C(OCH$_3$)) | $CH_3$ | H | |
| (II-114) | 2-CF$_3$-phenyl | N(OCH$_3$), N=C(OCH$_3$) | $CH_3$ | H | |
| (II-115) | 2-SO$_2$N(C$_2$H$_5$)$_2$-phenyl | N(OCH$_3$), N=C(OCH$_3$) | $CH_3$ | H | |
| (II-116) | 2-phenoxyphenyl | N(OCH$_3$), N=C(OCH$_3$) | $CH_3$ | H | |
| (II-117) | 2-Br-phenyl | N(OCH$_3$), N=C(C$_2$H$_5$) | $CH_3$ | H | |
| (II-118) | 2-SO$_2$N(CH$_3$)$_2$-phenyl | N(OCH$_3$), N=C(C$_2$H$_5$) | $CH_3$ | H | |
| (II-119) | 2-Cl-phenyl | N(OCH$_3$), N=C(C$_2$H$_5$) | $CH_3$ | H | amorphous |
| (II-120) | 2-OCF$_3$-phenyl | N(OCH$_3$), N=C(C$_2$H$_5$) | $CH_3$ | H | |
| (II-121) | 2-OCHF$_2$-phenyl | N(OCH$_3$), N=C(C$_2$H$_5$) | $CH_3$ | H | |

TABLE 8-continued

| Example No. | R¹ = R¹ᵃ | R² | R⁴ | M | Melting point [°C.] |
|---|---|---|---|---|---|
| (II-122) | 2-(SCH₃)-C₆H₄- | -C(OCH₃)=N-CH=N-C(C₂H₅)=N- | CH₃ | H | |
| (II-123) | 2-(COOCH₃)-C₆H₄- | -C(OCH₃)=N-CH=N-C(N(C₂H₅)₂)=N- | CH₃ | H | amorphous |
| (II-124) | 2-(SO₂CH₃)-C₆H₄- | -C(OCH₃)=N-CH=N-C(C₂H₅)=N- | CH₃ | H | |
| (II-125) | 2-biphenyl | -C(OCH₃)=N-CH=N-C(C₂H₅)=N- | CH₃ | H | |
| (II-126) | 2-Cl-C₆H₄- | -C(N(CH₃)₂)=N-CH=N-C(CH₃)=N- | CH₃ | H | 203 (decomp.) |
| (II-127) | 2-CH₃-C₆H₄- | -C(N(CH₃)₂)=N-CH=N-C(CH₃)=N- | CH₃ | H | |
| (II-128) | 2-(SO₂N(CH₃)₂)-C₆H₄- | -C(N(CH₃)₂)=N-CH=N-C(CH₃)=N- | CH₃ | H | |
| (II-129) | 2-(OCF₃)-C₆H₄- | -C(N(CH₃)₂)=N-CH=N-C(CH₃)=N- | CH₃ | H | |
| (II-130) | 2-(SCH₃)-C₆H₄- | -C(N(CH₃)₂)=N-CH=N-C(CH₃)=N- | CH₃ | H | |

TABLE 8-continued

| Example No. | $R^1 = R^{1a}$ | $R^2$ | $R^4$ | M | Melting point [°C.] |
|---|---|---|---|---|---|
| (II-131) | 2-Cl-phenyl | C(=N-)(NHC$_2$H$_5$)-N=C(SCH$_3$)- (amidine/triazine) | CH$_3$ | H | amorphous |
| (II-132) | 2-Br-phenyl | C(=N-)(N(CH$_3$)$_2$)-N=C(CH$_3$)- | CH$_3$ | H | |
| (II-133) | 2-COOCH$_3$-phenyl | C(=N-)(NHC$_2$H$_5$)-N=C(SCH$_3$)- | CH$_3$ | H | amorphous |
| (II-134) | 2-CF$_3$-phenyl | C(=N-)(N(CH$_3$)$_2$)-N=C(CH$_3$)- | CH$_3$ | H | |
| (II-135) | 2-SO$_2$CH$_3$-phenyl | C(=N-)(N(CH$_3$)$_2$)-N=CH- with CH$_3$ | CH$_3$ | H | |
| (II-136) | 2-Cl-phenyl | N=N, C(CH$_3$)=C(CH$_3$)- (pyridazine) | CH$_3$ | H | 179 |
| (II-137) | 2-OCF$_3$-phenyl | N=N, C(CH$_3$)=C(CH$_3$)- | CH$_3$ | H | |
| (II-138) | 2-OCHF$_2$-phenyl | N=N, C(CH$_3$)=C(CH$_3$)- | CH$_3$ | H | |
| (II-139) | 2-Br-phenyl | N=N, C(CH$_3$)=C(CH$_3$)- | CH$_3$ | H | |
| (II-140) | 2-SCH$_3$-phenyl | N=N, C(CH$_3$)=C(CH$_3$)- | CH$_3$ | H | |

TABLE 8-continued

| Example No. | $R^1 = R^{1a}$ | $R^2$ | $R^4$ | M | Melting point [°C.] |
|---|---|---|---|---|---|
| (II-141) | 2-Cl-C$_6$H$_4$- | 3-methyl-pyridazin-6-yl (CH$_3$ on pyridazine) | CH$_3$ | H | |
| (II-142) | 2-OCF$_3$-C$_6$H$_4$- | 3-methyl-pyridazin-6-yl | CH$_3$ | H | |
| (II-143) | 2-OCHF$_2$-C$_6$H$_4$- | 3-methyl-pyridazin-6-yl | CH$_3$ | H | |
| (II-144) | 2-Br-C$_6$H$_4$- | 3-methyl-pyridazin-6-yl | CH$_3$ | H | |
| (II-145) | 2-SCH$_3$-C$_6$H$_4$- | 3-methyl-pyridazin-6-yl | CH$_3$ | H | |
| (II-146) | 2-Cl-C$_6$H$_4$- | 2,6-dimethyl-pyrazin-3-yl | CH$_3$ | H | |
| (II-147) | 2-OCF$_3$-C$_6$H$_4$- | 2,6-dimethyl-pyrazin-3-yl | CH$_3$ | H | |
| (II-148) | 2-OCHF$_2$-C$_6$H$_4$- | 2,6-dimethyl-pyrazin-3-yl | CH$_3$ | H | |
| (II-149) | 2-Br-C$_6$H$_4$- | 2,6-dimethyl-pyrazin-3-yl | CH$_3$ | H | |
| (II-150) | 2-SCH$_3$-C$_6$H$_4$- | 2,6-dimethyl-pyrazin-3-yl | CH$_3$ | H | |

TABLE 8-continued

| Example No. | R¹ = R¹ᵃ | R² | R⁴ | M | Melting point [°C.] |
|---|---|---|---|---|---|
| (II-151) | 2-Cl-phenyl | 2,6-bis(OCH₃)-pyrimidin-4-yl | CH₃ | H | |
| (II-152) | 2-OCF₃-phenyl | 2,6-bis(OCH₃)-pyrimidin-4-yl | CH₃ | H | |
| (II-153) | 2-Br-phenyl | 2,6-bis(OCH₃)-pyrimidin-4-yl | CH₃ | H | |
| (II-154) | 2-CF₃-phenyl | 2,6-bis(OCH₃)-pyrimidin-4-yl | CH₃ | H | |
| (II-155) | 2-NO₂-phenyl | 2,4,6-tris(CH₃)-pyrimidin-... | CH₃ | H | 65 |
| (II-156) | 2-OCF₃-phenyl | 2,4,6-tris(CH₃)-pyrimidin-... | C₂H₅ | H | 163 |
| (II-157) | 2,5-diBr-phenyl | 2,4,6-tris(CH₃)-pyrimidin-... | CH₃ | H | 115 |
| (II-158) | 2-OCHF₂-phenyl | 2,4,6-tris(CH₃)-pyrimidin-... | C₂H₅ | H | 159–160 |
| (II-159) | 2-SCH₃-phenyl | 2,4,6-tris(CH₃)-pyrimidin-... | CH₃ | H | 182–183 |
| (II-160) | 2-SO₂N(CH₃)₂-phenyl | 2,4,6-tris(CH₃)-pyrimidin-... | C₄H₉(—s) | H | 149 |

TABLE 8-continued

| Example No. | R¹ = R¹ᵃ | R² | R⁴ | M | Melting point [°C.] |
|---|---|---|---|---|---|
| (II-161) | 2-(SO₂N(C₂H₅)₂)-phenyl | 4,6-dimethylpyrimidin-2-yl | CH₃ | H | 141 |
| (II-162) | 2-Cl-phenyl | 4,6-dimethylpyrimidin-2-yl | C₃H₇(—n) | H | 160 |
| (II-163) | 2-(COOC₃H₇(—i))-phenyl | 4,6-dimethylpyrimidin-2-yl | CH₃ | H | 65 |
| (II-164) | 2-Cl-phenyl | 4,6-dimethylpyrimidin-2-yl | C₃H₇(—i) | H | 185 |
| (II-165) | 2-Cl-phenyl | 4-OCH₃-6-methyl-2-N(C₂H₅)₂-1,3,5-triazin-... | CH₃ | H | 133 |
| (II-166) | 2-(SC₃H₇(—i))-phenyl | 4,6-dimethylpyrimidin-2-yl | CH₃ | H | amorphous |
| (II-167) | 2-(COOCH₂CH₂Cl)-phenyl | 4,6-dimethylpyrimidin-2-yl | CH₃ | H | 136 |
| (II-168) | 4-Cl-phenyl | 4,6-dimethylpyrimidin-2-yl | CH₃ | H | 148 |
| (II-169) | 4-F-phenyl | 4,6-dimethylpyrimidin-2-yl | CH₃ | H | 135 |
| (II-170) | 2-(COOCH₃)-phenyl | 4-C₂H₅-6-methylpyrimidin-2-yl | CH₃ | H | 141 |

TABLE 8-continued

| Example No. | R¹ = R¹ᵃ | R² | R⁴ | M | Melting point [°C.] |
|---|---|---|---|---|---|
| (II-171) | 2-COOCH₃-phenyl | 4-CH₃, 2-pyrimidinyl | C₂H₅ | H | 135 |
| (II-172) | 2-CF₃-phenyl | 4,6-(CH₃)₂, 2-pyrimidinyl | C₂H₅ | H | 148 |
| (II-173) | 2-F-phenyl | 4,6-(CH₃)₂, 2-pyrimidinyl | C₂H₅ | H | 140 |
| (II-174) | 2-Br-phenyl | 4,6-(CH₃)₂, 2-pyrimidinyl | C₂H₅ | H | 166 |
| (II-175) | 2-COOCH₃-phenyl | 4-OCH₃, 6-Cl, 2-pyrimidinyl | CH₃ | H | 159 |
| (II-176) | 2-COOCH₃-phenyl | 2-pyrimidinyl | CH₃ | H | 144–147 |
| (II-177) | 2-COOCH₂CH₂Cl-phenyl | 4,6-(CH₃)₂, 2-pyrimidinyl | CH₂CH=CH₂ | H | 128 |
| (II-178) | 2-COOCH₂CH₂Cl-phenyl | 4,6-(CH₃)₂, 2-pyrimidinyl | C₂H₅ | H | 142 |
| (II-179) | 2-COOCH₂CH₂Cl-phenyl | 4,6-(CH₃)₂, 2-pyrimidinyl | C₃H₇(—n) | H | 104–106 |
| (II-180) | 2-Br-phenyl | 4,6-(OCH₃)₂, 2-pyrimidinyl | OCH₃ | H | 109 |

TABLE 8-continued

| Example No. | R¹ = R¹ᵃ | R² | R⁴ | M | Melting point [°C.] |
|---|---|---|---|---|---|
| (II-181) | 2-(COOCH₂CH₂Cl)-phenyl | 4-OCH₃-6-CH₃-pyrimidin-2-yl | OCH₃ | H | 138 |
| (II-182) | 2-Br-phenyl | 4-OCH₃-6-CH₃-pyrimidin-2-yl | OC₂H₅ | H | 164 |

TABLE 9

| Example No. | R¹ | R¹ᵃ | R² | R⁴ | M | Melting point [°C.] |
|---|---|---|---|---|---|---|
| (1-II) | 2-Cl-phenyl | 2-OCF₃-phenyl | 4,6-(CH₃)₂-pyrimidin-2-yl | CH₃ | H | 160 |
| (2-II) | 4-CH₃-phenyl | 2-Cl-phenyl | 4,6-(CH₃)₂-pyrimidin-2-yl | CH₃ | H | 85 |
| (3-II) | 4-CH₃-phenyl | 2-Cl-phenyl | 4,6-(CH₃)₂-pyrimidin-2-yl | CH₂-phenyl | H | 168 |
| (4-II) | 3-Cl-phenyl | 2-COOCH₃-phenyl | 4,6-(CH₃)₂-pyrimidin-2-yl | CH₃ | H | 158 |
| (5-II) | 4-CH₃-phenyl | 2-COOCH₃-phenyl | 4,6-(CH₃)₂-pyrimidin-2-yl | CH₃ | H | 150 |
| (6-II) | 2-Cl-phenyl | 2-COOCH₃-phenyl | 4,6-(CH₃)₂-pyrimidin-2-yl | CH₃ | H | 149 |

TABLE 9-continued

| Example No. | R¹ | R¹ᵃ | R² | R⁴ | M | Melting point [°C.] |
|---|---|---|---|---|---|---|
| (7-II) | 4-Cl-phenyl | 2-(COOCH₃)-phenyl | -N=C(CH₃)-CH=C(CH₃)-N= | CH₃ | H | 145 |
| (8-II) | 4-Br-phenyl | 2-(COOCH₃)-phenyl | -N=C(CH₃)-CH=C(CH₃)-N= | CH₃ | H | 153 |
| (9-II) | 4-F-phenyl | 2-(COOCH₃)-phenyl | -N=C(CH₃)-CH=C(CH₃)-N= | CH₃ | H | 155 |
| (10-II) | 2-Cl-phenyl | 2-(COOCH₃)-phenyl | -N=C(CH₃)-CH=C(CH₃)-N= | CH₃ | H | 160 |
| (11-II) | 2-(SCH₃)-phenyl | 2-Cl-phenyl | -N=C(CH₃)-CH=C(CH₃)-N= | -CH₂-phenyl | H | 156 |
| (12-II) | 2-Cl-phenyl | 2-(SO₂N(CH₃)₂)-phenyl | -N=C(CH₃)-CH=C(CH₃)-N= | CH₂CH(CH₃)₂ | H | 156 |
| (13-II) | 2-(CONHOCH₃)-phenyl | 2-Cl-phenyl | -N=C(CH₃)-CH=C(CH₃)-N= | CH₃ | H | amorphous |
| (14-II) | 3,5-diCl-phenyl | 2-(OCHF₂)-phenyl | -N=C(CH₃)-CH=C(CH₃)-N= | CH₃ | H | 171 |

TABLE 9-continued

| Example No. | R¹ | R¹ᵃ | R² | R⁴ | M | Melting point [°C.] |
|---|---|---|---|---|---|---|
| (15-II) | 2-Cl-phenyl | 2-COOCH₃-phenyl | 4,6-dimethylpyrimidin-2-yl | CH₂CH(CH₃)₂ | H | 156 |
| (16-II) | 2-COOCH₃-phenyl | 2-Cl-phenyl | 4,6-dimethylpyrimidin-2-yl | CH₂CH(CH₃)₂ | H | 119 |
| (17-II) | 2-CN-phenyl | 2-COOCH₃-phenyl | 4,6-dimethylpyrimidin-2-yl | CH₃ | H | 170 |
| (18-II) | 2-COOCH₃-phenyl | 2-SO₂N(CH₃)₂-phenyl | 4,6-dimethylpyrimidin-2-yl | CH₂CH(CH₃)₂ | H | 157 |
| (19-II) | 2-Cl-phenyl | 2-COOCH₃-phenyl | 4,6-dimethylpyrimidin-2-yl | CH₂COOC₂H₅ | H | 103–104 |
| (20-II) | 2-COOCH₃-phenyl | 2-Cl-phenyl | 4,6-dimethylpyrimidin-2-yl | CH₂COOC₂H₅ | H | 142–143 |
| (21-II) | 2-CONH—C₄H₉(—n)-phenyl | 2-Cl-phenyl | 4,6-dimethylpyrimidin-2-yl | —C₈H₁₇(—n) | H | amorphous |
| (22-II) | 2-OCF₃-4-Cl-phenyl | 2-Cl-phenyl | 4,6-dimethylpyrimidin-2-yl | CH₂-phenyl | H | amorphous |

TABLE 9-continued

| Example No. | R[1] | R[1a] | R[2] | R[4] | M | Melting point [°C.] |
|---|---|---|---|---|---|---|
| (23-II) | 2-CONHC₄H₉(—n)-C₆H₄— | 2-Cl-C₆H₄— | 4,6-dimethylpyrimidin-2-yl | CH₃ | H | amorphous |
| (24-II) | 2-Cl-C₆H₄— | 2-OCF₃-C₆H₄— | 4-methyl-6-methoxy-1,3,5-triazin-2-yl | CH₃ | H | 172 |
| (25-II) | 2-Cl-C₆H₄— | 2-COOCH₃-C₆H₄— | 4,6-dimethoxy-1,3,5-triazin-2-yl | CH₃ | H | 105 |
| (26-II) | 2-Cl-C₆H₄— | 4-NO₂-C₆H₄— | 4-methyl-6-methoxy-1,3,5-triazin-2-yl | CH₃ | H | 207 |
| (27-II) | 2-Cl-C₆H₄— | 2-COOCH₃-C₆H₄— | 4-ethyl-6-methoxy-1,3,5-triazin-2-yl | CH₃ | H | amorphous |
| (28-II) | 2-COOCH₃-C₆H₄— | 2-SO₂CH₃-C₆H₄— | 4,6-dimethylpyrimidin-2-yl | CH₃ | H | 173 |
| (29-II) | 2-SCH₃-C₆H₄— | 2-Cl-C₆H₄— | 4-methyl-6-methoxy-1,3,5-triazin-2-yl | CH₃ | H | amorphous |
| (30-II) | 2-SC₃H₇(—i)-C₆H₄— | 2-COOCH₃-C₆H₄— | 4,6-dimethylpyrimidin-2-yl | CH₃ | H | 145 |

TABLE 9-continued

| Example No. | R¹ | R¹ᵃ | R² | R⁴ | M | Melting point [°C.] |
|---|---|---|---|---|---|---|
| (31-II) | 2-Cl-phenyl | 4-CH₃-phenyl | 4,6-dimethylpyrimidin-2-yl | $-C_4H_9(-n)$ | H | amorphous |
| (32-II) | 2-SO₂CH₃-phenyl | 2-Cl-phenyl | 4,6-dimethylpyrimidin-2-yl | $-CH_2$-phenyl | H | 174 |
| (33-II) | 2-COOCH₃-phenyl | 2-Cl-phenyl-CH₂— | 4,6-dimethylpyrimidin-2-yl | $-CH_3$ | H | 77–79 |

PREPARATION OF STARTING SUBSTANCES OF THE FORMULA (IV)

Example (IV-1)

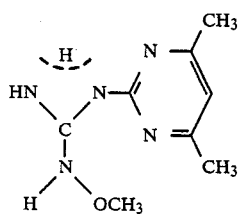

A mixture of 109 g (0.67 mole) of O-methylhydroxylamine hydrochloride, 99 g (0.67 mole) of 2-cyanoamino-4,6-dimethylpyrimidine and 600 ml of ethanol is heated at the boiling point under reflux for 7 hours. The alcohol is then distilled off under a water-pump vacuum, the residue is dissolved in hot water and this solution is added to 100 ml of concentrated ammonia. The product which has crystallised out is filtered off with suction and recrystallised from ethanol.

71.8 g (55% of theory) of N'-(4,6-dimethylpyrimidin-2-yl)-N''-methoxy-guanidine of melting point 134° C. to 136° C. are obtained.

The compounds of the formula (IV) listed in Table 10 below can be prepared analogously:

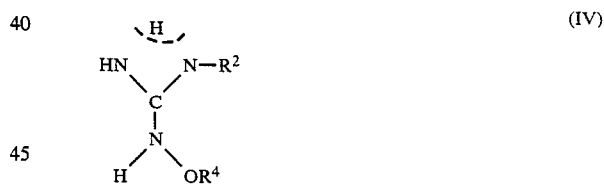

TABLE 10

| Example No. | R⁴ | R² | Melting point [°C.] |
|---|---|---|---|
| (IV-2) | $-CH_2CH(CH_3)_2$ | 4,6-dimethylpyrimidin-2-yl | 78 |
| (IV-3) | $-CH_2CH=CH_2$ | 4,6-dimethylpyrimidin-2-yl | 103 |

TABLE 10-continued

| Example No. | R⁴ | R² | Melting point [°C.] |
|---|---|---|---|
| (IV-4) | —CH(CH₃)₂ | 2-methyl-4,6-dimethylpyrimidinyl (CH₃, N, CH₃) | 84 |
| (IV-5) | —CH₂CH₂—C₆H₅ | 2-methyl-4,6-dimethylpyrimidinyl | $n_D^{24} = 1.5776$ |
| (IV-6) | —CH(CH₃)—CH₂CH₃ | 2-methyl-4,6-dimethylpyrimidinyl | 52 |
| (IV-7) | —C₈H₁₇(—n) | 2-methyl-4,6-dimethylpyrimidinyl | 58 |
| (IV-8) | —CH₂—C₆H₄—Cl (o-) | 2-methyl-4,6-dimethylpyrimidinyl | 102–103 |
| (IV-9) | —CH₂CH₂CH₂Cl | 2-methyl-4,6-dimethylpyrimidinyl | 137 |
| (IV-10) | —C₆H₅ | 2-methyl-4,6-dimethylpyrimidinyl | 192 (decomp.) |
| (IV-11) | —CH₂—COOCH₃ | 2-methyl-4,6-dimethylpyrimidinyl | 148–149 |
| (IV-12) | —CH₂—COOC₂H₅ | 2-methyl-4,6-dimethylpyrimidinyl | 98–99 |

TABLE 10-continued

| Example No. | R⁴ | R² | Melting point [°C.] |
|---|---|---|---|
| (IV-13) | —CH(CH₃)—COOCH₃ | 4,6-dimethylpyrimidin-2-yl | 147–148 |
| (IV-14) | —CH₂—C₆H₄—CH₃ (p) | 4,6-dimethylpyrimidin-2-yl | 85–86 |
| (IV-15) | —CH₂—C₆H₄—F (o) | 4,6-dimethylpyrimidin-2-yl | 114–116 |
| (IV-16) | cyclohexyl | 4,6-dimethylpyrimidin-2-yl | |
| (IV-17) | —CH₂-cyclohexyl | 4,6-dimethylpyrimidin-2-yl | |
| (IV-18) | —CH₂CON(CH₃)₂ | 4,6-dimethylpyrimidin-2-yl | |
| (IV-19) | —CH₂OCH₃ | 4,6-dimethylpyrimidin-2-yl | |
| (IV-20) | —CH₂SCH₃ | 4,6-dimethylpyrimidin-2-yl | |

TABLE 10-continued
| Example No. | R⁴ | R² | Melting point [°C.] |
|---|---|---|---|
| (IV-21) | 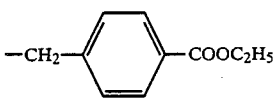 | 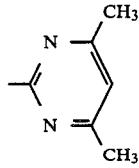 | 138 |
| (IV-22) | —CH₂CF₃ | 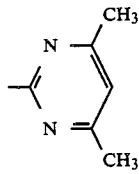 | |
| (IV-23) | 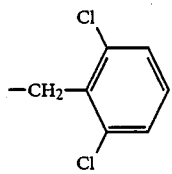 | 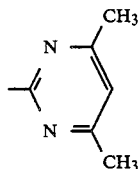 | 140–145 |
| (IV-24) | 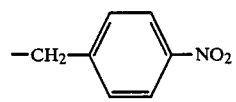 | 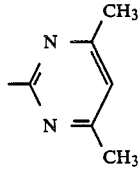 | 170–172 |
| (IV-25) | —C₄H₉(—n) | 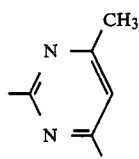 | oil |
| (IV-26) | —C₃H₇(—n) | 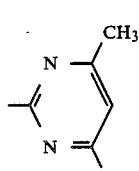 | oil |
| (IV-27) | —CH₂—COOC₃H₇(—i) | 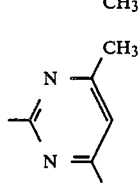 | 112 |
| (IV-28) | 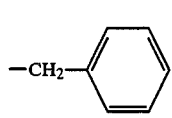 | 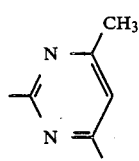 | 102 |
| (IV-29) | —C₂H₅ | 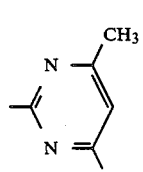 | 88 |

TABLE 10-continued

| Example No. | R⁴ | R² | Melting point [°C.] |
|---|---|---|---|
| (IV-30) | —CH₃ | 2-methyl-4-methylpyrimidin-5-yl | 152 |
| (IV-31) | —CH₃ | 2-methyl-4,6-dimethoxypyrimidin-5-yl | 122 |
| (IV-32) | —CH₃ | 2-methyl-4-methyl-6-methoxypyrimidin-5-yl | 126 |
| (IV-33) | —CH₃ | 4-methyl-6-diethylamino-1,3,5-triazin-2-yl | 112 |
| (IV-34) | —CH₃ | 4-methylthio-6-ethylamino-1,3,5-triazin-2-yl | 117 |
| (IV-35) | —CH₂—CH(CH₃)₂ | 2-methyl-4,6-dimethoxypyrimidin-5-yl | 76 |
| (IV-36) | —CH(CH₃)—CH₂CH₃ | 2-methyl-4,6-dimethoxypyrimidin-5-yl | 68 |
| (IV-37) | —C₂H₅ | 2-methyl-4-methylpyrimidin-5-yl | 95 |
| (IV-38) | —CH₃ | 2-methyl-4-ethylpyrimidin-5-yl | 98 |

TABLE 10-continued

| Example No. | R⁴ | R² | Melting point [°C.] |
|---|---|---|---|
| (IV-39) | —CH₃ | 2-methyl-4-methoxy-6-chloropyrimidin-5-yl | 112 |
| (IV-40) | —CH₃ | 2,6-dimethylpyrimidin-4-yl (with 4-CH₃, 6-CH₃) | 143 |
| (IV-41) | —CH₃ | 2,6-dimethylpyridin-4-yl (with 4-CH₃, 6-CH₃) | 110 |
| (IV-42) | —CH₂—COOC₂H₅ | 2,4-dimethylpyrimidin-6-yl | — |
| (IV-43) | —CH₂—(2-Cl-C₆H₄) | 2,4-dimethylpyrimidin-6-yl | 140 |
| (IV-44) | —CH₂—C₆H₅ | 2,4-dimethylpyrimidin-6-yl | 150 |
| (IV-45) | —CH₂—(2-F-C₆H₄) | 2,4-dimethylpyrimidin-6-yl | 205 |
| (IV-46) | —CH₂—CH=CH₂ | 2,4-dimethylpyrimidin-6-yl | — |
| (IV-47) | —C₄H₉(—n) | 2,4-dimethylpyrimidin-6-yl | — |
| (IV-48) | —C₄H₉(—s) | 2,4-dimethylpyrimidin-6-yl | — |

TABLE 10-continued

| Example No. | R⁴ | R² | Melting point [°C.] |
|---|---|---|---|
| (IV-49) | —CH₂CH₂CH₂Cl | 4-methylpyrimidin-2-yl | ~102 |
| (IV-50) | —CH₃ | 4,6-diethoxypyrimidin-2-yl | |
| (IV-51) | —CH₃ | pyrimidin-2-yl | 107–109 |
| (IV-52) | —CH₂—C₆H₅ | 4-methoxy-6-methylpyrimidin-2-yl | $n_D^{20} = 1.5645$ |
| (IV-53) | —CH₂—C₆H₅ | 4-ethylpyrimidin-2-yl | 112 |
| (IV-54) | —CH₂—C₆H₅ | 4,6-dimethoxypyrimidin-2-yl | 74 |
| (IV-55) | —CH₂—C₆H₅ | 4-methylthio-6-ethylamino-1,3,5-triazin-2-yl (with CH₃) | 122 |
| (IV-56) | —C₈H₁₇(—n) | 4-methyl-6-methoxy-1,3,5-triazin-2-yl | 95 |
| (IV-57) | —CH₂—C₆H₅ | 4-methyl-6-methoxy-1,3,5-triazin-2-yl | 112 |

TABLE 10-continued

| Example No. | R⁴ | R² | Melting point [°C.] |
|---|---|---|---|
| (IV-58) | —CH₃ | 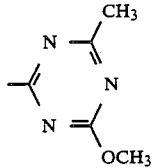 | 126 |
| (IV-59) | —CH₂—C₆H₅ | 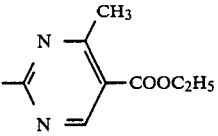 | 130 |

PREPARATION OF THE STARTING SUBSTANCES OF THE FORMULA (XIII)

Example (XIII-1)

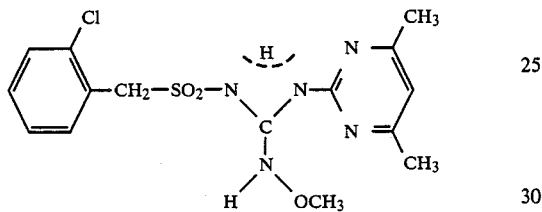

A solution of 16.8 g (0.15 mole) of diazabicyclooctane in 50 ml of methylene chloride is added dropwise with stirring to a mixture of 9.8 g (0.05 mole) of N'-(4,6-dimethyl-pyrimidin-2-yl)-N''-methoxy-guanidine, 28.2 g (0.12 mole) of 2-chlorophenyl-methanesulphonyl chloride and 50 ml of methylene chloride which has been cooled to 0° C. The reaction mixture is stirred for 2 hours at 10° C. and for a further 15 hours at 20° C. Thereafter, 50 ml of 2N hydrochloric acid are added, the mixture is shaken thoroughly and the organic phase is then separated off, washed with water, dried, filtered and concentrated. The oily residue is brought to crystallisation with isopropanol.

3.0 g (12% of theory) of N'-(4,6-dimethyl-pyrimidin-2-yl)-N''-methoxy-N''''-(2-chloro-benzenesulphonyl)-guanidine of melting point 130° C. are obtained.

Example (XIII-2)

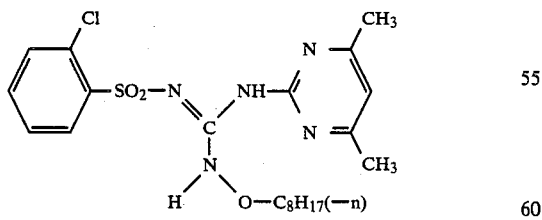

A mixture of 13.8 g (0.025 mole) of N'-(4,6-dimethyl-pyrimidin-2-yl)-N''-methoxy-N''',N''''-bis-(2-chlorobenzenesulphonyl)-guanidine, 3.7 g (0.026 mole) of O-octyl-hydroxylamine and 80 ml of ethanol is heated at the boil under reflux for 15 hours. Thereafter, the mixture is concentrated in a water pump vacuum, and the product is brought to crystallisation by trituration and is isolated by filtration with suction.

3.2 g (27% of theory) of N'-(4,6-dimethyl-pyrimidin-2-yl)-N''-octyloxy-N''''-(2-chloro-benzenesulphonyl)-guanidine of melting point 55° C. are obtained.

Example (XIII-3)

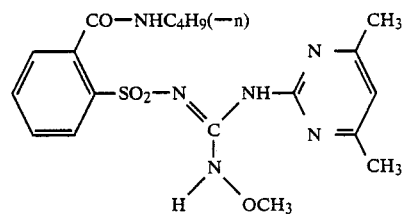

4.0 g (0.025 mole) of butylamine are added at 20° C.-30° C. with stirring to a mixture of 9.1 g (0.025) mole of the compound of the formula below

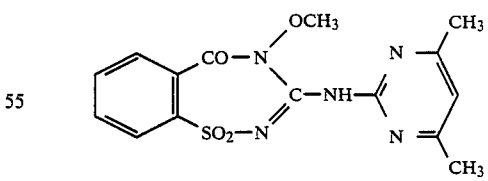

and 60 ml of diethyl ether and 5 ml of dioxane. The reaction mixture is stirred for 15 hours at 20° C., and the crystalline product obtained is isolated by filtration with suction.

8.1 g (75% of theory) of N'-(4,6-dimethyl-pyrimidin-2-yl)-N''-methoxy-N''''-(2-butylaminocarbonyl-benzenesulphonyl)-guanidine of melting point 169° C. are obtained.

Example (XIII-4)

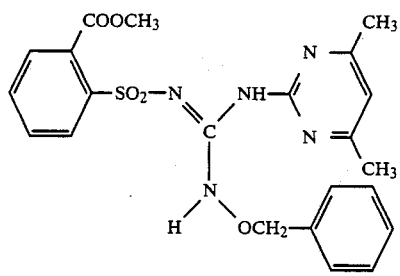

A mixture of 8.8 g (0.02 mole) of the compound of the formula below

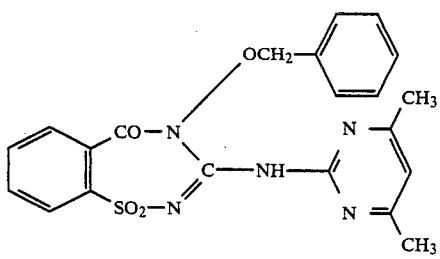

and 2.2 g (0.04 mole) of sodium methylate and 70 ml of methanol is heated at the boil under reflux for 8 hours. After the mixture is cooled to −10° C., it is filtered with suction, the solid is dissolved in 200 ml of water, the solution is filtered and the filtrate is acidified with concentrated hydrochloric acid. The crystalline product obtained is isolated by filtration with suction.

3.2 g (34% of theory) of N'-(4,6-dimethyl-pyrimidin-2-yl)-N''-benzyloxy-N'''-(2-methoxycarbonyl-benzenesulphonyl)-guanidine of melting point 138° C. are obtained.

Example (XIII-5)

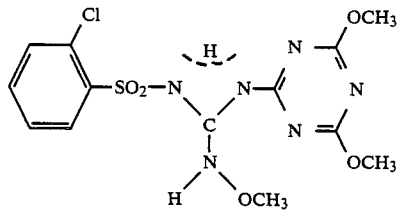

A mixture of 10 g (0.026 mole) of N'-(4,6-dimethoxy-s-triazin-2-yl)-N''-(2-chloro-benzenesulphonyl)-S-methyl-isothiourea, 3.0 g (0.065 mole) of O-methylhydroxylamine and 80 ml of dioxane is stirred for 60 hours at 20° C. Thereafter, the mixture is concentrated, the residue is triturated with ethanol and the crystalline product obtained is isolated by filtration with suction.

5.8 g (57% of theory) of N'-(4,6-dimethoxy-s-triazin-2-yl)-N''-methoxy-N''''-(2-chloro-benzenesulphonyl)-guanidine of melting point 150° C. are obtained.

Example (XIII-6)

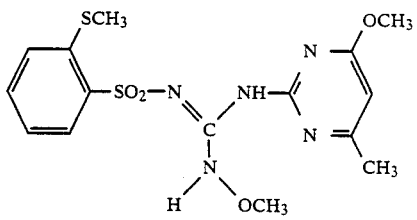

A mixture of 16.0 g (0.14 mole) of N'-(4-methoxy-6-methyl-pyrimidin-2-yl)-N''-(2-methylthio-benzenesulphonyl)-S-methyl-isothiourea, 4.0 g (0.085 mole) of O-methylhydroxylamine and 80 ml of dioxane is stirred for 15 hours at 30° C. to 33° C. Thereafter, the mixture is concentrated, the residue is brought to crystallisation by trituration with ethanol, and the product is isolated by filtration with suction.

8.4 g (53% of theory) of N'-(4-methoxy-6-methyl-pyrimidin-2-yl)-N''-methoxy-N'''-(2-methylthio-benzenesulphonyl)-guanidine of melting point 134° C. are obtained.

The compounds of the formulae (XIIIa) and (XIII) listed in Tables 11 and 12 below can be prepared analogously to Example (XIII-1) to Example (XIII-6):

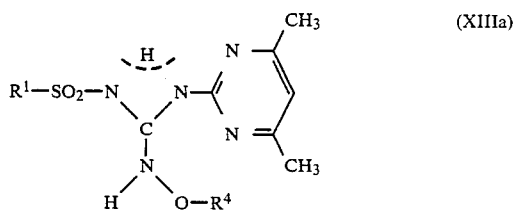 (XIIIa)

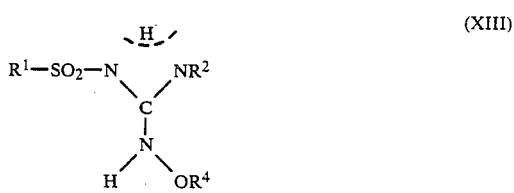 (XIII)

TABLE 11

| | Compounds of the formula (XIIIa) | | |
|---|---|---|---|
| Example No. | $R^1$ | $R^4$ | Melting point [°C.] |
| (XIIIa-1) | 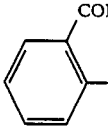CONHOCH$_3$ | —CH$_3$ | 151 |

TABLE 11-continued

Compounds of the formula (XIIIa)

| Example No. | R¹ | R⁴ | Melting point [°C.] |
|---|---|---|---|
| (XIIIa-2) | 2-(CONHCH₃)-phenyl | —CH₃ | 177 |
| (XIIIa-3) | 2-(CONHN(CH₃)₂)-phenyl | —CH₃ | 178 |
| (XIIIa-4) | 2-(CONHC₄H₉(—n))-phenyl | —C₈H₁₇(—n) | amorphous |
| (XIIIa-5) | 2-(COOCH₃)-phenyl | —CH₃ | 132 |
| (XIIIa-6) | 2-Cl-phenyl | —CH₃ | 142 |
| (XIIIa-7) | 2-CH₃-phenyl | —CH₃ | 114 |
| (XIIIa-8) | 2-(COOC₂H₅)-phenyl | —CH₃ | 125 |
| (XIIIa-9) | 2-Cl-phenyl | —CH₂COOCH₃ | 124 |
| (XIIIa-10) | 2-F-phenyl | —CH₃ | 160 |
| (XIIIa-11) | 2-Cl-phenyl | —CH₂—COOC₃H₇(—i) | 112 |
| (XIIIa-12) | 2-Cl-phenyl | —CH(CH₃)—COOC₂H₅ | 128 |

TABLE 11-continued

Compounds of the formula (XIIIa)

| Example No. | R¹ | R⁴ | Melting point [°C.] |
|---|---|---|---|
| (XIIIa-13) | 2-Cl-phenyl | $-\underset{\underset{CH_3}{|}}{CH}-COOCH_3$ | 124 |
| (XIIIa-14) | 2-COOCH₃-phenyl | $-CH_2-COOC_2H_5$ | 138–139 |
| (XIIIa-15) | 2-Cl-phenyl | $-CH_2$-phenyl | 169 |
| (XIIIa-16) | 2-Cl-phenyl | $-C_4H_9(-n)$ | 116 |
| (XIIIa-17) | 2-COOCH₃-phenyl | $-C_8H_{17}(-n)$ | oil |
| (XIIIa-18) | 2-COOCH₃-phenyl | $-C_4H_9(-n)$ | 95 |
| (XIIIa-19) | 2-Br-phenyl | $-CH_3$ | 166 |
| (XIIIa-20) | 4-Cl-3-NO₂-phenyl | $-CH_3$ | 160 |
| (XIIIa-21) | 2-Cl-4-CF₃-phenyl | $-CH_3$ | 134 |
| (XIIIa-22) | 3-Cl-phenyl | $-CH_3$ | |

TABLE 11-continued

Compounds of the formula (XIIIa)

| Example No. | R¹ | R⁴ | Melting point [°C.] |
|---|---|---|---|
| (XIIIa-23) | 2-CN-C₆H₄-CH₂- | —CH₃ | 166–168 |
| (XIIIa-24) | 2-COOCH₃-C₆H₄-CH₂- | —CH₃ | 117–125 |
| (XIIIa-25) | 2-OCF₃-C₆H₄- | —CH₃ | 128 |
| (XIIIa-26) | 2-OCHF₂-C₆H₄- | —CH₃ | 138 |
| (XIIIa-27) | 2-Cl-C₆H₄- | —CH₂—COOC₂H₅ | 109–110 |
| (XIIIa-28) | 2-COOCH₃-C₆H₄- | —CH₂—COOC₃H₇(—i) | 82–83 |
| (XIIIa-29) | 2-COOCH₃-C₆H₄- | —CH(CH₃)—COOCH₃ | 99–100 |
| (XIIIa-30) | 2-COOCH₃-C₆H₄- | —CH₂—COOCH₃ | 101–102 |
| (XIIIa-31) | 2-COOCH₃-C₆H₄- | —CH(CH₃)—COOC₂H₅ | 54–56 |
| (XIIIa-32) | 2-COOCH₃-C₆H₄- | —CH₂—COOH | 138–140 (decomp.) |
| (XIIIa-33) | 2-Cl-C₆H₄- | —C₆H₅ | 146–149 |

TABLE 11-continued

Compounds of the formula (XIIIa)

| Example No. | R¹ | R⁴ | Melting point [°C.] |
|---|---|---|---|
| (XIIIa-34) | 2-(COOCH₃)-C₆H₄– | –C₆H₅ | 143–145 |
| (XIIIa-35) | 2-Cl-C₆H₄– | –CH₂–CH(CH₃)₂ | 105 |
| (XIIIa-36) | 2-Cl-C₆H₄-CH₂– | –CH₂–C₆H₄–COOC₂H₅ (4-) | 118 |
| (XIIIa-37) | 2-Cl-C₆H₄-CH₂– | –CH₂–CH₂–CH₂–Cl | 139–140 |
| (XIIIa-38) | 2-(CONH₂)-C₆H₄– | –CH₃ | 222 |
| (XIIIa-39) | 2-(CONHOC₃H₇(–i))-C₆H₄– | –CH₃ | 178 |
| (XIIIa-40) | 2-(CON(CH₃)₂)-C₆H₄– | –CH₃ | 153 |
| (XIIIa-41) | 2-(CONHC₃H₇(–n))-C₆H₄– | –CH₃ | 138 |
| (XIIIa-42) | 2-Cl-C₆H₄-CH₂– | 2,6-Cl₂-C₆H₃-CH₂– | 156 |
| (XIIIa-43) | 2-(COOCH₃)-C₆H₄– | 2-Cl-C₆H₄-CH₂– | oil |

TABLE 11-continued

Compounds of the formula (XIIIa)

| Example No. | R¹ | R⁴ | Melting point [°C.] |
|---|---|---|---|
| (XIIIa-44) | 2-OCHF$_2$-C$_6$H$_4$- | -CH$_2$-C$_6$H$_5$ | 242 (decomp.) |
| (XIIIa-45) | 2-OCF$_3$-C$_6$H$_4$- | -C$_2$H$_5$ | 115 |
| (XIIIa-46) | 2-OCHF$_2$-C$_6$H$_4$- | -C$_2$H$_5$ | 136 |
| (XIIIa-47) | 2-CON(CH$_3$)$_2$-C$_6$H$_4$- | -C$_2$H$_5$ | ~148 |
| (XIIIa-48) | 2-CONHOC$_4$H$_9$(-n)-C$_6$H$_4$- | -CH$_2$-C$_6$H$_5$ | oil |
| (XIIIa-49) | 2-CONHOCH$_3$-C$_6$H$_4$- | -C$_4$H$_9$(-n) | oil |
| (XIIIa-50) | 2-COOH-C$_6$H$_4$- | -CH$_2$-C$_6$H$_5$ | 85 |
| (XIIIa-51) | 2-COOCH$_3$-C$_6$H$_4$- | -CH$_2$CH$_2$CH$_2$Cl | 111 |
| (XIIIa-52) | 2-SO$_2$NHOCH$_3$-C$_6$H$_4$- | -CH$_2$-C$_6$H$_5$ | 154 |
| (XIIIa-53) | 2-SO$_2$NHOCH$_3$-C$_6$H$_4$- | -CH$_2$-(2-Cl-C$_6$H$_4$) | ~183 |
| (XIIIa-54) | 2-OCF$_3$-C$_6$H$_4$- | -CH$_2$-C$_6$H$_5$ | 141 |

TABLE 11-continued

Compounds of the formula (XIIIa)

| Example No. | R¹ | R⁴ | Melting point [°C.] |
|---|---|---|---|
| (XIIIa-55) | 2-(CH₂Cl)-phenyl | —CH₃ | 101–103 |

TABLE 12

Compounds of the formula (XIII)

| Example No. | R¹ | R² | R⁴ | Melting point [°C.] |
|---|---|---|---|---|
| (XIII-7) | 2-CH₃-phenyl | —N=C(CH₃)—N=C(CH₃)— | —CH₃ | 148 |
| (XIII-8) | 2-Cl-phenyl | —N=C(CH₃)—N=C(CH₃)— | —CH₃ | 135 |
| (XIII-9) | 2-CH₃-phenyl | —N=C(OCH₃)—N=C(OCH₃)— | —CH₃ | 105 |
| (XIII-10) | 2-Cl-phenyl | —N=C(OCH₃)—N=C(OCH₃)— | —CH₃ | |
| (XIII-11) | 2-CH₃-phenyl | —N=C(CH₃)—N=C(OC₂H₅)— | —CH₃ | 144 |
| (XIII-12) | 2-Cl-phenyl | —N=C(OCH₃)—N=C(C₂H₅)— | —CH₃ | 115 |
| (XIII-13) | 2-CH₃-phenyl | —N=C(CH₃)—N=C(CH₃)— | —CH₃ | 132 |

TABLE 12-continued

Compounds of the formula (XIII)

| Example No. | R¹ | R² | R⁴ | Melting point [°C.] |
|---|---|---|---|---|
| (XIII-14) | 2-Cl-phenyl | 4-methyl-6-methoxy-pyrimidin-2-yl | —CH₃ | 138 |
| (XIII-15) | 2-CH₃-phenyl | 4-methyl-6-methoxy-pyrimidin-2-yl | —CH₃ | 108 |
| (XIII-16) | 2-SCH₃-phenyl | 4-methyl-6-methoxy-pyrimidin-2-yl | —CH₃ | 134 |
| (XIII-17) | 2-CH₃-phenyl | 2,6-dimethyl-pyridin-4-yl (2,4-dimethyl-pyridin) | —CH₃ | 91 |
| (XIII-18) | 2-CH₃-phenyl | 4-methyl-6-dimethylamino-1,3,5-triazin-2-yl | —CH₃ | 105 |
| (XIII-19) | 2-Cl-phenyl | 4-methyl-6-methoxy-1,3,5-triazin-2-yl | —CH₃ | 122 |
| (XIII-20) | 2-SCH₃-phenyl | 4-methyl-6-methoxy-1,3,5-triazin-2-yl | —CH₃ | 132 |
| (XIII-21) | 2-SC₃H₇(—i)-phenyl | 4-methyl-6-methoxy-1,3,5-triazin-2-yl | —CH₃ | 164 |

TABLE 12-continued

Compounds of the formula (XIII)

| Example No. | R¹ | R² | R⁴ | Melting point [°C.] |
|---|---|---|---|---|
| (XIII-22) | 2-COOCH₃-phenyl | 4,6-dimethyl-5-chloro-pyrimidin-2-yl | —CH₂CH₂CH₂Cl | 129 |
| (XIII-23) | 2-COOCH₃-phenyl | 4,6-dimethyl-pyrimidin-2-yl | phenyl | 137 |
| (XIII-24) | 2-COOCH₃-phenyl | 4,6-dimethyl-pyrimidin-2-yl | —CH₂—COOC₂H₅ | 91–93 |
| (XIII-25) | 2-OCF₃-phenyl | 4,6-dimethoxy-pyrimidin-2-yl | —CH₃ | 137 |
| (XIII-26) | 2-OCHF₂-phenyl | 4,6-dimethoxy-pyrimidin-2-yl | —CH₃ | 135 |
| (XIII-27) | 2-Cl-phenyl | 4,6-dimethyl-1,3,5-triazin-2-yl | —CH₃ | 122 |
| (XIII-28) | 2-CH₃-phenyl | 5,6-dimethyl-1,2,4-triazin-3-yl | —CH₃ | 119 |
| (XIII-29) | 2-Cl-phenyl | 5,6-dimethyl-1,2,4-triazin-3-yl | —CH₃ | 165 |
| (XIII-30) | 2-OCF₃-phenyl | 4-ethoxy-6-methyl-1,3,5-triazin-2-yl | —CH₂-phenyl | 136 |

PREPARATION OF STARTING SUBSTANCES OF THE FORMULA (XV)

Example (XV-1)

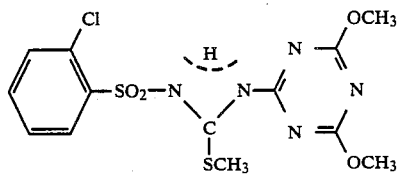

11 g (0.4 mole) of sodium hydride (80% strength) are added in portions to a suspension of 31.2 g (0.2 mole) of 2-amino-4,6-dimethoxy-s-triazine in 200 ml of tetrahydrofuran at 20° C. After the mixture has been stirred for 12 hours, 60 g (0.2 mole) of N-(2-chloro-benzenesulphonyl)-S',S''-dimethyl-iminodithiocarbonic acid ester are added, the reaction temperature increasing to 60° C. The reaction mixture is stirred for 5 hours at 20° C., diluted with 800 ml of water and filtered. After the mixture has been acidified with concentrated hydrochloric acid, the product crystallises, and is isolated by filtration with suction.

42 g (48% of theory) of N'-(4,6-dimethoxy-s-triazin-2-yl)-N''-(2-chloro-benzenesulphonyl)-S-methyl-isothiourea of melting point 176° C. are obtained.

The compounds of the formula (XV) listed in Table 13 below can be prepared analogously to Example (XV-1):

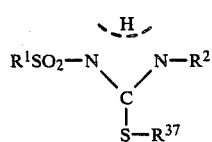

(XV)

TABLE 13

| Example No. | R¹ | R² | R³⁷ | Melting point [°C.] |
|---|---|---|---|---|
| (XV-2) | 2-CH₃-C₆H₄ | 4,6-di-OCH₃-triazin-2-yl | CH₃ | 159 |
| (XV-3) | 2-Cl-C₆H₄ | 4-CH₃-6-N(CH₃)₂-triazin-2-yl | CH₃ | 175 |
| (XV-4) | 2-CH₃-C₆H₄ | 4-CH₃-6-N(CH₃)₂-triazin-2-yl | CH₃ | 157 |
| (XV-5) | 2-Cl-C₆H₄ | 4-CH₃-6-OCH₃-triazin-2-yl | CH₃ | 148 |
| (XV-6) | 2-SCH₃-C₆H₄ | 4-CH₃-6-OCH₃-triazin-2-yl | CH₃ | 167 |
| (XV-7) | 2-SC₃H₇(-i)-C₆H₄ | 4-CH₃-6-OCH₃-triazin-2-yl | CH₃ | 136 |
| (XV-8) | 2-CH₃-C₆H₄ | 4,6-di-cyclopropyl-triazin-2-yl | CH₃ | 170 |
| (XV-9) | 2-CH₃-C₆H₄ | 4-CH₃-6-OC₂H₅-triazin-2-yl | CH₃ | 104 |
| (XV-10) | 2-Cl-C₆H₄ | 4-OCH₃-6-C₂H₅-triazin-2-yl | CH₃ | 132 |
| (XV-11) | 2-CH₃-C₆H₄ | 4,6-di-CH₃-triazin-2-yl | CH₃ | 119 |
| (XV-12) | 2-Cl-C₆H₄ | 4,6-di-CH₃-triazin-2-yl | CH₃ | 151 |

TABLE 13-continued

| Example No. | R¹ | R² | R³⁷ | Melting point [°C.] |
|---|---|---|---|---|
| (XV-13) | 2-Cl-benzyl (–CH₂–C₆H₄-Cl) | 4,6-dimethyl-1,3,5-triazin-2-yl | CH₃ | 179 |
| (XV-14) | 2-Cl-phenyl | 4-methyl-6-methoxy-pyrimidin-2-yl | CH₃ | 148 |
| (XV-15) | 2-CH₃-phenyl | 4-methyl-6-methoxy-pyrimidin-2-yl | CH₃ | 163 |
| (XV-16) | 2-SCH₃-phenyl | 4-methyl-6-methoxy-pyrimidin-2-yl | CH₃ | 163 |
| (XV-17) | 2-Cl-phenyl | 4-methyl-pyrimidin-2-yl | CH₃ | 152–153 |
| (XV-18) | 2-Cl-phenyl | 4-methyl-6-hydroxy-pyrimidin-2-yl | CH₃ | 277 (decomp.) |
| (XV-19) | 2-Cl-phenyl | 4,6-dimethyl-pyrimidin-2-yl | CH₃ | 157 |
| (XV-20) | 2-CH₃-phenyl | 4,6-dimethyl-pyrimidin-2-yl | CH₃ | 175 |
| (XV-21) | 2-Cl-phenyl | 2,6-dimethyl-pyrimidin-4-yl | CH₃ | 145 |
| (XV-22) | 2-Cl-phenyl | 2,6-dimethyl-pyridin-4-yl | CH₃ | 118 |
| (XV-23) | 2-OCF₃-phenyl | 4-ethoxy-6-methyl-1,3,5-triazin-2-yl | CH₃ | 103 |
| (XV-24) | 2-Cl-phenyl | 5,6-dimethyl-pyrazin-2-yl | CH₃ | 133 |

PREPARATION OF COMPOUNDS OF THE FORMULA (XVI)

Example (XVI-1)

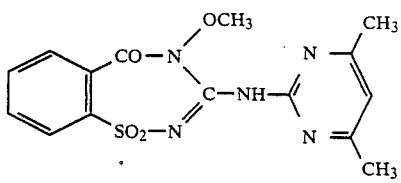

A solution of 60 g (0.25 mole) of 2-chlorocarbonyl-benzenesulphonyl chloride in 100 ml of methylene chloride is added dropwise with stirring to a mixture of 49 g (0.25 mole) of N'-(4,6-dimethyl-pyrimidin-2-yl)-N''-methoxy-guanidine, 50 g (0.63 mole) of pyridine and 200 ml of methylene chloride which has been cooled to −10° C. The reaction mixture is stirred for 3 hours at 20° C., and then washed with twice 200 ml of 5% strength hydrochloric acid and once with 200 ml water, dried, filtered and concentrated. The residue is digested with methanol, and the crystalline product obtained is triturated by filtration with suction.

65 g (72% of theory) of the compound of the structural formula given above and of melting point 185° C. are obtained.

The compounds of the formula (XVI) listed in Table 14 below can be prepared analogously to Example (XVI-1):

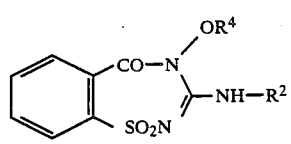 (XVI)

TABLE 14

| Example No. | R² | R⁴ | Melting point [°C.] |
|---|---|---|---|
| (XVI-2) | 4,6-dimethylpyrimidin-2-yl | —CH₂—C₆H₅ | 162 |
| (XVI-3) | 4,6-dimethylpyrimidin-2-yl | —C₈H₁₇(—n) | 136 |
| (XVI-4) | 4,6-dimethylpyrimidin-2-yl | —C₄H₉(—n) | amorphous |
| (XVI-5) | 4,6-dimethylpyrimidin-2-yl | —CH₂CH=CH₂ | 153–156 |
| (XVI-6) | 4,6-dimethylpyrimidin-2-yl | —C₃H₇(—n) | 71–78 |
| (XVI-7) | 4,6-dimethylpyrimidin-2-yl | —C₂H₅ | 181–183 |
| (XVI-8) | 4,6-dimethylpyrimidin-2-yl | —C₃H₇(—i) | 155 |

TABLE 14-continued

| Example No. | R² | R⁴ | Melting point [°C.] |
|---|---|---|---|
| (XVI-9) | 4,6-dimethoxypyrimidin-2-yl | —CH₃ | 180 |

PREPARATION OF STARTING SUBSTANCES OF THE FORMULA (XVIII)

Example (XVIII-1)

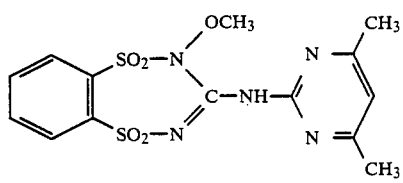

14 g (0.05 mole) of benzene-1,2-disulphonyl dichloride are added in portions to a mixture of 10 g (0.05 mole) of N'-(4,6-dimethyl-pyrimidin-2-yl)-N''-methoxy-guanidine, 12 g (0.15 mole) of pyridine and 100 ml of methylene chloride at −20° C. Stirring is continued for 3 hours at −20° C. and for 15 hours at +20° C.

Thereafter, the reaction mixture is washed with ice-cooled dilute hydrochloric acid and ice water. The methylene chloride solution is dried and concentrated. The residue is triturated with ethanol. The crystalline residue obtained in this procedure is isolated by filtration with suction.

11.5 g (58% of theory) of the compound of the structural formula given above and of melting point 158° C. (decomposition) are obtained.

Working-up of the reaction mixture can also be effected by completely evaporating the mixture when the reaction is complete, taking up the residue in dioxane, filtering the solution and concentrating it once again, and recrystallising the residue.

The compounds of the formula (XVIII) listed in Table 15 below can be prepared analogously to Example (XVIII-1):

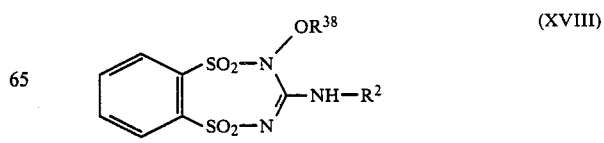 (XVIII)

TABLE 15
| Example No. | R³⁸ | R² | Melting point [°C.] |
|---|---|---|---|
| (XVIII-2) | —C₂H₅ | 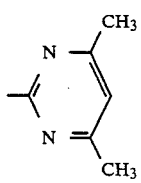 | 104 |
| (XVIII-3) | —C₃H₇(—i) | 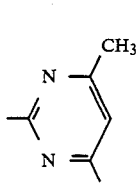 | amorphous |
| (XVIII-4) | —C₃H₇(—i) | 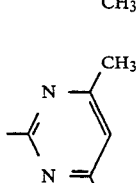 | 134 |
| (XVIII-5) | —C₄H₉(—n) | 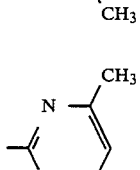 | 179 (decomp.) |
| (XVIII-6) | —C₄H₉(—i) | 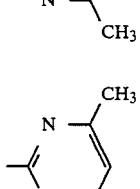 | |
| (XVIII-7) | —C₄H₉(—s) | 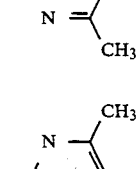 | |
| (XVIII-8) | —C₈H₁₇(—n) | 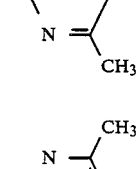 | 164 |
| (XVIII-9) | 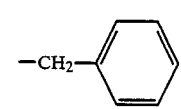 | 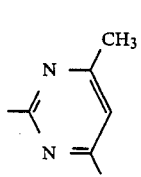 | 198 |

TABLE 15-continued

| Example No. | R³⁸ | R² | Melting point [°C.] |
|---|---|---|---|
| (XVIII-10) | —CH₂—CH₂—C₆H₅ | 4,6-dimethylpyrimidin-2-yl | |
| (XVIII-11) | —CH₂—CH=CH₂ | 4,6-dimethylpyrimidin-2-yl | 180 |
| (XVIII-12) | —CH₂—C₆H₄—NO₂ (p) | 4,6-dimethylpyrimidin-2-yl | |
| (XVIII-13) | —CH₂—C₆H₄—COOC₂H₅ (p) | 4,6-dimethylpyrimidin-2-yl | |
| (XVIII-14) | —CH₂—C₆H₄—F (o) | 4,6-dimethylpyrimidin-2-yl | |
| (XVIII-15) | —CH₂—C₆H₄—CH₃ (p) | 4,6-dimethylpyrimidin-2-yl | |
| (XVIII-16) | —CH₂—C₆H₃Cl₂ (2,6) | 4,6-dimethylpyrimidin-2-yl | |
| (XVIII-17) | —CH₂—COOC₂H₅ | 4,6-dimethylpyrimidin-2-yl | 210 |
| (XVIII-18) | —CH₃ | 4-methylpyrimidin-2-yl | |

TABLE 15-continued

| Example No. | R³⁸ | R² | Melting point [°C.] |
|---|---|---|---|
| (XVIII-19) | —CH₃ | pyrimidine with C₂H₅ | |
| (XVIII-20) | —CH₃ | pyrimidine with OCHF₂ and CH₃ | |
| (XVIII-21) | —CH₃ | pyrimidine with OCH₃, OCH₃ | |
| (XVIII-22) | —C₄H₉(—s) | pyrimidine with OCH₃, OCH₃ | |
| (XVIII-23) | —C₄H₉(—i) | pyrimidine with OCH₃, OCH₃ | |
| (XVIIII-24) | —CH₃ | pyrimidine with OCH₃, CH₃ | 151 (decomp.) |
| (XVIII-25) | —CH₃ | pyrimidine | 187 |

PREPARATION OF STARTING SUBSTANCES OF THE FORMULA (V)

Example (V-1)

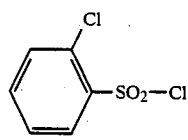

295 ml of phosphoryl chloride ("phosphorus oxychloride") are added dropwise, at 20° C. to 30° C., to a mixture of 172 g (0.8 mole) of sodium 2-chloro-benzenesulphonate, 300 ml of acetonitrile and 300 ml of sulpholane. The reaction mixture is stirred for 4 hours at 70° C., then cooled to 5° C. and diluted with ice water. After extraction with petroleum ether, washing the extract solution with water, drying, filtering and concentrating, the product remaining in the residue is purified by vacuum distillation.

117 g (70% of theory) of 2-chloro-benzenesulphonyl chloride of boiling point 110° C./1 mbar are obtained.

Example (V-2)

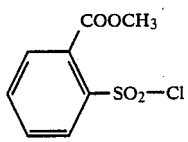

75 g (0.5 mole) of methyl 2-aminobenzoate are dissolved in 176 ml of concentrated hydrochloric acid and 100 ml of acetic acid. A solution of 34.4 g of sodium nitrite in 70 ml of water is added dropwise to this solution at 0° C. After the reaction mixture has been stirred for a further 15 minutes, it is slowly added to a saturated solution of sulphur dioxide in 450 ml of acetic acid, this solution having been cooled to 0° C. After the cooling bath has been removed, stirring is continued until evolution of gas has ended, 10 g of copper(II) chloride being introduced in portions. After dilution with ice water, extraction with methylene chloride, washing of the extract solution with water, drying, filtering and concentrating, the product remaining in the residue is purified by vacuum distillation.

45 g (38% of theory) of 2-methoxycarbonyl-benzenesulphonyl chloride of boiling point 150° C./1.33 mbar are obtained.

The compounds of the formula (V) listed in Table 16 below can be prepared analogously:

$$R^1\text{—}SO_2\text{—}Cl \quad (V)$$

TABLE 16

| Example No. | $R^1$ | Boiling point/mbar |
|---|---|---|
| (V-3) | 2-OCH₃-phenyl | (Oil, decomposition during distillation) |
| (V-4) | 2-phenyl-phenyl | [Melting point: 100° C.] |
| (V-5) | 2-CF₃-phenyl | (Oil) |
| (V-6) | 2-Br-phenyl | 142° C./4 |
| (V-7) | 2-F-phenyl | 106° C./4 |
| (V-8) | 2-OCF₃-phenyl | [Melting point: 32° C.] |
| (V-9) | 2-OCHF₂-phenyl | (Oil, decomposition during distillation) |
| (V-10) | 2-SO₂N(CH₃)₂-phenyl | [Melting point: 103° C.] |
| (V-11) | 2-SCH₃-phenyl | (Oil, decomposition during distillation) |
| (V-12) | 2-SCH(CH₃)₂-phenyl | 90° C./1.33 |
| (V-13) | 2-CH₂SO₂CH₃-phenyl | [Melting point: 120° C.] |
| (V-14) | 2-COOC₂H₅-phenyl | 155° C./5.32 mbar |
| (V-15) | 2-SCHF₂-phenyl |  |
| (V-16) | 2-SCF₃-phenyl | [Melting point: 41–43° C.] |

TABLE 16-continued

| Example No. | R¹ | Boiling point/mbar |
|---|---|---|
| (V-17) | 2-(N-methoxy-N-methylsulfamoyl)phenyl | [Melting point: 99° C.] |
| (V-18) | 2-(methylsulfonyl)phenyl | [Melting point: 128° C.] |
| (V-19) | 2-(n-propoxycarbonyl)phenyl | |
| (V-20) | 2-(isopropoxycarbonyl)phenyl | |
| (V-21) | 2-(cyclopropyloxycarbonyl)phenyl | |
| (V-22) | 2-(n-butoxycarbonyl)phenyl | |
| (V-23) | 2-phenoxyphenyl | |
| (V-24) | 2-cyanophenyl | |
| (V-25) | 2-(methoxycarbonylmethyl)phenyl | [Melting point: 84° C.] |
| (V-26) | 2-(cyanomethyl)phenyl | |

TABLE 16-continued

| Example No. | R¹ | Boiling point/mbar |
|---|---|---|
| (V-27) | 2-(N,N-diethylsulfamoyl)phenyl | [Melting point: 73° C.] |
| (V-28) | 2-(chloromethyl)phenyl | [Melting point: 84° C.] |

The compounds of the formula (XIV) can be prepared analogously.

PREPARATION OF THE STARTING SUBSTANCES OF THE FORMULA (VI)

Example (VI-1)

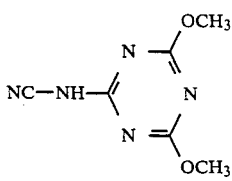

52.7 g (0.3 mole) of 2-chloro-4,6-dimethoxy-s-triazine are added to a solution of 30 g (0.3 mole) of disodium cyanamide in 600 ml of acetone, and the reaction mixture is heated at the boil under reflux for 6 hours. After the solvent has been distilled off, the crystalline residue is dissolved in 250 ml of water, and the solution is acidified with concentrated hydrochloric acid. The crystalline product obtained is isolated by filtration with suction.

33 g (61% of theory) of 2-cyanoamino-4,6-dimethoxy-s-triazine having a melting point above 300° C. are obtained.

Example (VI-2)

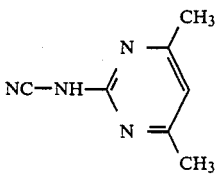

A mixture of 42 g (0.5 mole) of cyanoguanidine ("dicyanodiamide") and 50 g (0.5 mole) of 2,4-pentanedione ("acetylacetone") is heated at 120° C. for 15 hours. After the reaction mixture has been cooled, 500 ml of water is then added, and the solution is acidified with hydrochloric acid at 0° C. to 10° C. The crystalline product obtained in this procedure is isolated by filtration with suction.

51.8 g (70% of theory) of 2-cyanoamino-4,6-dimethyl-pyrimidine of melting point 205° C. are obtained.

Example (VI-3)

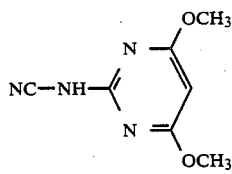

A solution of 24 g (0.427 mole) of potassium hydroxide in 100 ml of water, which solution has been heated to 100° C., is added with stirring to a mixture of 9.2 g (0.043 mole) of 4,6-dimethoxy-pyrimidin-2-yl-thiourea in 70 ml of water at 100° C. Stirring is continued for 2 minutes at 100° C., and a solution of 16.2 g (0.05 mole) of lead(II) acetate in 30 ml of water, which solution has been heated to 100° C., is then added. Heating is continued for a further 5 minutes under reflux, after which the mixture is cooled to 0° C. to 5° C., and 30 ml of glacial acetic acid are added to the aqueous solution. The crystalline product obtained in this procedure is isolated by filtration with suction.

6.3 g (81.5% of theory) of 2-cyanoamino-4,6-dimethoxy-pyrimidine of melting point 202° C. are obtained.

The compounds of the formula (VI) listed in Table 17 below can be prepared analogously:

  (VI)

TABLE 17

| Example No. | R² | Melting point [°C.] |
|---|---|---|
| (VI-4) | 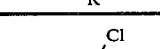 | 203 (decomp.) |
| (VI-5) | 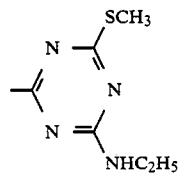 | 258 (decomp.) |
| (VI-6) | 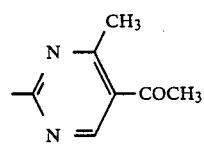 | 114 |
| (VI-7) | 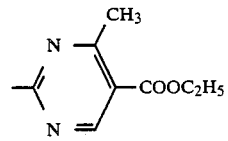 | 210 |
| (VI-8) | 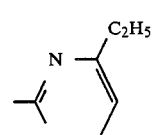 | 156 |
| (VI-9) | 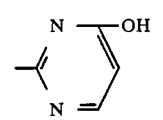 | — |
| (VI-10) | 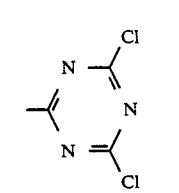 | 174 |
| (VI-11) | 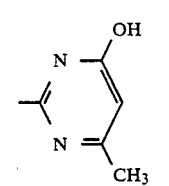 | 126 |
| (VI-12) | 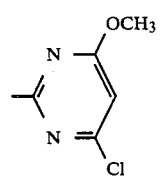 | 146 |
| (VI-13) | N⟵OH (pyrimidine) | >300 |
| (VI-14) | Cl, Cl-triazine | >250 |
| (VI-15) | OH, CH₃-pyrimidine | >270 |
| (VI-16) | OCH₃, Cl-pyrimidine | 200 |

TABLE 17-continued

| Example No. | R² | Melting point [°C.] |
|---|---|---|
| (VI-17) | pyrimidine with OCHF₂ and CH₃ | 174 |
| (VI-18) | pyrimidine with CH₃ and CH₃ | 234 |
| (VI-19) | pyrimidine (unsubstituted) | 186 (decomp.) |
| (VI-20) | pyrimidine with OC₂H₅ and OC₂H₅ | 235–237 (decomp.) |

PREPARATION OF THE STARTING SUBSTANCES OF THE FORMULA (XI)

Example (XI-1)

H₅C₂OOC—NH—CS—NH—(4,6-dimethoxy-pyrimidin-2-yl)

A mixture of 15.5 g (0.1 mole) of 2-amino-4,6-dimethoxy-pyrimidine, 13.1 g (0.1 mole) of ethoxycarbonyl isothiocyanate and 200 ml of acetonitrile is stirred for 2 hours at 60° C. Thereafter, the mixture is cooled to 10° C., and the crystalline product obtained is isolated by filtration with suction.

22.5 g (79% of theory) of 1-(ethoxycarbonyl)-3-(4,6-dimethoxy-pyrimidin-2-yl)-thiourea of melting point 194° C. (decomposition) are obtained.

The compounds of the formula (XI) listed in Table 18 below can be prepared analogously to Example (XI-1):

$$R^{36}-\overset{O}{\underset{\|}{C}}-NH-\overset{S}{\underset{\|}{C}}-NH-R^2 \quad (XI)$$

TABLE 18

| Example No. | R³⁶ | R² | Melting point [°C.] |
|---|---|---|---|
| (XI-2) | phenyl | pyrimidine with OCH₃ and OCH₃ | 189 |
| (XI-3) | phenyl | pyrimidine with CH₃ | 198–199 (decomp.) |
| (XI-4) | —OC₂H₅ | pyrimidine with CH₃ and OCH₃ | 217 |
| (XI-5) | phenyl | pyrimidine with CH₃ and OCH₃ | 190 |
| (XI-6) | phenyl | pyrimidine with Cl and N(CH₃)₂ | 168 |
| (XI-7) | phenyl | pyrimidine with OCHF₂ and CH₃ | 182 |
| (XI-8) | —OC₂H₅ | pyrimidine with OCHF₂ and CH₃ | 184–185 |
| (XI-9) | —OC₂H₅ | pyrimidine with OCHF₂ and OCHF₂ | 173 |
| (XI-10) | —OC₂H₅ | pyrimidine with Cl and OCH₃ | 160–162 |

TABLE 18-continued

| Example No. | R³⁶ | R² | Melting point [°C.] |
|---|---|---|---|
| (XI-11) | —OC₂H₅ | (4,6-dichloropyrimidin-2-yl) | 132–136 |
| (XI-12) | —OC₂H₅ | (4,6-dimethylpyrimidin-2-yl) | 169 |
| (XI-13) | phenyl | (pyrimidin-2-yl) | 173 |
| (XI-14) | phenyl | (4,6-diethoxypyrimidin-2-yl) | 179 |
| (XI-15) | —OC₂H₅ | (4,6-diethoxypyrimidin-2-yl) | 159 |
| (XI-16) | —OC₂H₅ | (4,6-dimethylpyrimidin-2-yl-CH₃) | 140 |
| (XI-17) | phenyl | (4,6-dimethylpyrimidin-2-yl) | 145 |

PREPARATION OF THE STARTING SUBSTANCES OF THE FORMULA (XII)

Example (XII-1)

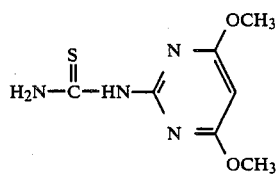

A mixture of 5.0 g (0.0175 mole) of 1-(ethoxycarbonyl)-3-(4,6-dimethoxy-pyrimidin-2-yl)-thiourea, 4.0 g (0.1 mole) of sodium hydroxide and 100 ml of water is stirred for 2 days at 20° C. Dilute hydrochloric acid is then added dropwise, while stirring, until the solution has been rendered acidic and evolution of $CO_2$ has ended. The crystalline product obtained is isolated by filtration with suction.

3.5 g (94% of theory) of (4,6-dimethoxy-pyrimidin-2-yl)-thiourea of melting point 245° C. to 248° C. (decomposition) are obtained.

The compounds of the formula (XII) listed in Table 19 below can be prepared analogously to Example (XII-1):

(XII)

TABLE 19

| Example No. | R² | Melting point [°C.] |
|---|---|---|
| (XII-2) | (4-methyl-pyrimidin-2-yl) CH₃ | 264–265 |
| (XII-3) | (4-methyl-6-methoxy-pyrimidin-2-yl) | 205–207 |
| (XII-4) | (4-difluoromethoxy-6-methyl-pyrimidin-2-yl) OCHF₂, CH₃ | 192–194 |
| (XII-5) | (4-methoxy-6-chloro-pyrimidin-2-yl) OCH₃, Cl | 225–227 |
| (XII-6) | (4,6-dimethyl-pyrimidin-2-yl) | 248 |
| (XII-7) | (4-chloro-6-dimethylamino-pyrimidin-2-yl) Cl, N(CH₃)₂ | |

TABLE 19-continued

| Example No. | R² | Melting point [°C.] |
|---|---|---|
| (XII-8) | (pyrimidinyl with methyl) | 263 |
| (XII-9) | (pyrimidinyl with OC₂H₅, OC₂H₅) 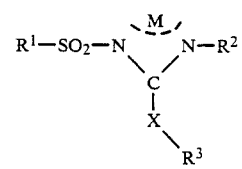 | 166 |
| (XII-10) | (pyridinyl with CH₃, CH₃) 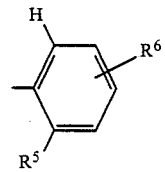 | 259–260 |

Example A

Pre-emergence test/greenhouse
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example, the following compounds from the preparation examples exhibit an excellent activity: (1) and (39).

Example B

Post-emergence test/greenhouse
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, for example, the following compounds from the preparation examples exhibit an excellent activity: (1) and (39).

We claim:

1. A sulphonyliso(thio)urea derivative of the formula $$R^1-SO_2-N \overset{M}{\underset{\underset{X}{\overset{|}{C}}}{\diagdown\diagup}} N-R^2$$
$$\phantom{R^1-SO_2-N\diagdown\diagup N-R^2}\diagdown R^3$$

in which
R¹ represents the radical (phenyl ring with H, R⁶, R⁵ substituents)

wherein
R⁵ and R⁶ are identical or different and represent hydrogen, halogen, cyano, nitro, $C_1$–$C_6$-alkyl (which is optionally substituted by fluorine, chlorine, bromine, cyano, carboxyl, $C_1$–$C_4$-alkoxycarbonyl, $C_1$–$C_4$-alkylaminocarbonyl, di-($C_1$–$C_4$-alkyl)-amino-carbonyl, hydroxyl, $C_1$–$C_4$-alkoxy, formyloxy, $C_1$–$C_4$-alkyl-carbonyloxy, $C_1$–$C_4$-alkoxy-carbonyloxy, $C_1$–$C_4$-alkylamino-carbonyloxy, $C_1$–$C_4$-alkylsulphinyl, $C_1$–$C_4$-alkylsulphonyl, di-($C_1$–$C_4$-alkyl)-aminosulphonyl, $C_3$–$C_6$-cycloalkyl or phenyl), or represent $C_2$–$C_6$-alkenyl (which is optionally substituted by fluorine, chlorine, bromine, cyano, $C_1$–$C_4$-alkoxy-carbonyl, carboxyl or phenyl), or represent $C_2$–$C_6$-alkinyl (which is optionally substituted by fluorine, chlorine bromine, cyano, $C_1$–$C_4$-alkoxy-carbonyl, carboxyl or phenyl), or represent $C_1$–$C_4$-alkoxy (which is optionally substituted by fluorine, chlorine, bromine, cyano, carboxyl, $C_1$–$C_4$-alkoxy-carbonyl, $C_1$–$C_4$-alkoxy, $C_1$–$C_4$-alkylthio, $C_1$–$Ch_4$-alkylsulphinyl or $C_1$–$C_4$-alkylsulphonyl), or represent $C_1$–$C_4$-alkylthio (which is optionally substituted by fluorine, chlorine, bromine, cyano, carboxyl, $C_1$–$C_4$-alkoxy-carbonyl, $C_1$–$C_4$-alkylthio, $C_1$–$C_4$-alkylsulphinyl or $C_1$–$C_4$-alkylsulphonyl), or represent $C_3$–$C_6$-alkenyloxy (which is optionally substituted by fluorine, chlorine, bromine, cyano or $C_1$–$C_4$-alkoxy-carbonyl), or represent $C_2$–$C_6$-alkenylthio (which is optionally substituted by fluorine, chlorine, bromine, cyano, nitro, $C_1$–$C_3$-alkylthio or $C_1$–$C_4$-alkoxy-carbonyl), $C_3$–$C_6$-alkinyloxy, $C_3-C_6$-alkinylthio, or represent the radical $-S(O)_p-R^7$ wherein p represents the numbers 1 or 2 and $R^7$ represents $C_1-C_4$-alkyl (which is optionally substituted by fluorine, chlorine, bromine, cyano or $C_1-C_4$-alkoxy-carbonyl), $C_3-C_6$-alkenyl, $C_3-C_6$-alkinyl, $C_1-C_4$-alkoxy, $C_1-C_4$-alkoxyamino, $C_1-C_4$-alkoxy-$C_1-C_4$-alkyl-amino, $C_1-C_4$-alkylamino or di-($C_1-C_4$-alkyl)-amino, or $R^5$ and $R^6$ furthermore represent phenyl or phenoxy, or represent $C_1-C_4$-alkylcarbonylamino. $C_1-C_4$-alkoxy-carbonylamino, $C_1-C_4$-alkylamino-carbonylamino or di-($C_1-C_4$-alkyl)-amino-carboxylamino, or represent the radical $-CO-R^8$, wherein $R^8$ represents $C_1-C_6$-alkyl, $C_1-C_6$-alkoxy, $C_3-C_6$-cycloalkoxy, $C_3-C_6$-alkenyloxy, $C_1-C_4$-alkylthio, $C_1-C_4$-alkylamino, $C_1-C_4$-alkoxyamino, $C_1-C_4$-alkoxy-$C_1-C_4$-alkyl-amino or di-($C_1-C_4$-alkyl)-amino (which are optionally substituted by fluorine and/or chlorine), or $R^5$ and $R^6$ furthermore represent $C_1-C_4$-alkylsulphonyloxy, di-($C_1-C_4$-alkyl)aminosulphonylamino or the radical $-CH=N-R^9$, wherein $R^9$ represents $C_1-C_6$-alkyl which is optionally substituted by fluorine, chlorine, cyano, carboxyl, $C_1-C_4$-alkoxy, carbonyl, $C_1-C_4$-alkylthio, $C_1-C_4$-alkylsulphinyl or $C_1-C_4$-alkylsulphonyl, or represents benzyl which is optionally substituted by fluorine or chlorine, or represents $C_3-C_6$-alkenyl or $C_3-C_6$-alkinyl, optionally substituted by fluorine or chlorine, or represents phenyl which is optionally substituted by fluorine, chlorine, bromine, $C_1-C_4$-alkyl, $C_1-C_4$-alkoxy, trifluoromethyl, trifluoromethoxy or trifluoromethylthio, or represents $C_1-C_6$-alkoxy, $C_3-C_6$-alkenoxy, $C_3-C_6$-alkinoxy or benzyloxy, optionally substituted by fluorine and/or chlorine, or represents amino, $C_1-C_4$-alkylamino, di-($C_1-C_4$-alkyl)amino, phenylamino, $C_1-C_4$-alkyl-carbonyl-amino, $C_1-C_4$-alkoxy-carbonylamino or $C_1-C_4$-alkylsulphonylamino, or represents phenylsulphonylamino which is optionally substituted by fluorine, chlorine, bromine or methyl;

or wherein, furthermore, $R^1$ represents the radical

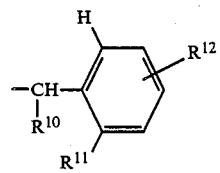

wherein $R^{10}$ represents hydrogen or $C_1-C_4$-alkyl and $R^{11}$ and $R^{12}$ are identical or different and represent hydrogen, fluorine, chlorine, bromine, nitro, cyano, $C_1-C_4$-alkyl (which is optionally substituted by fluorine and/or chlorine), $C_1-C_4$-alkoxy (which is optionally substituted by fluorine and/or chlorine), carboxyl, $C_1-C_4$-alkoxy-carbonyl, $C_1-C_4$-alkylsulphonyl or di-($C_1-C_4$-alkyl)-aminosulphonyl;

or wherein, furthermore, $R^1$ represents the radical

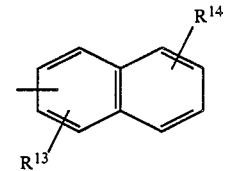

wherein $R^{13}$ and $R^{14}$ are identical or different and represent hydrogen, fluorine, chlorine, bromine, nitro, cyano, $C_1-C_4$-alkyl (which is optionally substituted by fluorine and/or chlorine) or $C_1-C_4$-alkoxy (which is optionally substituted by fluorine and/or chlorine);

or wherein, furthermore, $R^1$ represents the radical

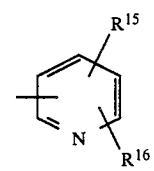

wherein $R^{15}$ and $R^{16}$ are identical or different and represent hydrogen, fluorine, chlorine, bromine, nitro, cyano, $C_1-C_4$-alkyl (which is optionally substituted by fluorine and/or chlorine) or $C_1-C_4$-alkoxy (which is optionally substituted by fluorine and/or chlorine), or represent $C_1-C_4$-alkylthio, $C_1-C_4$-alkylsulphinyl or $C_1-C_4$-alkylsulphonyl (which are optionally substituted by fluorine and/or chlorine), or represent di-($C_1-C_4$-alkyl)-aminosulphonyl or $C_1-C_4$-alkoxycarbonyl;

or wherein, furthermore, $R^1$ represents the radical

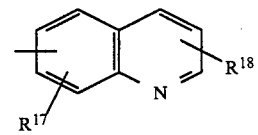

wherein $R^{17}$ and $R^{18}$ are identical or different and represent hydrogen, fluorine, chlorine, bromine, $C_1-C_4$-alkyl (which is optionally substituted by fluorine and/or bromine) or $C_1-C_4$-alkoxy (which is optionally substituted by fluorine and/or chlorine), or represent $C_1-C_4$-alkylthio, $C_1-C_4$-alkylsulphinyl or $C_1-C_4$-alkylsulphonyl (which are optionally substituted by fluorine and/or chlorine), or represent di-($C_1-C_4$-alkyl)-aminosulphonyl;

or wherein, furthermore, $R^1$ represents the radical

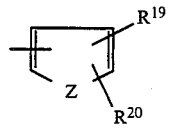

wherein
  $R^{19}$ and $R^{20}$ are identical or different and represent hydrogen, fluorine, chlorine, bromine, cyano, nitro, $C_1$–$C_4$-alkyl (which is optionally substituted by fluorine and/or chlorine), $C_1$–$C_4$-alkoxy (which is optionally substituted by fluorine and/or chlorine), $C_1$–$C_4$-alkylthio, $C_1$–$C_4$-alkylsulphinyl or $C_1$–$C_4$-alkylsulphonyl (which is optionally substituted by fluorine and/or chlorine), di-($C_1$–$C_4$-alkyl)-aminosulphonyl or $C_1$–$C_4$-alkoxy-carbonyl and
  Z represents oxygen, sulphur or the grouping N—$Z^1$, wherein
    $Z^1$ represents hydrogen, $C_1$–$C_4$-alkyl (which is optionally substituted by fluorine, chlorine, bromine or cyano), $C_3$–$C_6$-cycloalkyl, benzyl, phenyl (which is optionally substituted by fluorine, chlorine, bromine or nitro), $C_1$–$C_4$-alkyl-carbonyl, $C_1$–$C_4$-alkoxy-carbonyl or di-($C_1$–$C_4$-alkyl)-aminocarbonyl;

or wherein, furthermore,
  $R^1$ represents the radical

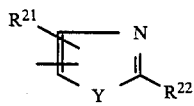

wherein
  $R^{21}$ represents hydrogen, $C_1$–$C_5$-alkyl or halogen
  $R^{22}$ represents hydrogen or $C_1$–$C_5$-alkyl and
  Y represents sulphur or the grouping N—$R^{23}$ wherein
    $R^{23}$ represents hydrogen or $C_1$–$C_5$-alkyl;
and wherein, furthermore,
  $R^2$ represents the radical

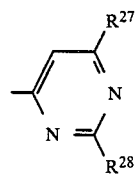

wherein
  $R^{27}$ and $R^{28}$ are identical or different and represent hydrogen, fluorine, chlorine, bromine, $C_1$–$C_4$-alkyl (which is optionally substituted by fluorine and/or chlorine), $C_1$–$C_4$-alkoxy (which is optionally substituted by fluorine and/or chlorine), $C_1$–$C_4$-alkyl-amino or di-($C_1$–$C_4$-alkyl)-amino, with the proviso that at least one of the radicals $R^{27}$ and $R^{28}$ is other than hydrogen;
or wherein, furthermore,
  $R^2$ represents the radical

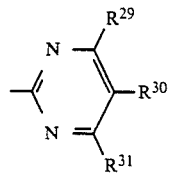

wherein
  $R^{29}$ represents hydrogen, fluorine, chlorine, bromine, hydroxyl, $C_1$–$C_4$-alkyl (which is optionally substituted by fluorine and/or chlorine) or $C_1$–$C_4$-alkoxy (which is optionally substituted by fluorine and/or chlorine),
  $R^{30}$ represents hydrogen, fluorine, chlorine, bromine, $C_1$–$C_4$-alkyl (which is optionally substituted by fluorine and/or chlorine), cyano, formyl, $C_1$–$C_4$-alkyl-carbonyl or $C_1$–$C_4$-alkoxycarbonyl and
  $R^{31}$ represents hydrogen, fluorine, chlorine, bromine, hydroxyl, $C_1$–$C_4$-alkyl (which is optionally substituted by fluorine and/or chlorine), $C_1$–$C_4$-alkoxy (which is optionally substituted by fluorine and/or chlorine), amino, $C_1$–$C_4$-alkyl-amino or di-($C_1$–$C_4$-alkyl)-amino, or
  $R^{30}$ and $R^{31}$ together represent $C_3$–$C_4$-alkanediyl;
or wherein, furthermore,
  $R^3$ represents a phenyl radical, which is optionally substituted by one or more of the radicals from the series comprising halogen, cyano, nitro, hydroxyl, carboxyl, $C_1$–$C_6$-alkyl (which is optionally substituted by fluorine, chlorine, bromine, nitro, cyano, hydroxyl, carboxyl, $C_1$–$C_4$-alkoxy-carbonyl, $C_1$–$C_4$-alkoxy, $C_1$–$C_4$-alkylthio or phenyl), $C_3$–$C_6$-cycloalkyl $C_1$–$C_4$-alkoxy (which is optionally substituted by flourine, chlorine, bromine, cyano, carboxyl, $C_1$–$C_4$-alkoxy, $C_1$–$C_4$-alkylthio or $C_1$–$C_4$-alkoxy-carbonyl), $C_1$–$C_4$-alkylthio (which is optionally substituted by fluorine, chlorine, bromine, byano, carboxyl or $C_1$–$C_4$-alkoxy-carbonyl), amino, $C_1$–$C_4$-alkyl-amino and di-($C_1$–$C_4$-alkyl)-amino (which are optionally substituted by fluorine, chlorine, bromine, cyano, carboxyl, $C_1$–$C_4$-alkoxy or $C_1$–$C_4$-alkoxycarbonyl), $C_1$–$C_4$-alkyl-carbonyl-amino, $C_1$–$C_4$-alkoxy-carbonyl-amino, (di)-$C_1$–$C_4$-alkylaminocarbonyl-amino, formyl, $C_1$–$C_4$-alkyl-carbonyl, benzoyl, $C_1$–$C_4$-alkoxy-carbonyl, phenoxy-carbonyl, benzyloxycarbonyl, phenyl (which is optionally substituted by fluorine, chlorine, bromine, cyano, nitro, hydroxyl or methyl), phenoxy, phenylthio, phenylsulphonyl, phenylamino and phenylazo (which are optionally substituted by fluorine, chlorine, bromine, cyano, nitro, methyl and/or trifluoromethyl), pyridoxy and pyrimidoxy (which are optionally substituted by fluorine, chlorine, bromine, cyano, nitro, methyl and/or trifluoromethyl), $C_1$–$C_4$-alkyl-carbonyloxy, $C_1$–$C_4$-alkoxycarbonyloxy, $C_1$–$C_4$-alkyl-aminocarbonyloxy and di-($C_1$–$C_4$-alkyl)-amino-carbonyloxy, or which is optionally fused with an alkylene chain (which is optionally branched and/or interrupted by one or more oxygen atoms) or a benzo radical (which is optionally substituted by fluorine, chlorine, bromine, cyano, nitro, methyl and/or trifluoromethyl);
or wherein, furthermore,
  $R^3$ represents a

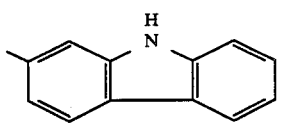

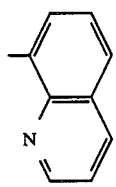

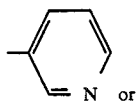

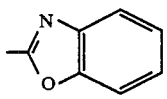

which is optionally substituted by fluorine, chlorine, bromine, cyano, nitro, $C_1$–$C_3$-alkyl or $C_1$–$C_3$-alkoxy (the latter optionally being substituted by fluorine and/or chlorine);

and wherein, furthermore,

X represents oxygen or sulphur and

M represents hydrogen or one equivalent of sodium, potassium, magnesium, calcium, aluminium, manganese, iron, cobalt or nickel, or an adduct thereof with a strong acid.

2. A compound according to claim 1, in which $R^1$ represents the radical

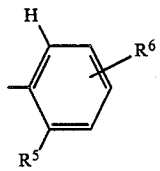

wherein $R^5$ represents fluorine, chlorine, bromine, methyl, trifluoromethyl, methoxy, difluoromethoxy, trifluoromethoxy, $C_1$–$C_3$-alkylthio, difluoromethylthio, trifluoromethylthio, $C_1$–$C_3$-alkylsulphinyl, $C_1$–$C_3$-alkylsulphonyl, dimethylaminosulphonyl, diethylaminosulphonyl, N-methoxy-N-methylaminosulphonyl, phenyl, phenoxy, $C_1$–$C_3$-alkoxy-carbonyl or $C_1$–$C_3$-alkyl-aminocarbonyl and $R^6$ represents hydrogen;

and wherein, furthermore, $R^2$ represents the radical

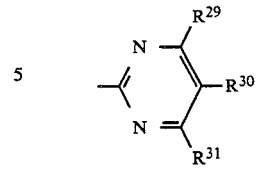

wherein $R^{29}$ represents hydrogen, fluorine, chlorine bromine, hydroxyl, $C_1$–$C_3$-alkyl, $C_1$–$C_3$-alkoxy or difluoromethoxy, $R^{30}$ represents hydrogen, chlorine, bromine or methyl and $R^{31}$ represents $C_1$–$C_3$-alkyl, hydroxyl, fluorine, chlorine, bromine or $C_1$–$C_3$-alkoxy;

and wherein, furthermore, $R^3$ represents a phenyl radical which is optionally substituted by one or two radicals from the series comprising fluorine, chlorine, bromine, iodine, cyano, nitro, hydroxyl, carboxyl, $C_1$–$C_3$-alkoxycarbonyl, $C_1$–$C_4$-alkyl, trifluoromethyl, hydroxymethyl, methoxycarbonylmethyl, phenyl-$C_1$–$C_3$-alkyl, cyclohexyl, $C_1$–$C_3$-alkoxy, trifluoromethoxy, $C_1$–$C_3$-alkylthio, trifluoromethylthio, dimethylamino, amino, acetylamino, methylaminocarbonyl, formyl, acetyl, benzoyl, phenyl, hydroxyphenyl, phenoxy (which is optionally substituted by chlorine and/or trifluoromethyl), phenylamino, phenylazo and pyridoxy (which is optionally substituted by chlorine and/or trifluoromethyl), or which is optionally benzofused, M represents hydrogen or one equivalent of sodium, potassium or calcium, or an adduct thereof with a hydrogen halide acid, sulphuric acid, an alkanesulphonic acid which has 1 to 4 carbon atoms and is optionally substituted by fluorine and/or chlorine, or a benzene- or naphthalene-sulphonic acid, which is optionally substituted by fluorine, chlorine, bromine or methyl.

3. A compound or adduct according to claim 2, in which X is O.

4. A herbicidal composition comprising a herbicidally effective amount of a compound or adduct thereof according to claim 1 and a diluent.

5. A method of combating unwanted vegetation which comprises applying to such vegetation or to a locus from which it is desired to exclude such vegetation a herbicidally effective amount of a compound or adduct thereof according to claim 1.

6. A process for producing a compound according to claim 1, comprising reacting a compound of the formula

in which $M^1$ is hydrogen or one equivalent of a metal, with a sulphonylguanidine derivative of the formula

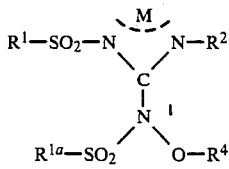

in which
R$^{1a}$ independently has the same meaning as R$^1$, but does not have to be identical to R$^1$ in each individual case and
R$^4$ is an C$_{1-4}$ alkyl or benzyl hydrocarbon radical.

7. A sulphonylsio(thio) urea derivative of the formula

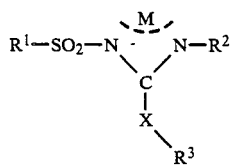

in which
R$^1$ represents the radical

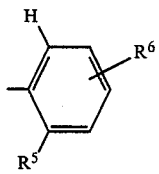

wherein
R$^5$ and R$^6$ are identical or different and represent hydrogen, halogen, cyano, nitro, C$_1$-C$_6$-alkyl (which is optionally substituted by fluorine, chlorine, cyano, C$_1$-C$_4$-alkoxycarbonyl, C$_1$-C$_4$-alkoxy, or phenyl), or represent C$_1$-C$_4$-alkoxy (which is optionally substituted by fluorine, chlorine, cyano, C$_1$-C$_4$-alkoxy-carbonyl or C$_1$-C$_4$-alkoxy) or represent C$_1$-C$_4$-alkylthio (which is optionally substituted by fluorine, chlorine, cyano or C$_1$-C$_4$-alkoxycarbonyl), or represent the radical —S(O)$_p$—R$^7$
wherein
p represents the numbers 1 or 2 and
R$^7$ represents C$_1$-C$_4$-alkyl (which is optionally substituted by fluorine, chlorine, cyano or C$_1$-C$_4$-alkoxycarbonyl), C$_1$-C$_4$-alkoxy-amino, C$_1$-C$_4$-alkoxyC$_1$-C$_4$-alkyl-amino or di-(C$_1$-C$_4$-alkyl)-amino, or
R$^5$ and R$^6$ furthermore represent phenyl or represent the radical —CO—R$^8$,
R$^8$ represents C$_1$-C$_6$-alkoxy (which is optionally substituted by fluorine and/or chlorine);
or in which, furthermore
R$^1$ represents the radical

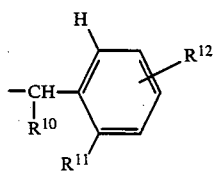

wherein
R$^{10}$ represents hydrogen and
R$^{11}$ and R$^{12}$ are identical or different and represent hydrogen, fluorine, chlorine, bromine, nitro, cyano, C$_1$-C$_4$-alkyl (which is optionally substituted by fluorine and/or chlorine), C$_1$-C$_4$-alkoxy (which is optionally substituted by fluorine and/or chlorine), C$_1$-C$_4$-alkoxy-carbonyl, C$_1$-C$_4$-alkylsulphonyl or di-(C$_1$-C$_4$-alkyl)-aminosulphonyl;
or in which, furthermore,
R$^1$ represents the radical

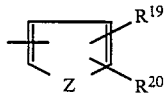

wherein
R$^{19}$ and R$^{20}$ are identical or different and represent hydrogen, fluorine, chlorine, bromine, cyano, nitro, C$_1$-C$_4$-alkyl (which is optionally substituted by fluorine and/or chlorine), C$_1$-C$_4$-alkoxy (which is optionally substituted by fluorine and/or chlorine), C$_1$-C$_4$-alkylthio, C$_1$-C$_4$-alkylsulphinyl or C$_1$-C$_4$-alkylsulphonyl (which is optionally substituted by fluorine and/or chlorine), di-(C$_1$-C$_4$-alkyl)-aminosulphonyl or C$_1$-C$_4$-alkoxy-carbonyl and
Z represents sulphur,
and in which furthermore,
R$^2$ represents the radical

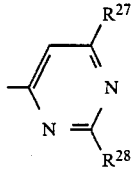

wherein
R$^{27}$ and R$^{28}$ are identical or different and represent hydrogen, fluorine, chlorine, bromine, C$_1$-C$_4$-alkyl (which is optionally substituted by fluorine and/or chlorine), C$_1$-C$_4$-alkoxy (which is optionally substituted by fluorine and/or chlorine), C$_1$-C$_4$-alkylamino or di-(C$_1$-C$_4$-alkyl)-amino, with the proviso that at least one of the radicals R$^{27}$ and R$^{28}$ is other than hydrogen,
or in which furthermore,
R$^2$ represents the radical

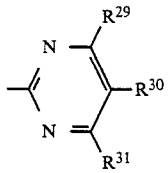

wherein
R$^{29}$ represents hydrogen, fluorine, chlorine, bromine, hydroxyl, C$_1$-C$_4$-alkyl (which is optionally substituted by fluorine and/or chlorine) or C$_1$-C$_4$-alkoxy (which is optionally substituted by fluorine and/or chlorine),
R$^{30}$ represents hydrogen, fluorine, chlorine, bromine, C$_1$-C$_4$-alkyl (which is optionally substituted by fluorine and/or chlorine), cyano, formyl, $C_1$–$C_4$-alkyl-carbonyl or $C_1$–$C_4$-alkoxycarbonyl and $R^{31}$ represents hydrogen, fluorine, chlorine, bromine, hydroxyl, $C_1$–$C_4$-alkyl (which is optionally substituted by fluorine and/or chlorine), $C_1$–$C_4$-alkoxy (which is optionally substituted by fluorine and/or chlorine), amino, $C_1$–$C_4$-alkyl-amino or di-($C_1$–$C_4$-alkyl)-amino, or $R^{30}$ and $R^{31}$ together represent $C_3$–$C_4$-alkanediyl;

or in which, furthermore, $R^3$ represents a phenyl radical, which is optionally substituted by one or more of the radicals from the series comprising halogen, cyano, nitro, hydroxyl, carboxyl, $C_1$–$C_6$-alkyl (which is optionally substituted by fluorine, chlorine, bromine, nitro, cyano, hydroxyl, carboxyl, $C_1$–$C_4$-alkoxy-carbonyl $C_1$–$C_4$-alkoxy, $C_1$–$C_4$-alkylthio or phenyl), $C_3$–$C_6$-cycloalkyl, $C_1$–$C_4$-alkoxy (which is optionally substituted by fluorine, chlorine, bromine, cyano, carboxyl, $C_1$–$C_4$-alkoxy, $C_1$–$C_4$-alkylthio or $C_1$–$C_4$-alkylthio or $C_1$–$C_4$-alkoxy-carbonyl), $C_1$–$C_4$-alkylthio (which is optionally substituted by fluorine, chlorine, bromine, cyano, carboxyl or $C_1$–$C_4$-alkoxy-carbonyl), amino, $C_1$–$C_4$-alkyl-amino and di-($C_1$–$C_4$-alkyl)-amino (which is optionally substituted by fluorine, chlorine, bromine, cyano, carboxyl, $C_1$–$C_4$-alkoxy or $C_1$–$C_4$-alkoxycarbonyl), $C_1$–$C_4$-alkyl-carbonyl-amino, $C_1$–$C_4$-alkoxy-carbonyl-amino, (di)-$C_1$–$C_4$-alkylaminocarbonyl-amino, formyl, $C_1$–$C_4$-alkyl-carbonyl, benzoyl, $C_1$–$C_4$-alkoxy-carbonyl, phenoxy-carbonyl, benzyloxycarbonyl, phenyl (which is optionally substituted by fluorine, chlorine, bromine, cyano, nitro, hydroxyl or methyl), phenoxy, phenylthio, phenylsulphonyl, phenylamino, $C_1$–$C_4$-alkyl-carbonyloxy, $C_1$–$C_4$-alkoxy-carbonyloxy, $C_1$–$C_4$-alkyl-aminocarbonyloxy and di-($C_1$–$C_4$-alkyl)-amino-carbonyloxy, or which is optionally fused with an alkylene chain (which is optionally branched and/or interrupted by one or more oxygen atoms) or a benzo radical (which is optionally substituted by fluorine, chlorine, bromine, cyano, nitro, methyl and/or trifluoromethyl);

or wherein, furthermore, $R^3$ represents a

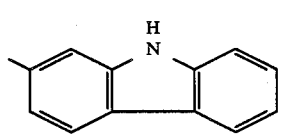

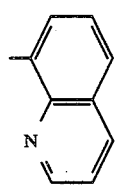

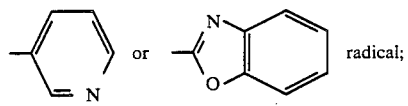

radical;

and wherein, furthermore,

X represents oxygen or sulphur and

M represents hydrogen or one equivalent of sodium, potassium, magnesium or calcium.

8. A compound according to claim 7 in which $R^1$ represents the radical

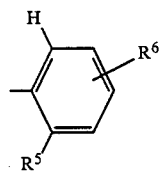

wherein $R^5$ represents fluorine, chlorine, bromine, methyl, trifluoromethyl, methoxy, difluoromethoxy, trifluoromethoxy, $C_1$–$C_3$-alkylthio, difluoromethylthio, trifluoromethylthio, $C_1$–$C_3$-alkylsulphinyl, $C_1$–$C_3$-alkylsulphonyl, dimethylaminosulphonyl, diethylaminosulphonyl, N-methoxy-N-methylaminosulphonyl, phenyl or $C_1$–$C_3$-alkoxycarbonyl and $R^6$ represents hydrogen;

and in which, furthermore, $R^2$ represents the radical

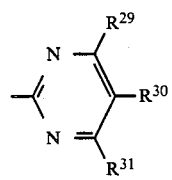

wherein $R^{29}$ represents hydrogen, fluorine, chlorine bromine, hydroxyl, $C_1$–$C_3$-alkyl, $C_1$–$C_3$-alkoxy or difluoromethoxy, $R^{30}$ represents hydrogen, chlorine, bromine or methyl and $R^{31}$ represents $C_1$–$C_3$-alkyl, hydroxyl, fluorine, chlorine, bromine or $C_1$–$C_3$-alkoxy;

and in which, furthermore, $R^3$ represents a phenyl radical which is optionally substituted by one or two radicals from the series comprising fluorine, chlorine, bromine, iodine, cyano, nitro, hydroxyl, carboxyl, $C_1$–$C_3$-alkoxycarbonyl, $C_1$–$C_4$-alkyl, trifluoromethyl, hydroxymethyl, methoxycarbonylmethyl, phenyl-$C_1$–$C_3$-alkyl, cyclohexyl, $C_1$–$C_3$-alkoxy, trifluoromethoxy, $C_1$–$C_3$-alkylthio, trifluoromethylthio, dimethylamino, amino, acetylamino, methylaminocarbonyl, formyl, acetyl, benzoyl, phenyl, hydroxyphenyl, phenoxy or phenylamino, or which is optionally fused, and M represents hydrogen or one equivalent of sodium, potassium or calcium.

* * * * *

UNITED STATES PATENT AND TRADEMARK OFFICE
CERTIFICATE OF CORRECTION

PATENT NO. : 4,840,661

DATED : June 20, 1989

INVENTOR(S) : Diehr et al.

It is certified that error appears in the above-identified patent and that said Letters Patent is hereby corrected as shown below:

| | |
|---|---|
| Title Page | ABSTRACT: Line 1 delete 1st " relates ", line 5 delete " represent " and substitute -- represents --, lines 9-10 delete " radial " and substitute -- radical -- |
| Col. 182, line 57 | Delete " $Ch_4$ " and substitute -- $C_4$ -- |
| Col. 183, lines 14-15 | Delete " carboxylamino " and substitute -- carbonylamino -- |
| Col. 187, line 25 | After formula insert -- radical -- |
| Col. 192, line 8 | Delete " radical " |

Signed and Sealed this

First Day of September, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO. : 4,840,661
DATED : June 20, 1989
INVENTOR(S) : Diehr et al.

It is certified that error appears in the above-identified patent and that said Letters Patent is hereby corrected as shown below:

Col. 186, line 41  Delete " byano " and substitute -- cyano --

Signed and Sealed this

Ninth Day of November, 1993

Attest:

Attesting Officer

BRUCE LEHMAN

Commissioner of Patents and Trademarks